(12) United States Patent
Valamehr et al.

(10) Patent No.: US 12,275,955 B2
(45) Date of Patent: Apr. 15, 2025

(54) COMBINING iPSC DERIVED EFFECTOR CELL TYPES FOR IMMUNOTHERAPY USE

(71) Applicant: Fate Therapeutics, Inc., San Diego, CA (US)

(72) Inventors: Bahram Valamehr, San Diego, CA (US); Jode Goodridge, San Diego, CA (US); Ryan Bjordahl, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/002,248

(22) PCT Filed: Jun. 18, 2021

(86) PCT No.: PCT/US2021/038134
§ 371 (c)(1),
(2) Date: Dec. 16, 2022

(87) PCT Pub. No.: WO2021/258016
PCT Pub. Date: Dec. 23, 2021

(65) Prior Publication Data
US 2023/0235287 A1 Jul. 27, 2023

Related U.S. Application Data

(60) Provisional application No. 63/041,672, filed on Jun. 19, 2020.

(51) Int. Cl.
| | | |
|---|---|---|
| *C12N 5/0783* | (2010.01) | |
| *A61K 39/00* | (2006.01) | |
| *A61P 35/00* | (2006.01) | |
| *C07K 14/715* | (2006.01) | |
| *C07K 14/735* | (2006.01) | |

(52) U.S. Cl.
CPC ........ *C12N 5/0636* (2013.01); *A61K 39/4611* (2023.05); *A61K 39/4613* (2023.05); *A61K 39/4631* (2023.05); *A61K 39/464412* (2023.05); *A61P 35/00* (2018.01); *C07K 14/70535* (2013.01); *C07K 14/7155* (2013.01); *C12N 5/0646* (2013.01); *A61K 2239/31* (2023.05); *A61K 2239/38* (2023.05); *A61K 2239/48* (2023.05); *C07K 2319/02* (2013.01); *C07K 2319/03* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 6,140,081 A | 10/2000 | Barbas | |
| 6,352,694 B1 | 3/2002 | June et al. | |
| 6,453,242 B1 | 9/2002 | Eisenberg et al. | |
| 6,534,261 B1 | 3/2003 | Cox, III et al. | |
| 7,888,121 B2 | 2/2011 | Urnov et al. | |
| 7,972,854 B2 | 7/2011 | Miller et al. | |
| 8,409,577 B2 | 4/2013 | Thompson et al. | |
| 9,447,194 B2 | 9/2016 | Jensen | |
| 9,587,020 B2 | 3/2017 | Wu et al. | |
| 10,287,606 B2* | 5/2019 | Valamehr | ................ A61P 35/00 |
| 10,927,346 B2* | 2/2021 | Valamehr | .............. C12N 5/0636 |
| 11,072,781 B2* | 7/2021 | Valamehr | .............. C12N 5/0696 |
| 11,365,394 B2* | 6/2022 | Valamehr | .............. C12N 15/113 |
| 2004/0101519 A1 | 5/2004 | June et al. | |
| 2006/0034810 A1 | 2/2006 | Riley et al. | |
| 2011/0145940 A1 | 6/2011 | Voytas et al. | |
| 2014/0134142 A1 | 5/2014 | Smith et al. | |
| 2014/0219975 A1 | 8/2014 | June et al. | |
| 2015/0140665 A1 | 5/2015 | Calos et al. | |
| 2016/0009813 A1 | 1/2016 | Themeli et al. | |
| 2016/0046700 A1 | 2/2016 | Foster et al. | |
| 2016/0058857 A1 | 3/2016 | Spencer et al. | |
| 2017/0166877 A1 | 6/2017 | Bayle et al. | |
| 2017/0183407 A1 | 6/2017 | Cooper et al. | |
| 2018/0155717 A1* | 6/2018 | Valamehr | ................ A61P 35/02 |
| 2020/0069734 A1 | 3/2020 | Valamehr et al. | |

FOREIGN PATENT DOCUMENTS

| | | |
|---|---|---|
| WO | WO 1998/053058 A1 | 11/1998 |
| WO | WO 1998/053059 A1 | 11/1998 |
| WO | WO 1998/053060 A1 | 11/1998 |
| WO | WO 2002/016536 A1 | 2/2002 |
| WO | WO 2003/016496 A2 | 2/2003 |

(Continued)

OTHER PUBLICATIONS

Donnelly et al., "The 'cleavage' activities of foot-and-mouth disease virus 2A site-directed mutants and naturally occurring '2A-like' sequences," *J. Gen. Virol.*, 82:1027-1041 (2001).
Dragomir et al., "Key questions about the checkpoint blockade-are microRNAs an answer?," *Cancer Biol. Med.*, 15(2):103-115 (2018).
Hegde et al., "Tandem CAR T cells targeting HER2 and IL13Rα2 mitigate tumor antigen escape," *J. Clin. Invest.*, 126(8):3036-3052 (2016).

(Continued)

*Primary Examiner* — Yunsoo Kim
(74) *Attorney, Agent, or Firm* — Greenberg Traurig, LLP

(57) ABSTRACT

Provided are methods and compositions for obtaining functionally enhanced derivative effector cells obtained from directed differentiation of genomically engineered iPSCs. The derivative cells provided herein have stable and functional genome editing that delivers improved or enhanced therapeutic effects. Also provided are therapeutic compositions and the use thereof comprising the functionally enhanced derivative effector cells alone, or with antibodies or checkpoint inhibitors or additional cells in combination therapies.

40 Claims, 9 Drawing Sheets
Specification includes a Sequence Listing.

(56) References Cited

FOREIGN PATENT DOCUMENTS

| | | |
|---|---|---|
| WO | WO 2011/159726 A2 | 12/2011 |
| WO | WO 2015/134652 A1 | 9/2015 |
| WO | WO 2015/148926 A1 | 10/2015 |
| WO | WO 2017/066634 A1 | 4/2017 |
| WO | WO 2017/078807 A1 | 5/2017 |
| WO | WO 2017/127755 A1 | 7/2017 |
| WO | WO 2019/075057 A1 | 4/2019 |
| WO | WO 2019/112899 A2 | 6/2019 |
| WO | WO 2020/210398 A1 | 10/2020 |

OTHER PUBLICATIONS

Nianias et al., "Induced Pluripotent Stem Cell (iPSC)-Derived Lymphocytes for Adoptive Cell Immunotherapy: Recent Advances and Challenges," *Curr. Hem. Malig. Rep.*, 14:261-268 (2019).

Ryan et al., "Cleavage of foot-and-mouth disease virus polyprotein is mediated by residues located within a 19 amino acid sequence," *J. Gen. Virol.*, 72:2727-2732 (2001).

Wang et al., "CAR-NK for tumor immunotherapy: Clinical transformation and future prospects," *Cancer Lett.*, 472:175-180 (2020).

Goodridge et al., "Abstract 2216: Combinational strategy targeting B cell malignancy using iPSC engineered CAR-NK (FT596) and CAR-T cell (FT819) platforms with therapeutic antibody to achieve an effective deep and durable response," *Cancer Res.*, 80(16_Supplement):2216 (2020).

Goodridge et al., "FT596: Translation of First-of-Kind Multi-Antigen Targeted Off-the-Shelf CAR-NK Cell with Engineered Persistence for the Treatment of B Cell Malignancies," *Blood*, 134(Supplement 1):301 (2019).

\* cited by examiner

SEQUENCE LISTING

<160> NUMBER OF SEQ ID NOS: 16

<210> SEQ ID NO 1
<211> LENGTH: 340
<212> TYPE: PRT
<213> ORGANISM: Artificial Sequence
<220> FEATURE:
<223> OTHER INFORMATION: CD64 domain-based construction

<400> SEQUENCE: 1

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Tyr Gln Val Ser Phe Cys Leu Val Met Val Leu Leu
```

```
                290                 295                 300
Phe Ala Val Asp Thr Gly Leu Tyr Phe Ser Val Lys Thr Asn Ile Arg
305                 310                 315                 320

Ser Ser Thr Arg Asp Trp Lys Asp His Lys Phe Lys Trp Arg Lys Asp
                325                 330                 335

Pro Gln Asp Lys
            340

<210> SEQ ID NO 2
<211> LENGTH: 336
<212> TYPE: PRT
<213> ORGANISM: Artificial Sequence
<220> FEATURE:
<223> OTHER INFORMATION: CD64 exon-based construction

<400> SEQUENCE: 2

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Phe Phe Pro Pro Gly
        275                 280                 285

Tyr Gln Val Ser Phe Cys Leu Val Met Val Leu Leu Phe Ala Val Asp
290                 295                 300

Thr Gly Leu Tyr Phe Ser Val Lys Thr Asn Ile Arg Ser Ser Thr Arg
```

```
                305                 310                 315                 320
Asp Trp Lys Asp His Lys Phe Lys Trp Arg Lys Asp Pro Gln Asp Lys
                325                 330                 335

<210> SEQ ID NO 3
<211> LENGTH: 335
<212> TYPE: PRT
<213> ORGANISM: Artificial Sequence
<220> FEATURE:
<223> OTHER INFORMATION: CD64 exon-based construction

<400> SEQUENCE: 3

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Phe Pro Pro Gly Tyr
        275                 280                 285

Gln Val Ser Phe Cys Leu Val Met Val Leu Leu Phe Ala Val Asp Thr
    290                 295                 300

Gly Leu Tyr Phe Ser Val Lys Thr Asn Ile Arg Ser Ser Thr Arg Asp
305                 310                 315                 320

Trp Lys Asp His Lys Phe Lys Trp Arg Lys Asp Pro Gln Asp Lys
                325                 330                 335
```

```
<210> SEQ ID NO 4
<211> LENGTH: 1032
<212> TYPE: DNA
<213> ORGANISM: Artificial Sequence
<220> FEATURE:
<223> OTHER INFORMATION: CD64 domain-based construction (encoding SEQ ID
      NO. 1)

<400> SEQUENCE: 4
cttggagaca acatgtggtt cttgacaact ctgctccttt gggttccagt tgatgggcaa      60
gtggacacca caaaggcagt gatcactttg cagcctccat gggtcagcgt gttccaagag     120
gaaaccgtaa ccttgcattg tgaggtgctc catctgcctg ggagcagctc tacacagtgg     180
tttctcaatg gcacagccac tcagacctcg accccccagct acagaatcac ctctgccagt    240
gtcaatgaca gtggtgaata caggtgccag agaggtctct cagggcgaag tgaccccata     300
cagctggaaa tccacagagg ctggctacta ctgcaggtct ccagcagagt cttcacggaa     360
ggagaacctc tggccttgag gtgtcatgcg tggaaggata agctggtgta caatgtgctt     420
tactatcgaa atggcaaagc ctttaagttt ttccactgga attctaacct caccattctg     480
aaaaccaaca taagtcacaa tggcacctac cattgctcag gcatgggaaa gcatcgctac    540
acatcagcag gaatatctgt cactgtgaaa gagctatttc cagctccagt gctgaatgca    600
tctgtgacat ccccactcct ggaggggaat ctggtcaccc tgagctgtga aacaaagttg    660
ctcttgcaga ggcctggttt gcagctttac ttctccttct acatgggcag caagaccctg    720
cgaggcagga acacatcctc tgaataccaa atactaactg ctagaagaga agactctggg    780
ttatactggt gcgaggctgc cacagaggat ggaaatgtcc ttaagcgcag ccctgagttg    840
gagcttcaag tgcttggcct ccagttacca actcctgtct ggtttcatta ccaagtctct    900
ttctgcttgg tgatggtact ccttttttgca gtggacacag gactatattt ctctgtgaag    960
acaaacattc gaagctcaac aagagactgg aaggaccata aatttaaatg gagaaaggac   1020
cctcaagaca aa                                                       1032

<210> SEQ ID NO 5
<211> LENGTH: 1020
<212> TYPE: DNA
<213> ORGANISM: Artificial Sequence
<220> FEATURE:
<223> OTHER INFORMATION: CD64 exon-based construction (encoding SEQ ID
      NO. 2)

<400> SEQUENCE: 5
cttggagaca acatgtggtt cttgacaact ctgctccttt gggttccagt tgatgggcaa      60
gtggacacca caaaggcagt gatcactttg cagcctccat gggtcagcgt gttccaagag     120
gaaaccgtaa ccttgcattg tgaggtgctc catctgcctg ggagcagctc tacacagtgg     180
tttctcaatg gcacagccac tcagacctcg accccccagct acagaatcac ctctgccagt    240
gtcaatgaca gtggtgaata caggtgccag agaggtctct cagggcgaag tgaccccata     300
cagctggaaa tccacagagg ctggctacta ctgcaggtct ccagcagagt cttcacggaa     360
ggagaacctc tggccttgag gtgtcatgcg tggaaggata agctggtgta caatgtgctt     420
tactatcgaa atggcaaagc ctttaagttt ttccactgga attctaacct caccattctg     480
aaaaccaaca taagtcacaa tggcacctac cattgctcag gcatgggaaa gcatcgctac    540
acatcagcag gaatatctgt cactgtgaaa gagctatttc cagctccagt gctgaatgca    600
tctgtgacat ccccactcct ggaggggaat ctggtcaccc tgagctgtga aacaaagttg    660
```

-continued

```
ctcttgcaga ggcctggttt gcagctttac ttctccttct acatgggcag caagaccctg    720
cgaggcagga acacatcctc tgaataccaa atactaactg ctagaagaga agactctggg    780
ttatactggt gcgaggctgc cacagaggat ggaaatgtcc ttaagcgcag ccctgagttg    840
gagcttcaag tgcttggttt gttctttcca cctgggtacc aagtctcttt ctgcttggtg    900
atggtactcc ttttgcagt ggacacagga ctatatttct ctgtgaagac aaacattcga    960
agctcaacaa gagactggaa ggaccataaa tttaaatgga gaaggaccc tcaagacaaa    1020
```

<210> SEQ ID NO 6
<211> LENGTH: 1005
<212> TYPE: DNA
<213> ORGANISM: Artificial Sequence
<220> FEATURE:
<223> OTHER INFORMATION: CD64 exon-based construction (encoding SEQ ID
      NO. 3)

<400> SEQUENCE: 6

```
atgtggttct tgacaactct gctcctttgg gttccagttg atgggcaagt ggacaccaca     60
aaggcagtga tcactttgca gcctccatgg gtcagcgtgt tccaagagga aaccgtaacc    120
ttgcactgtg aggtgctcca tctgcctggg agcagctcta cacagtggtt tctcaatggc    180
acagccactc agacctcgac ccccagctac agaatcacct ctgccagtgt caatgacagt    240
ggtgaataca ggtgccagag aggtctctca gggcgaagtg acccatatca gctggaaatc    300
cacagaggct ggctactact gcaggtctcc agcagagtct tcacggaagg agaacctctg    360
gccttgaggt gtcatgcgtg aaggataag ctggtgtaca atgtgcttta ctatcgaaat    420
ggcaaagcct ttaagttttt ccactggaac tctaacctca ccattctgaa aaccaacata    480
agtcacaatg gcacctacca ttgctcaggc atgggaaagc atcgctacac atcagcagga    540
atatctgtca ctgtgaaaga gctatttcca gctccagtgc tgaatgcatc tgtgacatcc    600
ccactcctgg aggggaatct ggtcaccctg agctgtgaaa caagttgct cttgcagagg    660 cctggtttgc agctttactt ctccttctac atgggcagca gaccctgcg aggcaggaac    720 acatcctctg aataccaaat actaactgct agaagagaag actctgggtt atactggtgc    780
gaggctgcca cagaggatgg aaatgtcctt aagcgcagcc ctgagttgga gcttcaagtg    840
cttggcttct ttccacctgg gtaccaagtc tctttctgct tggtgatggt actccttttt    900
gcagtggaca caggactata tttctctgtg aagacaaaca ttcgaagctc aacaagagac    960
tggaaggacc ataaatttaa atggagaaag gaccctcaag acaaa                   1005
```

<210> SEQ ID NO 7
<211> LENGTH: 153
<212> TYPE: PRT
<213> ORGANISM: Artificial Sequence
<220> FEATURE:
<223> OTHER INFORMATION: CD28 co-stim + CD3-zeta-ITAM construct

<400> SEQUENCE: 7

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60
```

```
Leu Asn Leu Gly Arg Arg Glu Glu Tyr Asp Val Leu Asp Lys Arg Arg
 65                  70                  75                  80

Gly Arg Asp Pro Glu Met Gly Gly Lys Pro Arg Arg Lys Asn Pro Gln
                 85                  90                  95

Glu Gly Leu Phe Asn Glu Leu Gln Lys Asp Lys Met Ala Glu Ala Phe
            100                 105                 110

Ser Glu Ile Gly Met Lys Gly Glu Arg Arg Arg Gly Lys Gly His Asp
        115                 120                 125

Gly Leu Phe Gln Gly Leu Ser Thr Ala Thr Lys Asp Thr Phe Asp Ala
    130                 135                 140

Leu His Met Gln Ala Leu Pro Pro Arg
145                 150
```

<210> SEQ ID NO 8
<211> LENGTH: 219
<212> TYPE: PRT
<213> ORGANISM: Artificial Sequence
<220> FEATURE:
<223> OTHER INFORMATION: CD28 hinge + CD28 TM + CD28 co-stim + CD3-zeta-
      ITAM construct

<400> SEQUENCE: 8

```
Ile Glu Val Met Tyr Pro Pro Pro Tyr Leu Asp Asn Glu Lys Ser Asn
  1               5                  10                  15

Gly Thr Ile Ile His Val Lys Gly Lys His Leu Cys Pro Ser Pro Leu
             20                  25                  30

Phe Pro Gly Pro Ser Lys Pro Phe Trp Val Leu Val Val Val Gly Gly
         35                  40                  45

Val Leu Ala Cys Tyr Ser Leu Leu Val Thr Val Ala Phe Ile Ile Phe
 50                  55                  60

Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                 85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Glu Tyr Asp Val Leu Asp Lys
    130                 135                 140

Arg Arg Gly Arg Asp Pro Glu Met Gly Gly Lys Pro Arg Arg Lys Asn
145                 150                 155                 160

Pro Gln Glu Gly Leu Phe Asn Glu Leu Gln Lys Asp Lys Met Ala Glu
                165                 170                 175

Ala Phe Ser Glu Ile Gly Met Lys Gly Glu Arg Arg Arg Gly Lys Gly
            180                 185                 190

His Asp Gly Leu Phe Gln Gly Leu Ser Thr Ala Thr Lys Asp Thr Phe
        195                 200                 205

Asp Ala Leu His Met Gln Ala Leu Pro Pro Arg
    210                 215
```

<210> SEQ ID NO 9
<211> LENGTH: 263
<212> TYPE: PRT
<213> ORGANISM: Artificial Sequence
<220> FEATURE:
<223> OTHER INFORMATION: NKG2D TM + 2B4 + CD3-zeta construct

```
<400> SEQUENCE: 9

Ser Asn Leu Phe Val Ala Ser Trp Ile Ala Val Met Ile Ile Phe Arg
1               5                   10                  15

Ile Gly Met Ala Val Ala Ile Phe Cys Cys Phe Phe Phe Pro Ser Trp
                20                  25                  30

Arg Arg Lys Arg Lys Glu Lys Gln Ser Glu Thr Ser Pro Lys Glu Phe
            35                  40                  45

Leu Thr Ile Tyr Glu Asp Val Lys Asp Leu Lys Thr Arg Arg Asn His
        50                  55                  60

Glu Gln Glu Gln Thr Phe Pro Gly Gly Gly Ser Thr Ile Tyr Ser Met
65                  70                  75                  80

Ile Gln Ser Gln Ser Ser Ala Pro Thr Ser Gln Glu Pro Ala Tyr Thr
                85                  90                  95

Leu Tyr Ser Leu Ile Gln Pro Ser Arg Lys Ser Gly Ser Arg Lys Arg
            100                 105                 110

Asn His Ser Pro Ser Phe Asn Ser Thr Ile Tyr Glu Val Ile Gly Lys
        115                 120                 125

Ser Gln Pro Lys Ala Gln Asn Pro Ala Arg Leu Ser Arg Lys Glu Leu
130                 135                 140

Glu Asn Phe Asp Val Tyr Ser Arg Val Lys Phe Ser Arg Ser Ala Asp
145                 150                 155                 160

Ala Pro Ala Tyr Lys Gln Gly Gln Asn Gln Leu Tyr Asn Glu Leu Asn
                165                 170                 175

Leu Gly Arg Arg Glu Glu Tyr Asp Val Leu Asp Lys Arg Arg Gly Arg
            180                 185                 190

Asp Pro Glu Met Gly Gly Lys Pro Arg Arg Lys Asn Pro Gln Glu Gly
        195                 200                 205

Leu Tyr Asn Glu Leu Gln Lys Asp Lys Met Ala Glu Ala Tyr Ser Glu
210                 215                 220

Ile Gly Met Lys Gly Glu Arg Arg Arg Gly Lys Gly His Asp Gly Leu
225                 230                 235                 240

Tyr Gln Gly Leu Ser Thr Ala Thr Lys Asp Thr Tyr Asp Ala Leu His
                245                 250                 255

Met Gln Ala Leu Pro Pro Arg
            260

<210> SEQ ID NO 10
<211> LENGTH: 308
<212> TYPE: PRT
<213> ORGANISM: Artificial Sequence
<220> FEATURE:
<223> OTHER INFORMATION: CD8 hinge + NKG2D TM + 2B4 + CD3-zeta construct

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ser Asn Leu
            35                  40                  45

Phe Val Ala Ser Trp Ile Ala Val Met Ile Ile Phe Arg Ile Gly Met
        50                  55                  60

Ala Val Ala Ile Phe Cys Cys Phe Phe Phe Pro Ser Trp Arg Arg Lys
65                  70                  75                  80

Arg Lys Glu Lys Gln Ser Glu Thr Ser Pro Lys Glu Phe Leu Thr Ile
```

```
                    85                  90                  95
Tyr Glu Asp Val Lys Asp Leu Lys Thr Arg Asn His Glu Gln Glu
                100                 105                 110

Gln Thr Phe Pro Gly Gly Gly Ser Thr Ile Tyr Ser Met Ile Gln Ser
                115                 120                 125

Gln Ser Ser Ala Pro Thr Ser Gln Glu Pro Ala Tyr Thr Leu Tyr Ser
        130                 135                 140

Leu Ile Gln Pro Ser Arg Lys Ser Gly Ser Arg Lys Arg Asn His Ser
145                 150                 155                 160

Pro Ser Phe Asn Ser Thr Ile Tyr Glu Val Ile Gly Lys Ser Gln Pro
                165                 170                 175

Lys Ala Gln Asn Pro Ala Arg Leu Ser Arg Lys Glu Leu Glu Asn Phe
                180                 185                 190

Asp Val Tyr Ser Arg Val Lys Phe Ser Arg Ser Ala Asp Ala Pro Ala
                195                 200                 205

Tyr Lys Gln Gly Gln Asn Gln Leu Tyr Asn Glu Leu Asn Leu Gly Arg
        210                 215                 220

Arg Glu Glu Tyr Asp Val Leu Asp Lys Arg Arg Gly Arg Asp Pro Glu
225                 230                 235                 240

Met Gly Gly Lys Pro Arg Arg Lys Asn Pro Gln Glu Gly Leu Tyr Asn
                245                 250                 255

Glu Leu Gln Lys Asp Lys Met Ala Glu Ala Tyr Ser Glu Ile Gly Met
                260                 265                 270

Lys Gly Glu Arg Arg Arg Gly Lys Gly His Asp Gly Leu Tyr Gln Gly
                275                 280                 285

Leu Ser Thr Ala Thr Lys Asp Thr Tyr Asp Ala Leu His Met Gln Ala
        290                 295                 300

Leu Pro Pro Arg
305

<210> SEQ ID NO 11
<211> LENGTH: 414
<212> TYPE: PRT
<213> ORGANISM: Artificial Sequence
<220> FEATURE:
<223> OTHER INFORMATION: a construct mimicking trans-presentation of
      IL15 (Design 2)

<400> SEQUENCE: 11

Met Asp Trp Thr Trp Ile Leu Phe Leu Val Ala Ala Thr Arg Val
1               5                   10                  15

His Ser Gly Ile His Val Phe Ile Leu Gly Cys Phe Ser Ala Gly Leu
                20                  25                  30

Pro Lys Thr Glu Ala Asn Trp Val Asn Val Ile Ser Asp Leu Lys Lys
            35                  40                  45

Ile Glu Asp Leu Ile Gln Ser Met His Ile Asp Ala Thr Leu Tyr Thr
        50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
                100                 105                 110

Ser Asn Gly Asn Val Thr Glu Ser Gly Cys Lys Glu Cys Glu Glu Leu
            115                 120                 125
```

Glu Glu Lys Asn Ile Lys Glu Phe Leu Gln Ser Phe Val His Ile Val
130                 135                 140

Gln Met Phe Ile Asn Thr Ser Gly Gly Ser Gly Gly Gly Gly
145                 150                 155                 160

Ser Gly Gly Gly Ser Gly Gly Gly Ser Gly Gly Gly Ser Leu
            165                 170                 175

Gln Ile Thr Cys Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
            195                 200                 205

Gly Phe Lys Arg Lys Ala Gly Thr Ser Ser Leu Thr Glu Cys Val Leu
210                 215                 220

Asn Lys Ala Thr Asn Val Ala His Trp Thr Thr Pro Ser Leu Lys Cys
225                 230                 235                 240

Ile Arg Asp Pro Ala Leu Val His Gln Arg Pro Ala Pro Pro Ser Thr
            245                 250                 255

Val Thr Thr Ala Gly Val Thr Pro Gln Pro Glu Ser Leu Ser Pro Ser
            260                 265                 270

Gly Lys Glu Pro Ala Ala Ser Ser Pro Ser Ser Asn Asn Thr Ala Ala
            275                 280                 285

Thr Thr Ala Ala Ile Val Pro Gly Ser Gln Leu Met Pro Ser Lys Ser
290                 295                 300

Pro Ser Thr Gly Thr Thr Glu Ile Ser Ser His Glu Ser Ser His Gly
305                 310                 315                 320

Thr Pro Ser Gln Thr Thr Ala Lys Asn Trp Glu Leu Thr Ala Ser Ala
            325                 330                 335

Ser His Gln Pro Pro Gly Val Tyr Pro Gln Gly His Ser Asp Thr Thr
            340                 345                 350

Val Ala Ile Ser Thr Ser Thr Val Leu Leu Cys Gly Leu Ser Ala Val
            355                 360                 365

Ser Leu Leu Ala Cys Tyr Leu Lys Ser Arg Gln Thr Pro Pro Leu Ala
370                 375                 380

Ser Val Glu Met Glu Ala Met Glu Ala Leu Pro Val Thr Trp Gly Thr
385                 390                 395                 400

Ser Ser Arg Asp Glu Asp Leu Glu Asn Cys Ser His His Leu
            405                 410

<210> SEQ ID NO 12
<211> LENGTH: 1242
<212> TYPE: DNA
<213> ORGANISM: Artificial Sequence
<220> FEATURE:
<223> OTHER INFORMATION: exemplary DNA sequence encoding the amino acid
      sequence of SEQ ID NO: 11

<400> SEQUENCE: 12
atggactgga cctggattct gttcctggtc gcggctgcaa cgcgagtcca tagcggtatc        60
catgttttta ttcttgggtg tttttctgct gggctgccta agaccgaggc caactgggta       120
aatgtcatca gtgacctcaa gaaaatagaa gaccttatac aaagcatgca cattgatgct       180
actctctaca ctgagtcaga tgtacatccc tcatgcaaag tgacggccat gaatgtttc        240 ctcctcgaac ttcaagtcat atctctggaa gtggcgacg cgtccatcca cgacacggtc        300
gaaaacctga ataatactcgc taataatagt ctctcttcaa atggtaacgt aaccgagtca       360
ggttgcaaag agtgcgaaga gttggaagaa aaaaacataa aggagttcct gcaaagtttc       420

```
gtgcacattg tgcagatgtt cattaatacc tctagcggcg aggatcagg tggcggtgga    480
agcggaggtg gaggctccgg tggaggaggt agtggcggag gttctcttca ataacttgt    540
cctccaccga tgtccgtaga acatgcggat atttgggtaa atcctatag cttgtacagc    600
cgagagcggt atatctgcaa cagcggcttc aagcggaagg ccggcacaag cagcctgacc    660
gagtgcgtgc tgaacaaggc caccaacgtg gcccactgga ccacccctag cctgaagtgc    720
atcagagatc ccgccctggt gcatcagcgg cctgcccctc aagcacagt gacaacagct    780
ggcgtgaccc cccagcctga gagcctgagc ccttctggaa agagcctgc cgccagcagc    840
cccagcagca caatactgc cgccaccaca gccgccatcg tgcctggatc tcagctgatg    900
cccagcaaga gccctagcac cggcaccacc gagatcagca gccacgagtc tagccacggc    960
accccatctc agaccaccgc caagaactgg gagctgacag ccagcgcctc tcaccagcct   1020
ccaggcgtgt accctcaggg ccacagcgat accacagtgg ccatcagcac ctccaccgtg   1080
ctgctgtgtg gactgagcgc cgtgtcactg ctggcctgct acctgaagtc cagacagacc   1140
cctccactgg ccagcgtgga aatggaagcc atggaagcac tgcccgtgac ctggggcacc   1200
agctccagag atgaggatct ggaaaactgc tcccaccacc tg                     1242
```

<210> SEQ ID NO 13
<211> LENGTH: 379
<212> TYPE: PRT
<213> ORGANISM: Artificial Sequence
<220> FEATURE:
<223> OTHER INFORMATION: a construct mimicking trans-presentation of
      IL15 (Design 3)

<400> SEQUENCE: 13

```
Met Asp Trp Thr Trp Ile Leu Phe Leu Val Ala Ala Thr Arg Val
1               5                   10                  15

His Ser Gly Ile His Val Phe Ile Leu Gly Cys Phe Ser Ala Gly Leu
                20                  25                  30

Pro Lys Thr Glu Ala Asn Trp Val Asn Val Ile Ser Asp Leu Lys Lys
                35                  40                  45

Ile Glu Asp Leu Ile Gln Ser Met His Ile Asp Ala Thr Leu Tyr Thr
50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
                100                 105                 110

Ser Asn Gly Asn Val Thr Glu Ser Gly Cys Lys Glu Cys Glu Glu Leu
                115                 120                 125

Glu Glu Lys Asn Ile Lys Glu Phe Leu Gln Ser Phe Val His Ile Val
130                 135                 140

Gln Met Phe Ile Asn Thr Ser Ser Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Met Ser Val Glu His Ala Asp Ile Trp
                180                 185                 190

Val Lys Ser Tyr Ser Leu Tyr Ser Arg Glu Arg Tyr Ile Cys Asn Ser
                195                 200                 205

Gly Phe Lys Arg Lys Ala Gly Thr Ser Ser Leu Thr Glu Cys Val Leu
```

```
                210                 215                 220
Asn Lys Ala Thr Asn Val Ala His Trp Thr Thr Pro Ser Leu Lys Cys
225                 230                 235                 240

Ile Arg Asp Pro Ala Leu Val His Gln Arg Pro Ala Pro Pro Ser Thr
                245                 250                 255

Val Thr Thr Ala Gly Val Thr Pro Gln Pro Glu Ser Leu Ser Pro Ser
                260                 265                 270

Gly Lys Glu Pro Ala Ala Ser Ser Pro Ser Ser Asn Asn Thr Ala Ala
                275                 280                 285

Thr Thr Ala Ala Ile Val Pro Gly Ser Gln Leu Met Pro Ser Lys Ser
                290                 295                 300

Pro Ser Thr Gly Thr Thr Glu Ile Ser Ser His Glu Ser Ser His Gly
305                 310                 315                 320

Thr Pro Ser Gln Thr Thr Ala Lys Asn Trp Glu Leu Thr Ala Ser Ala
                325                 330                 335

Ser His Gln Pro Pro Gly Val Tyr Pro Gln Gly His Ser Asp Thr Thr
                340                 345                 350

Val Ala Ile Ser Thr Ser Thr Val Leu Leu Cys Gly Leu Ser Ala Val
                355                 360                 365

Ser Leu Leu Ala Cys Tyr Leu Lys Ser Arg Gln
                370                 375

<210> SEQ ID NO 14
<211> LENGTH: 1140
<212> TYPE: DNA
<213> ORGANISM: Artificial Sequence
<220> FEATURE:
<223> OTHER INFORMATION: exemplary nucleic acid sequence encoding the
      amino acid sequence of SEQ ID NO: 13

<400> SEQUENCE: 14
atggactgga cctggattct gttcctggtc gcggctgcaa cgcgagtcca tagcggtatc     60
catgttttta ttcttgggtg tttttctgct gggctgccta agaccgaggc caactgggta    120
aatgtcatca gtgacctcaa gaaaatagaa gaccttatac aaagcatgca cattgatgct    180
actctctaca ctgagtcaga tgtacatccc tcatgcaaag tgacggccat gaaatgtttc    240
ctcctcgaac ttcaagtcat atctctggaa agtggcgacg cgtccatcca cgacacggtc    300
gaaaacctga taatactcgc taataatagt ctctcttcaa atggtaacgt aaccgagtca    360
ggttgcaaag agtgcgaaga gttggaagaa aaaacataa aggagttcct gcaaagtttc    420
gtgcacattg tgcagatgtt cattaatacc tctagcggcg aggatcagg tggcggtgga    480 agcggaggtg gaggctccgg tggaggaggt agtggcggag ttctcttca ataacttgt     540 cctccaccga tgtccgtaga acatgcggat atttgggtaa atcctatag cttgtacagc    600 cgagagcggt atatctgcaa cagcggcttc aagcggaagg ccggcacaag cagcctgacc    660
gagtgcgtgc tgaacaaggc caccaacgtg gcccactgga ccaccccctag cctgaagtgc    720 atcagagatc ccgccctggt gcatcagcgg cctgccctc aagcacagt gacaacagct    780 ggcgtgaccc ccagcctga gagcctgagc ccttctggaa aagagcctgc cgccagcagc    840
cccagcagca caatactgc cgccaccaca gccgccatcg tgcctggatc tcagctgatg    900
cccagcaaga gcctagcac cggcaccacc gagatcagca gccacgagtc tagccacggc    960 acccatctc agaccaccgc caagaactgg gagctgacag ccagcgcctc tcaccagcct   1020
ccaggcgtgt accctcaggg ccacagcgat accacagtgg ccatcagcac ctccaccgtg   1080
```

```
ctgctgtgtg gactgagcgc cgtgtcactg ctggcctgct acctgaagtc cagacagtga    1140
```

<210> SEQ ID NO 15
<211> LENGTH: 242
<212> TYPE: PRT
<213> ORGANISM: Artificial Sequence
<220> FEATURE:
<223> OTHER INFORMATION: a construct mimicking trans-presentation of
      IL15 (Design 4)

<400> SEQUENCE: 15

Met Asp Trp Thr Trp Ile Leu Phe Leu Val Ala Ala Thr Arg Val
1               5                   10                  15

His Ser Gly Ile His Val Phe Ile Leu Gly Cys Phe Ser Ala Gly Leu
            20                  25                  30

Pro Lys Thr Glu Ala Asn Trp Val Asn Val Ile Ser Asp Leu Lys Lys
        35                  40                  45

Ile Glu Asp Leu Ile Gln Ser Met His Ile Asp Ala Thr Leu Tyr Thr
    50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
            100                 105                 110

Ser Asn Gly Asn Val Thr Glu Ser Gly Cys Lys Glu Cys Glu Glu Leu
        115                 120                 125

Glu Glu Lys Asn Ile Lys Glu Phe Leu Gln Ser Phe Val His Ile Val
130                 135                 140

Gln Met Phe Ile Asn Thr Ser Ser Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
        195                 200                 205

Gly Phe Lys Arg Lys Ala Gly Thr Ser Ser Leu Thr Glu Cys Val Leu
    210                 215                 220

Asn Lys Ala Thr Asn Val Ala His Trp Thr Thr Pro Ser Leu Lys Cys
225                 230                 235                 240

Ile Arg

<210> SEQ ID NO 16
<211> LENGTH: 726
<212> TYPE: DNA
<213> ORGANISM: Artificial Sequence
<220> FEATURE:
<223> OTHER INFORMATION: exemplary nucleic acid sequence encoding the
      amino acid sequence of SEQ ID NO: 15

<400> SEQUENCE: 16

```
atggactgga cctggattct gttcctggtc gcggctgcaa cgcgagtcca tagcggtatc    60
catgttttta ttcttgggtg ttttttctgct gggctgccta agaccgaggc caactgggta   120
aatgtcatca gtgacctcaa gaaaatagaa gaccttatac aaagcatgca cattgatgct   180
actctctaca ctgagtcaga tgtacatccc tcatgcaaag tgacggccat gaaatgtttc   240
```

-continued

| | | | | | |
|---|---|---|---|---|---|
| ctcctcgaac | ttcaagtcat | atctctggaa | agtggcgacg | cgtccatcca | cgacacggtc | 300 |
| gaaaacctga | taatactcgc | taataatagt | ctctcttcaa | atggtaacgt | aaccgagtca | 360 |
| ggttgcaaag | agtgcgaaga | gttggaagaa | aaaaacataa | aggagttcct | gcaaagtttc | 420 |
| gtgcacattg | tgcagatgtt | cattaatacc | tctagcggcg | gaggatcagg | tggcggtgga | 480 |
| agcggaggtg | gaggctccgg | tggaggaggt | agtggcggag | gttctcttca | aataacttgt | 540 |
| cctccaccga | tgtccgtaga | acatgcggat | atttgggtaa | aatcctatag | cttgtacagc | 600 |
| cgagagcggt | atatctgcaa | cagcggcttc | aagcggaagg | ccggcacaag | cagcctgacc | 660 |
| gagtgcgtgc | tgaacaaggc | caccaacgtg | gcccactgga | ccaccctag | cctgaagtgc | 720 |
| atcaga | | | | | | 726 |

COMBINING iPSC DERIVED EFFECTOR CELL TYPES FOR IMMUNOTHERAPY USE

RELATED APPLICATION

This application claims priority to U.S. Provisional Application Ser. No. 63/041,672, filed Jun. 19, 2020, the disclosure of which is hereby incorporated by reference in its entirety.

REFERENCE TO SEQUENCE LISTING SUBMITTED ELECTRONICALLY

This application incorporates by reference a Computer Readable Form (CRF) of a Sequence Listing in ASCII text format submitted with this application, entitled 056932-527001WO_SEQ_LISTING.txt, which was created on Jun. 18, 2021, and is 36,268 bytes in size.

FIELD OF THE INVENTION

The present disclosure is broadly concerned with the field of off-the-shelf immunocellular products. More particularly, the present disclosure is concerned with the strategies for developing multifunctional effector cells capable of delivering therapeutically relevant properties in vivo. The cell products developed under the present disclosure address critical limitations of patient-sourced cell therapies.

BACKGROUND OF THE INVENTION

The field of adoptive cell therapy is currently focused on using patient- and donor-sourced cells, which makes it particularly difficult to achieve consistent manufacturing of cancer immunotherapies and to deliver therapies to all patients who may benefit. There is also the need to improve the efficacy and persistence of adoptively transferred lymphocytes to promote favorable patient outcome. Lymphocytes, such as T cells and natural killer (NK) cells, are potent anti-tumor effectors that play an important role in innate and adaptive immunity. However, the use of these immune cells for adoptive cell therapies remains challenging and has unmet needs for improvement. Therefore, there remain significant opportunities to harness the full potential of T and NK cells, or other lymphocytes in adoptive immunotherapy.

SUMMARY OF THE INVENTION

There is a need for functionally improved effector cells that address issues ranging from response rate, cell exhaustion, loss of transfused cells (survival and/or persistence), tumor escape through target loss or lineage switch, tumor targeting precision, off-target toxicity, off-tumor effect, to efficacy against solid tumors, i.e., tumor microenvironment and related immune suppression, recruiting, trafficking and infiltration.

It is an object of the present invention to provide methods and compositions to generate derivative non-pluripotent cells differentiated from a single cell derived iPSC (induced pluripotent stem cell) clonal line, which iPSC line comprises one or several genetic modifications in its genome. Said one or several genetic modifications include DNA insertion, deletion, and substitution, and which modifications are retained and remain functional in subsequently derived cells after differentiation, expansion, passaging and/or transplantation.

The iPSC-derived non-pluripotent cells of the present application include, but not limited to, CD34 cells, hemogenic endothelium cells, HSCs (hematopoietic stem and progenitor cells), hematopoietic multipotent progenitor cells, T cell progenitors, NK cell progenitors, T cells, NKT cells, NK cells, and B cells. The iPSC-derived non-pluripotent cells of the present application comprise one or several genetic modifications in their genome through differentiation from an iPSC comprising the same genetic modifications. The engineered clonal iPSC differentiation strategy for obtaining genetically engineered derivative cells requires that the developmental potential of the iPSC in a directed differentiation is not adversely impacted by the engineered modality in the iPSC, and also that the engineered modality functions as intended in the derivative cell. Further, this strategy overcomes the present barrier in engineering primary lymphocytes, such as T cells or NK cells obtained from peripheral blood, as such cells are difficult to engineer, with engineering of such cells often lacking reproducibility and uniformity, resulting in cells exhibiting poor cell persistence with high cell death and low cell expansion. Moreover, this strategy avoids production of a heterogenous effector cell population otherwise obtained using primary cell sources which are heterogenous to start with.

Some aspects of the present invention provide genome-engineered iPSCs obtained using a method comprising (I), (II) or (III), reflecting a strategy of genomic engineering subsequently to, simultaneously with, and prior to the reprogramming process, respectively:

(I): genetically engineering iPSCs by one or both of (i) and (ii), in any order: (i) introducing into iPSCs one or more construct(s) to allow targeted integration at selected site(s); (ii) (a) introducing into iPSCs one or more double-stranded break(s) at selected site(s) using one or more endonucleases capable of selected site recognition; and (b) culturing the iPSCs of step (I)(ii)(a) to allow endogenous DNA repair to generate targeted in/dels at the selected site(s); thereby obtaining genome-engineered iPSCs capable of differentiation into partially or fully differentiated cells.

(II): genetically engineering and reprogramming non-pluripotent cells to obtain the genome-engineered iPSCs by: (i) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate reprogramming of the non-pluripotent cells; and (ii) introducing into the reprogramming non-pluripotent cells during the reprogramming of step (II)(i) one or both of (a) and (b), in any order: (a) one or more construct(s) to allow targeted integration at selected site(s); (b) one or more double-stranded break(s) at selected site(s) using at least one endonuclease capable of selected site recognition, then the cells of step (II)(ii)(b) are cultured to allow endogenous DNA repair to generate targeted in/dels at the selected site(s); as such the obtained genome-engineered iPSCs comprise at least one functional targeted genomic edit, and said genome-engineered iPSCs are capable of differentiation into partially or fully differentiated cells.

(III): genetically engineering non-pluripotent cells for reprogramming to obtain genome-engineered iPSCs by (i) and (ii): (i) introducing into non-pluripotent cells one or both of (a) and (b), in any order: (a) one or more constructs to allow targeted integration at selected site(s); (b) one or more double-stranded breaks at selected site(s) using at least one endonuclease capable of selected site recognition, wherein the cells of step (III)(i)(b) are cultured to allow endogenous DNA repair to generate targeted in/dels at the selected site(s); and (ii) contacting the cells of step (III)(i) with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted editing at the selected site(s); thereby obtaining genome-engineered iPSCs comprising at least one functional targeted genomic edit, and said genome-engineered iPSCs are capable of being differentiated into partially differentiated cells or fully-differentiated cells.

In one embodiment of the above method, the at least one targeted genomic edit(s) at one or more selected site(s) comprises insertion of one or more exogenous polynucleotides encoding safety switch proteins, targeting modalities, receptors, signaling molecules, transcription factors, pharmaceutically active proteins and peptides, drug target candidates, or proteins promoting engraftment, trafficking, homing, viability, self-renewal, persistence, and/or survival of the genome-engineered iPSCs or derivative cells therefrom. In some embodiments, the exogenous polynucleotides for insertion are operatively linked to (1) one or more exogenous promoters comprising CMV, EF1α, PGK, CAG, UBC, or other constitutive, inducible, temporal-, tissue-, or cell type-specific promoters; or (2) one or more endogenous promoters comprised in the selected site(s) comprising AAVS1, CCR5, ROSA26, collagen, HTRP, H11, beta-2 microglobulin, GAPDH, TCR or RUNX1, or other locus meeting the criteria of a genome safe harbor. In some embodiments, the genome-engineered iPSCs generated using the above method comprise one or more different exogenous polynucleotides encoding proteins comprising caspase, thymidine kinase, cytosine deaminase, modified EGFR, or B-cell CD20, wherein when the genome-engineered iPSCs comprise two or more suicide genes, the suicide genes are integrated in different safe harbor loci comprising AAVS1, CCR5, ROSA26, collagen, HTRP, H11, H11, beta-2 microglobulin, GAPDH, TCR or RUNX1. In some embodiments, the exogenous polynucleotide encodes a partial or full peptide of IL2, IL4, IL6, IL7, IL9, IL10, IL11, IL12, IL15, IL18, IL21, and/or respective receptors thereof. In some embodiments, the partial or full peptide of IL2, IL4, IL6, IL7, IL9, IL10, IL11, IL12, IL15, IL18, IL21, and/or respective receptors thereof encoded by the exogenous polynucleotide is in the form of a fusion protein.

In some other embodiments, the genome-engineered iPSCs generated using the method provided herein comprise an in/del at one or more endogenous genes associated with targeting modalities, receptors, signaling molecules, transcription factors, drug target candidates, immune response regulation and modulation, or proteins suppressing engraftment, trafficking, homing, viability, self-renewal, persistence, and/or survival of the iPSCs or derivative cells therefrom. In some embodiments, the endogenous gene for disruption comprises at least one of B2M, TAP1, TAP2, Tapasin, NLRC5, PD1, LAGS, TIM3, RFXANK, CIITA, RFX5, RFXAP, and any gene in the chromosome 6p21 region.

In yet some other embodiments, the genome-engineered iPSCs generated using the method provided herein comprise an exogenous polynucleotide encoding a caspase at the AAVS1 locus, and a thymidine kinase encoding exogenous polynucleotide at the H11 locus.

In still some other embodiments, approach (I), (II) and/or (III) further comprises: contacting the genome-engineered iPSCs with a small molecule composition comprising a MEK inhibitor, a GSK3 inhibitor and a ROCK inhibitor, to maintain the pluripotency of the obtained genome-engineered iPSCs. In one embodiment, the obtained genome-engineered iPSCs comprising at least one targeted genomic edit are functional, are differentiation potent, and are capable of differentiating into non-pluripotent cells comprising the same functional genomic edit.

Accordingly, in one aspect, the present invention also provides a composition comprising two or more synthetic cell populations, wherein the composition comprises: (i) a first synthetic cell population comprising iPSC-derived NK cells, wherein the iPSC-derived NK cells comprise: (a) an exogenous CD16 or a variant thereof; and (b) one or both of a first chimeric antigen receptor (CAR), and a partial or full-length peptide of a cell surface expressed exogenous cytokine and/or a receptor thereof; and (ii) a second synthetic cell population comprising iPSC-derived T cells, wherein the iPSC-derived T cells comprise: at least a second chimeric antigen receptor (CAR), and wherein the second CAR is expressed under the control of an endogenous promoter of a TCR locus. In various embodiments, the exogenous CD16 or variant thereof is a high affinity non-cleavable CD16 (hnCD16); or the exogenous CD16 or a variant thereof comprises at least one of: (a) F176V and S197P in ectodomain domain of CD16; (b) a full or partial ectodomain originated from CD64; (c) a non-native (or non-CD16) transmembrane domain; (d) a non-native (or non-CD16) intracellular domain; (e) a non-native (or non-CD16) signaling domain; (f) a non-native stimulatory domain; or (g) transmembrane, signaling, and stimulatory domains that are not originated from CD16, and are originated from a same or different polypeptide. In certain embodiments of the composition, (a) the non-native transmembrane domain is derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide; (b) the non-native stimulatory domain is derived from CD27, CD28, 4-1BB, OX40, ICOS, PD-1, LAG-3, 2B4, BMA, DAP10, DAP12, CTLA-4, or NKG2D polypeptide; (c) the non-native signaling domain is derived from CD3ζ, 2B4, DAP10, DAP12, DNAM1, CD137 (4-1BB), IL21, IL7, IL12, IL15, NKp30, NKp44, NKp46, NKG2C, or NKG2D polypeptide; or d) the non-native transmembrane domain is derived from NKG2D, the non-native stimulatory domain is derived from 2B4, and the non-native signaling domain is derived from CD3ζ.

In various embodiments of the composition, the the first CAR and the second CAR are the same or are different in targeting specificity, and the first CAR or the second CAR is: (i) T cell specific or NK cell specific; (ii) a bi-specific antigen binding CAR; (iii) a switchable CAR; (iv) a dimerized CAR; (v) a split CAR; (vi) a multi-chain CAR; (vii) an inducible CAR; (viii) co-expressed with another CAR; (ix) co-expressed with a partial or full length peptide of a cell surface expressed exogenous cytokine and/or a receptor thereof, optionally in separate constructs or in a bi-cistronic construct; (x) co-expressed with a checkpoint inhibitor, optionally in separate constructs or in a bi-cistronic construct; (xi) specific to CD19 or BCMA; and/or (xii) specific to any one of ADGRE2, carbonic anhydrase IX (CAIX), CCRI, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein2 (EGP 2), epithelial glycoprotein-40 (EGP-40), epithelial cell adhesion molecule (Ep-CAM), EGFRvIII, receptor tyrosine-protein kinases erb-B2, 3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen. In some embodiments, the partial or full-length peptide of a cell surface expressed exogenous cytokine and/or a receptor thereof: (a) comprises at least one of IL2, IL4, IL6, IL7, IL9, IL10, IL11, IL12, IL15, IL18, IL21, and respective receptor thereof; or (b) comprises at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15β; (vi) a fusion protein of IL15 and common receptor γC, wherein the common receptor γC is native or modified; and (vii) a homodimer of IL15β; wherein any one of (i)-(vii) can be co-expressed with a CAR in separate constructs or in a bi-cistronic construct, and optionally, (c) is transiently expressed.

In some embodiments of the composition, the iPSC-derived NK cells or the iPSC-derived T cells further comprise one or more of: (i) HLA-I deficiency; (ii) HLA-II deficiency; (iii) introduced expression of HLA-G or non-cleavable HLA-G; (iv) at least one of lig−, inR+, cs-CD3+, En+, and Ab+; wherein (1) lig− is negative in an expressed alloantigen; (2) inR+ is positive in an expressed inactivation-CAR corresponding to the negative alloantigen; (3) cs-CD3+ is positive in cell surface expressed CD3; (4) En+ is positive in at least one expressed engager, wherein the engager comprises a bi-specific T cell engager (BiTE), or a tri-specific killer cell engager (TriKE); and (5) Ab+ is positive in at least one expressed antibody or checkpoint inhibitor; (v) deletion or reduced expression in at least one of TAP1, TAP2, Tapasin, NLRC5, PD1, LAG3, TIM3, RFXANK, RFX5, RAG1, RFXAP, and any gene in the chromosome 6p21 region; and (vi) introduced or increased expression in at least one of HLA-E, HLA-G, 41BBL, CD4, CD8, CD16, CD47, CD113, CD131, CD137, CD80, PDL1, $A_{2A}R$, TCR, Fc receptor, and surface triggering receptor for coupling with bi- or multi-specific or universal engagers. In certain embodiments, (i) the alloantigen comprises CD40L, OX40, or 4-1BB; (ii) the inactivation-CAR comprises CD40L-CAR, OX40-CAR, or 4-1BB-CAR; (iii) the BiTE or the TriKE recognizes (a) an immune cell surface molecule comprising CD3, CD28, CD5, CD16, NKG2D, CD64, CD32, CD89, NKG2C, or a chimeric Fc receptor thereof; and (b) a tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1; (iv) the BiTE comprises CD3-CD19, CD16-CD30, CD64-CD30, CD16-BCMA, CD64-BCMA, or CD3-CD33; (v) the TriKE comprises CD16-IL15-EPCAM, CD64-IL15-EPCAM, CD16-IL15-CD33, CD64-IL15-CD33, or NKG2C-IL15-CD33; (vi) the antibody comprises an anti-CD20, anti-HER2, anti-CD52, anti-EGFR, anti-CD123, anti-GD2, anti-PDL1, or anti-CD38 antibody; or (vii) the checkpoint inhibitor comprises (a) an antagonist to a checkpoint molecule comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one of atezolizumab, avelumab, durvalumab, ipilimumab, IPH4102, IPH43, IPH33, lirimumab, monalizumab, nivolumab, pembrolizumab, and their derivatives or functional equivalents; or (c) one of atezolizumab, nivolumab, and pembrolizumab.

In various embodiments of the composition, the iPSC-derived NK cells or the iPSC-derived T cells comprise: (i) one or more exogenous polynucleotides integrated in one desired integration site; or (ii) more than two exogenous polynucleotides integrated in different desired integration sites. In certain embodiments, the desired integration site comprises at least one of AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD40L, CD44, CD54, CD56, CD58, CD69, CD71, OX40, 4-1BB, CIS, CBL-B, SOCS2, PD1, CTLA4, LAGS, TIM3, and TIGIT. In other embodiments, the desired integration site comprises TCR α or β constant region, CD25, CD38, CD40L, CD44, CD54, CD58, CD69, CD71, OX40 or 4-1BB; and optionally, wherein the TCRα or TCRβ, CD25, CD38, CD40L, CD44, CD54, CD58, CD69, CD71, OX40 or 4-1BB is knocked out as a result of integrating said one or more exogenous polynucleotides at the respective integration site.

In various embodiments of the composition, the iPSC-derived NK cells or the iPSC-derived T cells have at least one of the following characteristics comprising: (i) improved persistency and/or survival, (ii) increased resistance to native immune cells, (iii) increased cytotoxicity, (iv) improved tumor penetration, (v) enhanced or acquired ADCC. (vi) enhanced ability in migrating, and/or activating or recruiting bystander immune cells to tumor sites, (vii) enhanced ability to reduce tumor immunosuppression, and (viii) improved ability in rescuing tumor antigen escape, in comparison to its native counterpart cell obtained from peripheral blood, umbilical cord blood, or any other donor tissues. In various embodiments of the composition, the iPSC-derived NK cells or the iPSC-derived T cells comprise longer telomeres in comparison to their respective native counterpart cell obtained from peripheral blood, umbilical cord blood, or any other donor tissues. In various embodiments of the composition, the first synthetic cell population or the second synthetic cell population is modulated ex vivo. In certain embodiments, the modulated first synthetic cell population comprising iPSC-derived NK cells comprises an increased number or ratio of type I NKT cells, and/or adaptive NK cells, as compared to the first synthetic cell population without being modulated; or wherein the second modulated synthetic cell population comprising iPSC-derived T cells comprises an increased number or ratio of naïve T cells, stem cell memory T cells, and/or central memory T cells, as compared to the second synthetic cell population without being modulated.

In various embodiments of the composition, (i) the iPSC-derived NK cells and the iPSC-derived T cells are in a ratio ranging from 100:1 to 1:100; (ii) the composition further comprises one or more additional cell populations; or (iii) the composition further comprises one or more therapeutic agents. In certain embodiments, the additional cell population comprises regulatory cells. In some embodiments where the additional cell population comprises regulatory cells, the regulatory cells are iPSC-derived immune regulatory cells or myeloid derived suppressor cells (MDSCs). In some embodiments where the composition further comprises one or more therapeutic agents, the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). In some embodiments where the one or more therapeutic agents comprise a checkpoint inhibitor, the checkpoint inhibitor comprises: (a) one or more antagonist checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one or more of atezolizumab, avelumab, durvalumab, ipilimumab, IPH4102, IPH43, IPH33, lirimumab, monalizumab, nivolumab, pembrolizumab, and their derivatives or functional equivalents; or (c) at least one of atezolizumab, nivolumab, and pembrolizumab. In some embodiments where the one or more therapeutic agents comprise an antibody, the antibody comprises: (a) anti-CD20, anti-HER2, anti-CD52, anti-EGFR, anti-CD123, anti-GD2, anti-PDL1, and/or anti-CD38 antibody; (b) one or more of retuximab, veltuzumab, ofatumumab, ublituximab, ocaratuzumab, obinutuzumab, trastuzumab, pertuzumab, alemtuzumab, certuximab, dinutuximab, avelumab, daratumumab, isatuximab, MOR202, 7G3, CSL362, elotuzumab and their humanized or Fc modified variants or fragments and their functional equivalents and biosimilars; or (c) daratumumab.

In various embodiments of the composition, the first synthetic cell population and the second synthetic cell population are separate populations or are combined into a mixed population.

In another aspect, the present invention provides for therapeutic use of the compositions herein by introducing the composition to a subject suitable for adoptive cell therapy, wherein the subject has an autoimmune disorder; a hematological malignancy; a solid tumor; cancer, or a virus infection.

In yet another aspect, the present invention provides a method of improving tumor killing and/or clearance by a population of CAR-T cells comprising: providing a synthetic cell population comprising iPSC-derived NK cells to the population of CAR-T cells to obtain a combined cell population, wherein the iPSC-derived NK cells comprise: (a) an exogenous CD16 or a variant thereof; and (b) one or both of a first chimeric antigen receptor (CAR), and a partial or full length peptide of a cell surface expressed exogenous cytokine and/or a receptor thereof; and wherein the first CAR of the iPSC-derived NK cells comprise a CAR targeting specificity that is same or different from that of the CAR-T cell. In various embodiments the CAR-T cells refer to CAR bearing T cells from any source. For example, the T cells may be primary cells or may be cells from a line cell, may be autologous or allogeneic cells, and may be differentiated from iPSC.

In some embodiments of the method of improving tumor killing and/or clearance, the combined cell population comprises cells having: (i) improved persistency and/or survival, (ii) increased resistance to native immune cells, (iii) increased cytotoxicity, (iv) improved tumor penetration, (v) enhanced or acquired ADCC. (vi) enhanced ability in migrating, and/or activating or recruiting bystander immune cells to tumor sites, (vii) enhanced ability to reduce tumor immunosuppression, and (viii) improved ability in rescuing tumor antigen escape, in comparison to tumor killing and/or clearance by the population of CAR-T cells only without the combination of the iPSC-derived NK cell. In some embodiments of the method, the exogenous CD16 or variant thereof is a high affinity non-cleavable exogenous CD16 (hnCD16); or wherein the exogenous CD16 or variant thereof comprises at least one of: (a) F176V and S197P in ectodomain domain of CD16; (b) a full or partial ectodomain originated from CD64; (c) a non-native (or non-CD16) transmembrane domain; (d) a non-native (or non-CD16) intracellular domain; (e) a non-native (or non-CD16) signaling domain; (f) a non-native stimulatory domain; and (g) transmembrane, signaling, and stimulatory domains that are not originated from CD16, and are originated from a same or different polypeptide.

In some embodiments of the method, (a) the non-native transmembrane domain is derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide; (b) the non-native stimulatory domain is derived from CD27, CD28, 4-1BB, OX40, ICOS, PD-1, LAG-3, 2B4, BTLA, DAP10, DAP12, CTLA-4, or NKG2D polypeptide; (c) the non-native signaling domain is derived from CD3ζ, 2B4, DAP10, DAP12, DNAM1, CD137 (4-1BB), IL21, IL7, IL12, IL15, NKp30, NKp44, NKp46, NKG2C, or NKG2D polypeptide; or (d) the non-native transmembrane domain is derived from NKG2D, the non-native stimulatory domain is derived from 2B4, and the non-native signaling domain is derived from CD3ζ. In other embodiments of the method, the partial or full length peptide of a cell surface expressed exogenous cytokine and/or a receptor thereof: (a) comprises at least one of IL2, IL4, IL6, IL7, IL9, IL10, IL11, IL12, IL15, IL18, IL21, and/or respective receptors thereof; or (b) comprises at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15β; (vi) a fusion protein of IL15 and common receptor γC, wherein the common receptor γC is native or modified; and (vii) a homodimer of IL15β; wherein any one of (i)-(vii) can be co-expressed with a CAR in separate constructs or in a bi-cistronic construct; and optionally, (c) is transiently expressed. In some embodiments of the method, the CAR-T cells are differentiated from an engineered iPSC, and/or wherein the CAR-T cells comprise a CAR having targeting specificity to any one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein2 (EGP-2), epithelial glycoprotein-40 (EGP-40), epithelial cell adhesion molecule (Ep-CAM), EGFRvIII, receptor tyrosine-protein kinases erb-B2, 3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen.

In some embodiments of the method of improving tumor killing and/or clearance, the iPSC-derived NK cells and/or the CAR-T cells further comprise one or more of: (i) HLA-I deficiency; (ii) HLA-II deficiency; (iii) introduced expression of HLA-G or non-cleavable HLA-G; (iv) at least one of lig−, inR+, cs-CD3+, En+, and Ab+; wherein (1) lig− is negative in an expressed alloantigen; (2) inR+ is positive in an expressed inactivation-CAR corresponding to the negative alloantigen; (3) cs-CD3+ is positive in cell surface expressed CD3; (4) En+ is positive in at least one expressed engager, wherein the engager comprises a bi-specific T cell engager (BiTE), or a tri-specific killer cell engager (TriKE); and (5) Ab+ is positive in at least one expressed antibody or checkpoint inhibitor; (v) deletion or reduced expression in at least one of B2M, CIITA, TAP1, TAP2, Tapasin, NLRC5, PD1, LAG3, TIM3, RFXANK, RFX5, RAG1, RFXAP, and any gene in the chromosome 6p21 region; and (vi) introduced or increased expression in at least one of HLA-E, HLA-G, 4-1BBL, CD4, CD8, CD16, CD47, CD113, CD131, CD137, CD80, PDL1, $A_{2A}R$, TCR, Fc receptor, and surface triggering receptor for coupling with bi- or multi-specific or universal engagers. In certain embodiments, (i) the alloantigen comprises CD40L, OX40, or 4-1BB; (ii) the inactivation-CAR comprises CD40L-CAR, OX40-CAR, or 4-1BB-CAR; (iii) the BiTE or the TriKE recognizes (a) an immune cell surface molecule comprising CD3, CD28, CD5, CD16, NKG2D, CD64, CD32, CD89, NKG2C, or a chimeric Fc receptor thereof; and (b) a tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1; (iv) the BiTE comprises CD3-CD19, CD16-CD30, CD64-CD30, CD16-BCMA, CD64-BCMA, or CD3-CD33; (v) the TriKE comprises CD16-IL15-EPCAM, CD64-IL15-EPCAM, CD16-IL15-CD33, CD64-IL15-CD33, or NKG2C-IL15-CD33; (vi) the antibody comprises an anti-CD20, anti-HER2, anti-CD52, anti-EGFR, anti-CD123, anti-GD2, anti-PDL1, or anti-CD38 antibody; or (vii) the checkpoint inhibitor comprises (a) an antagonist to a checkpoint molecule comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one of atezolizumab, avelumab, durvalumab, ipilimumab, IPH4102, IPH43, IPH33, lirimumab, monalizumab, nivolumab, pembrolizumab, and their derivatives or functional equivalents; or (c) one of atezolizumab, nivolumab, and pembrolizumab.

In some embodiments of the method of improving tumor killing and/or clearance, the method further comprises providing one or more therapeutic agent, wherein the one or more therapeutic agents comprise a peptide, a cytokine, a checkpoint inhibitor, an antibody, a mitogen, a growth factor, a small RNA, a dsRNA (double stranded RNA), mononuclear blood cells, feeder cells, feeder cell components or replacement factors thereof, a vector comprising one or more polynucleic acids of interest, a chemotherapeutic agent or a radioactive moiety, or an immunomodulatory drug (IMiD). In some embodiments of the method of improving tumor killing and/or clearance where the one or more therapeutic agents comprise a checkpoint inhibitor, the the checkpoint inhibitor comprises: (a) one or more antagonist checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one or more of atezolizumab, avelumab, durvalumab, ipilimumab, IPH4102, IPH43, IPH33, lirimumab, monalizumab, nivolumab, pembrolizumab, and their derivatives or functional equivalents; or (c) at least one of atezolizumab, nivolumab, and pembrolizumab. In some embodiments of the method of improving tumor killing and/or clearance where the one or more therapeutic agents comprise an antibody, the antibody comprises: (a) anti-CD20, anti-HER2, anti-CD52, anti-EGFR, anti-CD123, anti-GD2, anti-PDL1, and/or anti-CD38 antibody; (b) one or more of retuximab, veltuzumab, ofatumumab, ublituximab, ocaratuzumab, obinutuzumab, trastuzumab, pertuzumab, alemtuzumab, certuximab, dinutuximab, avelumab, daratumumab, isatuximab, MOR202, 7G3, CSL362, elotuzumab, and their humanized or Fc modified variants or fragments and their functional equivalents and biosimilars; or (c) daratumumab.

In another aspect, the present invention provides a method of treating a subject using the compositions described herein, wherein the method comprises: (i) administering the first synthetic cell population that comprises iPSC-derived NK cells to the subject, wherein the iPSC-derived NK cells comprise: (a) an exogenous CD16 or a variant thereof; and (b) one or both of a first chimeric antigen receptor (CAR), and a partial or full length peptide of a cell surface expressed exogenous cytokine or a receptor thereof; and (ii) administering the second synthetic cell population that comprises iPSC-derived T cells to the subject, wherein the iPSC-derived T cells comprise: at least a second chimeric antigen receptor (CAR), wherein the second CAR is expressed under the control of an endogenous promoter of a TCR locus, and wherein the first CAR and the second CAR are same or different in targeting specificity. In certain embodiments, the subject has a condition comprising an autoimmune disorder; a hematological malignancy; a solid tumor; cancer, or a virus infection; and/or wherein the method provides enhanced improvement of the condition in comparison using the first or the second synthetic cell population alone. In some embodiments, the first synthetic cell population and the second synthetic cell population are administrated concurrently, or sequentially in any order. In various embodiments of the method of treating a subject using the compositions described herein, the the first synthetic cell population and the second synthetic cell population are separate populations or are combined into a mixed population prior to administration to the subject. In some embodiments of the method of treating a subject using the compositions described herein, the method further comprises administering one or more therapeutic agents; and/or administering an additional population of cells, wherein the one or more therapeutic agents and/or the additional population of cells are administered concurrently or sequentially with either the first synthetic cell population or the second synthetic cell population. In some embodiments, where the method includes administering an additional population of cells, the additional cell population comprises regulatory cells. In some embodiments, the regulatory cells are iPSC-derived immune regulatory cells or myeloid derived suppressor cells (MDSCs). In some embodiments, where the method includes administering on or more therapeutic agents, the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

In various embodiments of method of treating a subject using the compositions described herein, the method further comprises administering to the subject: (i) a BiTE or a TriKE specific to (a) an immune cell surface molecule comprising CD3, CD28, CD5, CD16, NKG2D, CD64, CD32, CD89, NKG2C, or a chimeric Fc receptor thereof; and (b) a tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1; (ii) a BiTE comprising CD3-CD19, CD16-CD30, CD64-CD30, CD16-BCMA, CD64-BCMA, or CD3-CD33; (iii) a TriKE comprising CD16-IL15-EPCAM, CD64-IL15-EPCAM, CD16-IL15-CD33, CD64-IL15-CD33, or NKG2C-IL15-CD33; (iv) an antibody comprising an anti-CD20, anti-HER2, anti-CD52, anti-EGFR, anti-CD123, anti-GD2, anti-PDL1, or anti-CD38 antibody; or (v) a checkpoint inhibitor comprising (a) an antagonist to a checkpoint molecule comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one of atezolizumab, avelumab, durvalumab, ipilimumab, IPH4102, IPH43, IPH33, lirimumab, monalizumab, nivolumab, pembrolizumab, and their derivatives or functional equivalents; or (c) one of atezolizumab, nivolumab, and pembrolizumab.

In another aspect, the present invention provides a method of manufacturing the compositions described herein, the method comprising: (i) differentiating a first genetically engineered iPSC to obtain a first synthetic cell population comprising iPSC-derived NK cells, wherein the first iPSC comprises a polynucleotide encoding (a) an exogenous CD16 or a variant thereof; and (b) one or both of a first chimeric antigen receptor (CAR), and a partial or full length peptide of a cell surface expressed exogenous cytokine and/or a receptor thereof, wherein the iPSC-derived NK cells comprise (a) and (b); and (ii) differentiating a second genetically engineered iPSC to obtain a second synthetic cell population comprising iPSC-derived T cells, wherein the second iPSC comprises a polynucleotide encoding at least a second chimeric antigen receptor (CAR), wherein the second CAR is expressed under the control of an endogenous promoter of a TCR locus, and wherein the iPSC-derived T cells comprise the second CAR, thereby manufacturing the compositions described herein. In some embodiments of the method of manufacturing, the exogenous CD16 or variant thereof is a high affinity non-cleavable exogenous CD16 (hnCD16); or wherein the exogenous CD16 or variant thereof comprises at least one of: (a) F176V and S197P in ectodomain domain of CD16; (b) a full or partial ectodomain originated from CD64; (c) a non-native (or non-CD16) transmembrane domain; (d) a non-native (or non-CD16) intracellular domain; (e) a non-native (or non-CD16) signaling domain; (f) a non-native stimulatory domain; and (g) transmembrane, signaling, and stimulatory domains that are not originated from CD16, and are originated from a same or different polypeptide. In some embodiments of the method of manufacturing, (a) the non-native transmembrane domain is derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide; (b) the non-native stimulatory domain is derived from CD27, CD28, 4-1BB, OX40, ICOS, PD-1, LAG-3, 2B4, BTLA, DAP10, DAP12, CTLA-4, or NKG2D polypeptide; (c) the non-native signaling domain is derived from CD3ζ, 2B4, DAP10, DAP12, DNAM1, CD137 (4-1BB), IL21, IL7, IL12, IL15, NKp30, NKp44, NKp46, NKG2C, or NKG2D polypeptide; or (d) the non-native transmembrane domain is derived from NKG2D, the non-native stimulatory domain is derived from 2B4, and the non-native signaling domain is derived from CD3ζ.

In some embodiments of the method of manufacturing, the first CAR and the second CAR are the same or are different in targeting specificity, and the first CAR or the second CAR is: (i) T cell specific or NK cell specific; (ii) a bi-specific antigen binding CAR; (iii) a switchable CAR; (iv) a dimerized CAR; (v) a split CAR; (vi) a multi-chain CAR; (vii) an inducible CAR; (viii) co-expressed with another CAR; (ix) co-expressed with a partial or full length peptide of a cell surface expressed exogenous cytokine and/or a receptor thereof, optionally in separate constructs or in a bi-cistronic construct; (x) co-expressed with a checkpoint inhibitor, optionally in separate constructs or in a bi-cistronic construct; (xi)
specific to CD19 or BCMA; and/or (xii) specific to any one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CD S, CLEC12A, an antigen of a cytomegalovirus (CMV) infected cell, epithelial glycoprotein2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen. In other embodiments of the method of manufacturing, the partial or full length peptide of a cell surface expressed exogenous cytokine and/or a receptor thereof: (a) comprises at least one of IL2, IL4, IL6, IL7, IL9, IL10, IL11, IL12, IL15, IL18, IL21, and/or respective receptors thereof; or (b) comprises at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL15β; wherein any one of (i)-(vii) can be co-expressed with a CAR in separate constructs or in a bi-cistronic construct; and optionally, (c) is transiently expressed.

In some embodiments of the method of manufacturing, the first genetically engineered iPSC or the second genetically engineered iPSC further comprises one or more of: (i) HLA-I deficiency; (ii) HLA-II deficiency; (iii) introduced expression of HLA-G or non-cleavable HLA-G; (iv) at least one of lig−, inR+, cs-CD3+, En+, and Ab+; wherein (1) lig− is negative in an expressed alloantigen; (2) inR+ is positive in an expressed inactivation-CAR corresponding to the negative alloantigen; (3) cs-CD3+ is positive in cell surface expressed CD3; (4) En+ is positive in at least one expressed engager, wherein the engager comprises a bi-specific T cell engager (BiTE), or a tri-specific killer cell engager (TriKE); and (5) Ab+ is positive in at least one expressed antibody or checkpoint inhibitor; (v) deletion or reduced expression in at least one of B2M, CIITA, TAP1, TAP2, Tapasin, NLRC5, PD1, LAG3, TIM3, RFXANK, RFX5, RAG1, RFXAP, and any gene in the chromosome 6p21 region; and (vi) introduced or increased expression in at least one of HLA-E, HLA-G, 41BBL, CD4, CD8, CD16, CD47, CD113, CD131, CD137, CD80, PDL1, $A_{2A}R$, TCR, Fc receptor, and surface triggering receptor for coupling with bi- or multi-specific or universal engagers. In certain embodiments, (i) the alloantigen comprises CD40L, OX40, or 4-1BB; (ii) the inactivation-CAR comprises CD40L-CAR, OX40-CAR, or 4-1BB-CAR; (iii) the BiTE or the TriKE is specific to (a) an immune cell surface molecule comprising CD3, CD28, CD5, CD16, NKG2D, CD64, CD32, CD89, NKG2C, or a chimeric Fc receptor thereof; and (b) a tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1; (iv) the BiTE comprises CD3-CD19, CD16-CD30, CD64-CD30, CD16-BCMA, CD64-BCMA, or CD3-CD33; (v) the TriKE comprises CD16-IL15-EPCAM, CD64-IL15-EPCAM, CD16-IL15-CD33, CD64-IL15-CD33, or NKG2C-IL15-CD33; (vi) the antibody comprises an anti-CD20, anti-HER2, anti-CD52, anti-EGFR, anti-CD123, anti-GD2, anti-PDL1, or anti-CD38 antibody; or (vii) the checkpoint inhibitor comprises (a) an antagonist to a checkpoint molecule comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one of atezolizumab, avelumab, durvalumab, ipilimumab, IPH4102, IPH43, IPH33, lirimumab, monalizumab, nivolumab, pembrolizumab, and their derivatives or functional equivalents; or (c) one of atezolizumab, nivolumab, and pembrolizumab.

In some embodiments of the method of manufacturing, the first genetically engineered iPSC or the second genetically engineered iPSC comprise: (i) one or more exogenous polynucleotides integrated in one desired integration site; or (ii) more than two exogenous polynucleotides integrated in different desired integration sites. In certain embodiments, the desired integration site comprises at least one of AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD40L, CD44, CD54, CD56, CD58, CD69, CD71, OX40, 4-1BB, CIS, CBL-B, SOCS2, PD1, CTLA4, LAG3, TIM3, and TIGIT. In other embodiments, the desired integration site comprises TCR α or β constant region, CD25, CD38, CD40L, CD44, CD54, CD58, CD69, CD71, OX40 or 4-1BB; and optionally, wherein the TCRα or TCRβ, CD25, CD38, CD40L, CD44, CD54, CD58, CD69, CD71, OX40 or 4-1BB is knocked out as a result of integrating said one or more exogenous polynucleotides at the respective integration site.

In some embodiments of the method of manufacturing, the iPSC-derived NK cells or the iPSC-derived T cells have at least one of the following characteristics comprising: (i) improved persistency and/or survival, (ii) increased resistance to native immune cells, (iii) increased cytotoxicity, (iv) improved tumor penetration, (v) enhanced or acquired ADCC. (vi) enhanced ability in migrating, and/or activating or recruiting bystander immune cells to tumor sites, (vii) enhanced ability to reduce tumor immunosuppression, and (viii) improved ability in rescuing tumor antigen escape, in comparison to its native counterpart cell obtained from peripheral blood, umbilical cord blood, or any other donor tissues. In various embodiments of the method of manufacturing, the first synthetic cell population or the second synthetic cell population is modulated ex vivo. In certain embodiments, the modulated first synthetic cell population comprising iPSC-derived NK cells comprises an increased number or ratio of type I NKT cells, and/or adaptive NK cells, as compared to the first synthetic cell population without being modulated; or wherein the second modulated synthetic cell population comprising iPSC-derived T cells comprises an increased number or ratio of naïve T cells, stem cell memory T cells, and/or central memory T cells, as compared to the second synthetic cell population without being modulated.

In some embodiments of the method of manufacturing, (i) the iPSC-derived NK cells and the iPSC-derived T cells are in a ratio ranging from 100:1 to 1:100; (ii) the method further comprises adding one or more additional cell populations to the produced first and second synthetic cell populations; or (iii) the method further comprises adding one or more therapeutic agents to the produced first and second synthetic cell populations. In certain embodiments, the one or more additional cell populations comprise regulatory cells. In some embodiments where the one or more additional cell populations comprise regulatory cells, the regulatory cells are iPSC-derived immune regulatory cells or myeloid derived suppressor cells (MDSCs). In some embodiments where the method further comprises adding one or more therapeutic agents to the produced first and second synthetic cell populations, the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (WED). In some embodiments wherein the one or more therapeutic agents comprise checkpoint inhibitors, the checkpoint inhibitor comprises (a) one or more antagonist checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one or more of atezolizumab, avelumab, durvalumab, ipilimumab, IPH4102, IPH43, IPH33, lirimumab, monalizumab, nivolumab, pembrolizumab, and their derivatives or functional equivalents; or (c) at least one of atezolizumab, nivolumab, and pembrolizumab. In some embodiments wherein the one or more therapeutic agents comprise antibodies, the antibody comprises: (a) anti-CD20, anti-HER2, anti-CD52, anti-EGFR, anti-CD123, anti-GD2, anti-PDL1, and/or anti-CD38 antibody; (b) one or more of retuximab, veltuzumab, ofatumumab, ublituximab, ocaratuzumab, obinutuzumab, trastuzumab, pertuzumab, alemtuzumab, certuximab, dinutuximab, avelumab, daratumumab, isatuximab, MOR202, 7G3, CSL362, elotuzumab, and their humanized or Fc modified variants or fragments and their functional equivalents and biosimilars; or (c) daratumumab. In various embodiments of the method of manufacturing, the method further comprises combining the first synthetic cell population and the second synthetic cell population into a mixed population.

Various objects and advantages of the compositions and methods as provided herein will become apparent from the following description taken in conjunction with the accompanying drawings wherein are set forth, by way of illustration and example, certain embodiments of this invention.

DETAILED DESCRIPTION OF THE INVENTION

Figure 1:
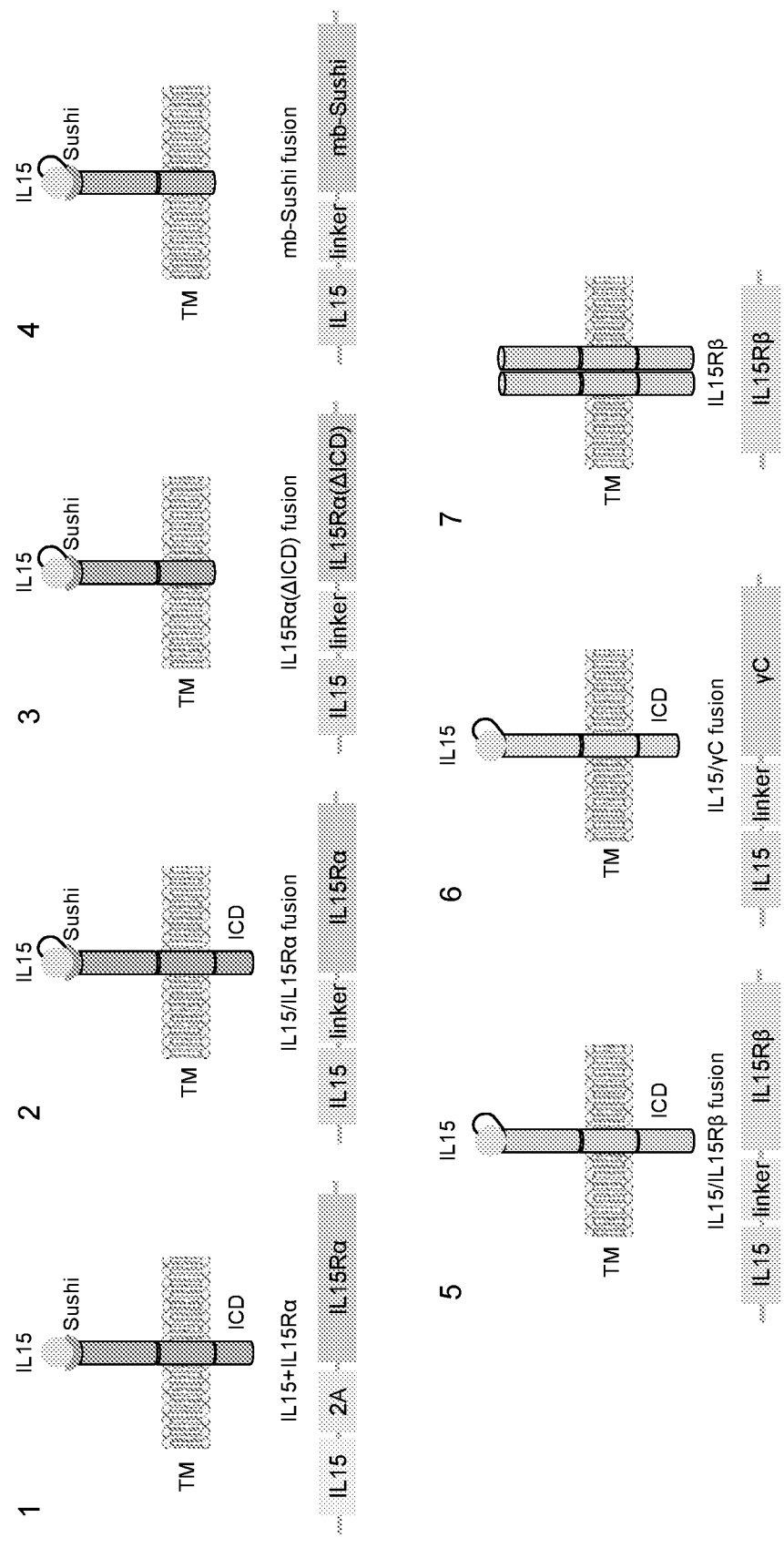
FIG. 1 is a graphic representation of several construct designs for cell surface expressed cytokines or receptors thereof in iPSC-derived cells. IL15 is used as an illustrative example, which can be replaced with other desirable cytokines.

Genomic modification of iPSCs (induced pluripotent stem cells) includes polynucleotide insertion, deletion and substitution. Exogenous gene expression in genome-engineered iPSCs often encounters problems such as gene silencing or reduced gene expression after prolonged clonal expansion of the original genome-engineered iPSCs, after cell differentiation, and in dedifferentiated cell types from the cells derived from the genome-engineered iPSCs. On the other hand, direct engineering of primary immune cells such as T or NK cells is challenging, and presents a hurdle to the preparation and delivery of engineered immune cells for adoptive cell therapy. In various embodiments, the present invention provides an efficient, reliable, and targeted approach for stably integrating one or more exogenous genes, including suicide genes and other functional modalities, which provide improved therapeutic properties relating to engraftment, trafficking, homing, migration, cytotoxicity, viability, maintenance, expansion, longevity, self-renewal, persistence, and/or survival into iPSC derivative cells obtained through directed iPSC differentiation, which derivative cells include but are not limited to HSCs (hematopoietic stem and progenitor cells), hematopoietic multipotent progenitor cells, T cell progenitor cells, NK cell progenitor cells, T cells, NKT cells, NK cells and B cells.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" are used herein to refer to one or to more than one (i.e., to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, both or all of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% of a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition at a functionally inert, low concentration. Similar meaning can be applied to the term "absence of" where referring to the absence of a particular substance or its source thereof of a composition.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refer to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the term "pluripotent" refers to the ability of a cell to form all lineages of the body or soma (i.e., the embryo proper). For example, embryonic stem cells are a type of pluripotent stem cells that are able to form cells from each of the three germs layers: the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism, to the more primitive, more pluripotent cell, which is able to give rise to a complete organism (e.g., an embryonic stem cell).

As used herein, the term "induced pluripotent stem cells" or "iPSCs", refers to stem cells that are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta (i.e., are not totipotent).

As used herein, the term "multipotent stem cell" refers to a cell that has the developmental potential to differentiate into cells of one or more germ layers (i.e., ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to the state of a cell with a degree of developmental potential that is less than totipotent and pluripotent.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) the ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "naïve" or "ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed state of pluripotency. Under standard pluripotent cell culture conditions such cells remain in the primed state unless the exogenous transgene expression is maintained, wherein characteristics of the ground state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, the term "subject" refers to any animal, preferably a human patient, livestock, or other domesticated animal.

A "pluripotency factor," or "reprogramming factor," refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate," or "maintain," refers to the sustaining, propagating (growing) and/or differentiating of cells outside of tissue or the body, for example in a sterile plastic (or coated plastic) cell culture dish or flask. "Cultivation," or "maintaining," may utilize a culture medium as a source of nutrients, hormones and/or other factors helpful to propagate and/or sustain the cells.

As used herein, the term "mesoderm" refers to one of the three germinal layers that appears during early embryogenesis and which gives rise to various specialized cell types including blood cells of the circulatory system, muscles, the heart, the dermis, skeleton, and other supportive and connective tissues.

As used herein, the term "definitive hemogenic endothelium" (HE) or "pluripotent stem cell-derived definitive hemogenic endothelium" (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to CD34$^+$ hematopoietic cells capable of giving rise to both mature myeloid and lymphoid cell types including T lineage cells, NK lineage cells and B lineage cells. Hematopoietic cells also include various subsets of primitive hematopoietic cells that give rise to primitive erythrocytes, megakarocytes and macrophages.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells in an MHC class I-restricted manner. A T cell can be any T cell, such as a cultured T cell, e.g., a primary T cell, or a T cell from a cultured T cell line, e.g., Jurkat, SupT1, etc., or a T cell obtained from a mammal. The T cell can be a CD3$^+$ cell. The T cell can be any type of T cell and can be of any developmental stage, including but not limited to, CD4$^+$/CD8$^+$ double positive T cells, CD4$^+$ helper T cells (e.g., Th1 and Th2 cells), CD8$^+$ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3 (Treg), Th17, Th9, or Tfh cells. Additional types of memory T cells include cells such as central memory T cells (Tcm cells), effector memory T cells (Tem cells and TEMRA cells). The term "T cell" can also refer to a genetically engineered T cell, such as a T cell modified to express a T cell receptor (TCR) or a chimeric antigen receptor (CAR). A T cell or T cell like effector cell can also be differentiated from a stem cell or progenitor cell. A derived T cell like effector cell may have a T cell lineage in some respects, but at the same time has one or more functional features that are not present in a primary T cell. The cells may be referred to as a "synthetic cells" for possessing one or more non-native cell functions when compared to their closest counterpart primary cells.

"CD4$^+$ T cells" refers to a subset of T cells that express CD4 on their surface and are associated with cell-mediated immune response. They are characterized by secretion profiles following stimulation, which may include secretion of cytokines such as IFN-gamma, TNF-alpha, IL2, IL4 and IL10. "CD4" molecules are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"CD8$^+$ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refers to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3$^-$ and CD56$^+$, expressing at least one of NKG2C and CD57, and optionally, CD16, but lack expression of one or more of the following: PLZF, SYK, FceRγ, and EAT-2. In some embodiments, isolated subpopulations of CD56$^+$ NK cells comprise expression of CD16, NKG2C, CD57, NKG2D, NCR ligands, NKp30, NKp40, NKp46, activating and inhibitory KIRs, NKG2A and/or DNAM-1. CD56$^+$ can be dim or bright expression. An NK cell, or an NK cell like effector cell may be differentiated from a stem cell or progenitor cell. A derivative NK cell like effector cell may have an NK cell lineage in some respects, but at the same time has one or more functional features that are not present in a primary NK cell. The cells may be referred to as "synthetic cells" for possessing one or more non-native cell functions when compared to their closest counterpart primary cells.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or non-invariant type II NKT cells, display a more heterogeneous TCR αβ usage. Type I NKT cells are considered suitable for immunotherapy. Adaptive or invariant (type I) NKT cells can be identified by the expression of one or more of the following markers: TCR Va24-Ja18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, isolated from a tissue or biopsy sample. The term also includes a cell that is removed from at least one, some or all components as the cell is found in non-naturally occurring environments, for example, isolated form a cell culture or cell suspension. Therefore, an "isolated" cell is partly or completely separated from at least one component, including other substances, cells or cell populations, as it is found in nature or as it is grown, stored or subsisted in non-naturally occurring environments. Specific examples of isolated cells include partially pure cell compositions, substantially pure cell compositions and cells cultured in a medium that is non-naturally occurring. Isolated cells may be obtained by separating the desired cells, or populations thereof, from other substances or cells in the environment, or by removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as "encoding" the protein or other product of that gene or cDNA.

A "construct" refers to a macromolecule or complex of molecules comprising a polynucleotide to be delivered to a host cell, either in vitro or in vivo. A "vector," as used herein, refers to any nucleic acid construct capable of directing the delivery or transfer of a foreign genetic material to target cells, where it can be replicated and/or expressed. Thus, the term "vector" comprises the construct to be delivered. A vector can be a linear or a circular molecule. A vector can be integrating or non-integrating. The major types of vectors include, but are not limited to, plasmids, episomal vectors, viral vectors, cosmids, and artificial chromosomes. Viral vectors include, but are not limited to, adenovirus vectors, adeno-associated virus vectors, retrovirus vectors, lentivirus vectors, Sendai virus vectors, and the like.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" may further comprise replacement of the endogenous sequence or a nucleotide that is deleted with the one or more inserted nucleotides.

As used herein, the term "exogenous" is intended to mean that the referenced molecule or the referenced activity is introduced into, or is non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e., a polypeptide found in nature) or fragment thereof; a variant polypeptide (i.e., a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. "Polynucleotide" also refers to both double- and single-stranded molecules.

As used herein, the terms "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom, are sometimes collectively called "derived" or "derivative" cells depending on the context. For example, derivative effector cells, or derivative NK lineage cells or derivative T lineage cells, as used throughout this application are cells differentiated from an iPSC, as compared to their primary counterpart obtained from natural/native sources such as peripheral blood, umbilical cord blood, or other donor tissues. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSCs using genomic editing. In the aspect of a source cell obtained from a specifically selected donor, disease or treatment context, the genetic imprint contributing to preferential therapeutic attributes may include any context-specific genetic or epigenetic modifications which manifest a retainable phenotype, i.e. a preferential therapeutic attribute, that is passed on to derivative cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; and resistance to treatment such as chemotherapy. When derivative cells having one or more therapeutic attributes are obtained from differentiating an iPSC that has genetic imprint(s) conferring a preferential therapeutic attribute incorporated thereto, such derivative cells are also called "synthetic cells". For example, synthetic effector cells, or synthetic NK cells or synthetic T cells, as used throughout this application are cells differentiated from a genomically modified iPSC, as compared to their primary counterpart obtained from natural/native sources such as peripheral blood, umbilical cord blood, or other donor tissues.

The term "enhanced therapeutic property" as used herein, refers to a therapeutic property of a cell that is enhanced as compared to a typical immune cell of the same general cell type. For example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; and resistance to treatment such as chemotherapy.

As used herein, the term "engager" refers to a molecule, e.g., a fusion polypeptide, which is capable of forming a link between an immune cell, e.g., a T cell, a NK cell, a NKT cell, a B cell, a macrophage, a neutrophil, and a tumor cell; and activating the immune cell. Examples of engagers include, but are not limited to, bi-specific T cell engagers (BiTEs), bi-specific killer cell engagers (BiKEs), tri-specific killer cell engagers (TriKEs), or multi-specific killer cell engagers, or universal engagers compatible with multiple immune cell types.

As used herein, the term "surface triggering receptor" refers to a receptor capable of triggering or initiating an immune response, e.g., a cytotoxic response. Surface triggering receptors may be engineered, and may be expressed on effector cells, e.g., a T cell, a NK cell, a NKT cell, a B cell, a macrophage, or a neutrophil. In some embodiments, the surface triggering receptor facilitates bi- or multi-specific antibody engagement between the effector cells and a specific target cell, e.g., a tumor cell, independent of the effector cells' natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers having the same epitope recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cells in some cases, and to kill two or more types of tumors in other cases. A surface triggering receptor generally comprises a co-stimulatory domain for effector cell activation and an anti-epitope that is specific to the epitope of an engager. A bi-specific engager is specific to the anti-epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch protein could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g., a prodrug, that when activated, triggers apoptosis and/or cell death of a therapeutic cell. Examples of safety switch proteins include, but are not limited to, suicide genes such as caspase 9 (or caspase 3 or 7), thymidine kinase, cytosine deaminase, B cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refers to proteins or peptides that are capable of achieving a biological and/or pharmaceutical effect on an organism. A pharmaceutically active protein has healing, curative or palliative properties against a disease and may be administered to ameliorate, relieve, alleviate, reverse or lessen the severity of a disease. A pharmaceutically active protein also has prophylactic properties and is used to prevent the onset of a disease or to lessen the severity of such disease or pathological condition when it does emerge. "Pharmaceutically active proteins" include an entire protein or peptide or pharmaceutically active fragments thereof. The term also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, cellular signal transduction. "Signal transduction" refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes, but is not limited to, i) antigen specificity as it relates to a unique chimeric antigen receptor (CAR) or T cell receptor (TCR), ii) engager specificity as it relates to monoclonal antibodies or bispecific engagers, iii) targeting of transformed cells, iv) targeting of cancer stem cells, and v) other targeting strategies in the absence of a specific antigen or surface molecule.

As used herein, the term "specific" or "specificity" can be used to refer to the ability of a molecule, e.g., a receptor or an engager, to selectively bind to a target molecule, in contrast to non-specific or non-selective binding.

The term "adoptive cell therapy" as used herein refers to a cell-based immunotherapy that relates to the transfusion of autologous or allogenic lymphocytes, identified as T or B cells, genetically modified or not, that have been expanded ex vivo prior to said transfusion.

A "therapeutically sufficient amount", as used herein, includes within its meaning a non-toxic, but sufficient and/or effective amount of a particular therapeutic agent and/or pharmaceutical composition to which it is referring to provide a desired therapeutic effect. The exact amount required will vary from subject to subject, depending on factors such as the patient's general health, the patient's age and the stage and severity of the condition being treated. In particular embodiments, a "therapeutically sufficient amount" is sufficient and/or effective to ameliorate, reduce, and/or improve at least one symptom associated with a disease or condition of the subject being treated.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate lineage-specific differentiation. "Embryoid bodies" are three-dimensional clusters that have been shown to mimic embryo development as they give rise to numerous lineages within their three-dimensional area. Through the differentiation process, typically a few hours to days, simple EBs (for example, aggregated pluripotent stem cells elicited to differentiate) continue maturation and develop into a cystic EB at which time, typically days to a few weeks, they are further processed to continue differentiation. EB formation is initiated by bringing pluripotent stem cells into close proximity with one another in three-dimensional multilayered clusters of cells. Typically, this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (i.e., ectoderm, mesoderm and endoderm germ layers) with modest proliferation within the EB cell cluster. Although proven to facilitate cell differentiation, EBs, however, give rise to heterogeneous cells in variable differentiation states because of the inconsistent exposure of the cells in the three-dimensional structure to the differentiation cues within the environment. In addition, EBs are laborious to create and maintain. Moreover, cell differentiation through EBs is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cell proliferation generally increases the size of the aggregates, forming larger aggregates, which can be routinely mechanically or enzymatically dissociated into smaller aggregates to maintain cell proliferation within the culture and increase numbers of cells. As distinct from EB culture, cells cultured within aggregates in maintenance culture media maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation to initiate differentiation. Because monolayer culturing does not mimic embryo development such as is the case with EB formation, differentiation towards specific lineages is deemed to be minimal as compared to all three germ layer differentiation in EB formation.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be enzymatically or mechanically dissociated from each other, such as by dissociation into a suspension of clusters, single cells or a mixture of single cells and clusters. In yet another alternative embodiment, adherent cells can be dissociated from a culture plate or other surface. Dissociation thus can involve breaking cell interactions with extracellular matrix (ECM) and substrates (e.g., culture surfaces), or breaking the ECM between cells.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell type, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day, and therefore contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

"Functional" as used in the context of genomic editing or modification of iPSC, and derived non-pluripotent cells differentiated therefrom, or genomic editing or modification of non-pluripotent cells and derived iPSCs reprogrammed therefrom, refers to (1) at the gene level—successful knocked-in, knocked-out, knocked-down gene expression, transgenic or controlled gene expression such as inducible or temporal expression at a desired cell development stage, which is achieved through direct genomic editing or modification, or through "passing-on" via differentiation from or reprogramming of a starting cell that is initially genomically engineered; or (2) at the cell level—successful removal, addition, or alteration of a cell function/characteristic via (i) gene expression modification obtained in said cell through direct genomic editing, (ii) gene expression modification maintained in said cell through "passing-on" via differentiation from or reprogramming of a starting cell that is initially genomically engineered; (iii) down-stream gene regulation in said cell as a result of gene expression modification that only appears in an earlier development stage of said cell, or only appears in the starting cell that gives rise to said cell via differentiation or reprogramming; or (iv) enhanced or newly attained cellular function or attribute displayed within the mature cellular product, initially derived from the genomic editing or modification conducted at the iPSC, progenitor or dedifferentiated cellular origin.

"HLA deficient", including HLA-class I deficient, HLA-class II deficient, or both, refers to cells that either lack, or no longer maintain, or have a reduced level of surface expression of a complete MHC complex comprising a HLA class I protein heterodimer and/or a HLA class II heterodimer, such that the diminished or reduced level is less than the level naturally detectable by other cells or by synthetic methods.

"Modified HLA deficient iPSC." as used herein, refers to an HLA deficient iPSC that is further modified by introducing genes expressing proteins related, but not limited to improved differentiation potential, antigen targeting, antigen presentation, antibody recognition, persistence, immune evasion, resistance to suppression, proliferation, costimulation, cytokine stimulation, cytokine production (autocrine or paracrine), chemotaxis, and cellular cytotoxicity, such as non-classical HLA class I proteins (e.g., HLA-E and HLA-G), chimeric antigen receptor (CAR), T cell receptor (TCR), CD16 Fc Receptor, BCL11b, NOTCH, RUNX1, IL15, 4-1BB, DAP10, DAP12, CD24, CD3, 4-1BBL, CD47, CD113, and PDL1. The cells that are "modified HLA deficient" also include cells other than iPSCs.

"Fc receptors," abbreviated FcR, are classified based on the type of antibody that they recognize. For example, those that bind the most common class of antibody, IgG, are called Fc-gamma receptors (FcγR), those that bind IgA are called Fc-alpha receptors (FcαR) and those that bind IgE are called Fc-epsilon receptors (FcεR). The classes of FcR's are also distinguished by the cells that express them (macrophages, granulocytes, natural killer cells, T and B cells) and the signaling properties of each receptor. Fc-gamma receptors (FcγR) includes several members, FcγRI (CD64), FcγRIIA (CD32), FcγRIIB (CD32), FcγRIIIA (CD16a), FcγRIIIB (CD16b), which differ in their antibody affinities due to their different molecular structures.

"Chimeric Fc Receptor," abbreviated as CFcR, is a term used to describe engineered Fc receptors having their native transmembrane and/or intracellular signaling domains modified, or replaced with non-native transmembrane and/or intracellular signaling domains. In some embodiments of the chimeric Fc receptor, in addition to having one of, or both of, the transmembrane and signaling domains being non-native, one or more stimulatory domains can be introduced to the intracellular portion of the engineered Fc receptor to enhance cell activation, expansion and function upon triggering of the receptor. Unlike a chimeric antigen receptor (CAR), which contains an antigen binding domain to a target antigen, the chimeric Fc receptor binds to an Fc fragment, or the Fc region of an antibody, or the Fc region comprised in an engager or a binding molecule and activates the cell function with or without bringing the targeted cell close in vicinity. For example, a Fcγ receptor can be engineered to comprise selected transmembrane, stimulatory, and/or signaling domains in the intracellular region that respond to the binding of IgG at the extracellular domain, thereby generating a CFcR. In one example, a CFcR is produced by engineering CD16, a Fcγ receptor, by replacing its transmembrane domain and/or intracellular domain. To further improve the binding affinity of the CD16-based CFcR, the extracellular domain of CD64 or the high-affinity variants of CD16 (F176V, for example) can be incorporated. In some embodiments of the CFcR where a high affinity CD16 extracellular domain is involved, the proteolytic cleavage site comprising a serine at position 197 is eliminated or is replaced such at the extracellular domain of the receptor is non-cleavable, i.e., not subject to shedding, thereby obtaining a hnCD16-based CFcR.

CD16, a FcγR receptor, has been identified to have two isoforms: Fc receptors FcγRIIIa (CD16a) and FcγRIIIb (CD16b). CD16a is a transmembrane protein expressed by NK cells, which binds monomeric IgG attached to target cells to activate NK cells and facilitate antibody-dependent cell-mediated cytotoxicity (ADCC). "High affinity CD16," "non-cleavable CD16," or "high affinity non-cleavable CD16" (abbreviated hnCD16), as used herein, refers to a natural or non-natural variant of CD16. The wildtype CD16 has low affinity and is subject to ectodomain shedding, a proteolytic cleavage process that regulates the cell surface density of various cell surface molecules on leukocytes upon NK cell activation. F176V and F158V are exemplary CD16 polymorphic variants having high affinity. A CD16 variant having the cleavage site (position 195-198) in the membrane-proximal region (position 189-212) altered or eliminated is not subject to shedding. The cleavage site and the membrane-proximal region are described in detail in WO2015/148926, the complete disclosure of which is incorporated herein by reference. The CD16 S197P variant is an engineered non-cleavable version of CD16. A CD16 variant comprising both F158V and S197P has high affinity and is non-cleavable. Another exemplary high affinity and non-cleavable CD16 (hnCD16) variant is an engineered CD16 comprising an ectodomain originated from one or more of the 3 exons of the CD64 ectodomain.

I. Cells and Compositions Useful for Adoptive Cell Therapies with Enhanced Properties Provided herein is a strategy to systematically engineer the regulatory circuitry of a clonal iPSC without impacting the differentiation potency and cell development biology of the iPSC and its derivative cells, while enhancing the therapeutic properties of the derivative cells differentiated from the iPSC. The iPSC-derived cells are functionally improved and suitable for adoptive cell therapies following a combination of selective modalities being introduced to the cells at the level of iPSC through genomic engineering. It was unclear, prior to this invention, whether altered iPSCs comprising one or more provided genetic edits still have the capacity to enter cell development, and/or to mature and generate functional differentiated cells while retaining modulated activities. Unanticipated failures during directed cell differentiation from iPSCs have been attributed to aspects including, but not limited to, development stage specific gene expression or lack thereof, requirements for HLA complex presentation, protein shedding of introduced surface expressing modalities, and the need for reconfiguration of differentiation protocols enabling phenotypic and/or functional change in the cell. The present application has shown that the one or more selected genomic modifications as provided herein does not negatively impact iPSC differentiation potency, and the functional effector cells derived from the engineered iPSC have enhanced and/or acquired therapeutic properties attributable to the individual or combined genomic modifications retained in the effector cells following the iPSC differentiation.

1. hnCD16 Knock-In

As discussed above, CD16 has been identified as two isoforms, Fc receptors FcγRIIIa (CD16a; NM_000569.6) and FcγRIIIb (CD16b; NM_000570.4). CD16a is a transmembrane protein expressed by NK cells, which binds monomeric IgG attached to target cells to activate NK cells and facilitate antibody-dependent cell-mediated cytotoxicity (ADCC). CD16b is exclusively expressed by human neutrophils. "High affinity CD16," "non-cleavable CD16," "high affinity non-cleavable CD16," or "hnCD16," as used herein, refers to various CD16 variants. The wildtype CD16 has low affinity and is subject to ectodomain shedding, a proteolytic cleavage process that regulates the cells surface density of various cell surface molecules on leukocytes upon NK cell activation. F176V (also called F158V in some publications) is an exemplary CD16 polymorphic allele/variant having high affinity; whereas S197P variant is an example of genetically engineered non-cleavable version of CD16. An engineered CD16 variant comprising both F176V and S197P has high affinity and is non-cleavable, which was described in greater detail in WO2015/148926, and the complete disclosure of which is incorporated herein by reference. In addition, a chimeric CD16 receptor with the ectodomain of CD16 essentially replaced with at least a portion of the CD64 ectodomain can also achieve the desired high affinity and non-cleavable features of a CD16 receptor capable of carrying out ADCC. In some embodiments, the replacement ectodomain of a chimeric CD16 comprises one or more of EC1, EC2, and EC3 exons of CD64 (UniPRotKB_P12314 or its isoform or polymorphic variant).

As such, a high-affinity non-cleavable CD16 receptor (hnCD16), in some embodiments, comprises both F176V and S197P; and in some embodiments, comprises F176V and with the cleavage region eliminated. In some other embodiments, a hnCD16 comprises a sequence having identity of at least 50%, 55%, 60%, 65%, 70%, 75%, 80%, 85%, 90%, 95%, 99%, 100%, or any percentage in-between, when compared to any of the exemplary sequences, SEQ ID NOs. 1-3, each comprising at least a portion of the CD64 ectodomain. SEQ ID NOs. 1-3 are encoded respectively by exemplifying SEQ ID NOs. 4-6. As used herein and throughout the application, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm recognized in the art.

```
SEQ ID NO. 1:
MWFLTTLLLWVPVDGQVDTTKAVITLQPPWVSVFQEETVTLHCEVLHLPGSSSTQWFLNGTATQ

TSTPSYRITSASVNDSGEYRCQRGLSGRSDPIQLEIHRGWLLLQVSSRVFTEGEPLALRCHAWK

DKLVYNVLYYRNGKAFKFFHWNSNLTILKTNISHNGTYHCSGMGKHRYTSAGISVTVKELFPAP

VLNASVTSPLLEGNLVTLSCETKLLLQRPGLQLYFSFYMGSKTLRGRNTSSEYQILTARREDSG

LYWCEAATEDGNVLKRSPELELQVLGLQLPTPVWFHYQ*VSFCLVMVLLFAVDTGLYFSVKTNIR*

*SSTRDWKDHKFKWRKDPQDK*
(340 a.a. CD64 domain-based construction; CD16TM; CD16ICD)
```

SEQ ID NO. 2
```
MWFLTTLLLWVPVDGQVDTTKAVITLQPPWVSVFQEETVTLHCEVLHLPGSSSTQWFLNGTATQ

TSTPSYRITSASVNDSGEYRCQRGLSGRSDPIQLEIHRGWLLLQVSSRVFTEGEPLALRCHAWK
```

-continued

DKLVYNVLYYRNGKAFKFFHWNSNLTILKTNISHNGTYHCSGMGKHRYTSAGISVTVKELFPAP

VLNASVTSPLLEGNLVTLSCETKLLLQRPGLQLYFSFYMGSKTLRGRNTSSEYQILTARREDSG

LYWCEAATEDGNVLKRSPELELQVLGLFFPPGYQ*VSFCLVMVLLFAVDTGLYFSVKTNIRSSTR*

*DWKDHKFKWRKDPQDK*
(336 a.a. CD64 exon-based construction; CD16TM; CD16ICD)

SEQ ID NO. 3

MWFLTTLLLWVPVDGQVDTTKAVITLQPPWVSVFQEETVTLHCEVLHLPGSSSTQWFLNGTATQ

TSTPSYRITSASVNDSGEYRCQRGLSGRSDPIQLEIHRGWLLLQVSSRVFTEGEPLALRCHAWK

DKLVYNVLYYRNGKAFKFFHWNSNLTILKTNISHNGTYHCSGMGKHRYTSAGISVTVKELFPAP

VLNASVTSPLLEGNLVTLSCETKLLLQRPGLQLYFSFYMGSKTLRGRNTSSEYQILTARREDSG

LYWCEAATEDGNVLKRSPELELQVLGFFPPGYQ*VSFCLVMVLLFAVDTGLYFSVKTNIRSSTRD*

*WKDHKFKWRKDPQDK*
(335 a.a. CD64 exon-based construction; CD16TM; CD16ICD)

SEQ ID NO. 4
```
cttggagaca acatgtggtt cttgacaact ctgctccttt gggttccagt tgatgggcaa gtggacacca caaaggcagt gatcactttg cagcctccat gggtcagcgt gttccaagag gaaaccgtaa ccttgcattg tgaggtgctc catctgcctg ggagcagctc tacacagtgg tttctcaatg gcacagccac tcagacctcg acccccagct acagaatcac ctctgccagt gtcaatgaca gtggtgaata caggtgccag agaggtctct cagggcgaag tgaccccata cagctggaaa tccacagagg ctggctacta ctgcaggtct ccagcagagt cttcacggaa ggagaacctc tggccttgag gtgtcatgcg tggaaggata agctggtgta caatgtgctt tactatcgaa atggcaaagc ctttaagttt ttccactgga attctaacct caccattctg aaaaccaaca taagtcacaa tggcacctac cattgctcag gcatgggaaa gcatcgctac acatcagcag gaatatctgt cactgtgaaa gagctatttc cagctccagt gctgaatgca tctgtgacat ccccactcct ggaggggaat ctggtcaccc tgagctgtga aacaaagttg ctcttgcaga ggcctggttt gcagctttac ttctccttct acatgggcag caagaccctg cgaggcagga cacatcctc tgaataccaa atactaactg ctagaagaga agactctggg ttatactggt gcgaggctgc cacagaggat ggaaatgtcc ttaagcgcag ccctgagttg gagcttcaag tgcttggcct ccagttacca actcctgtct ggtttcatta ccaagtctct ttctgcttgg tgatggtact ccttttgca gtggacacag gactatattt ctctgtgaag acaaacattc gaagctcaac aagagactgg aaggaccata aatttaaatg gagaaaggac cctcaagaca aa
```
SEQ ID NO. 5
```
cttggagaca acatgtggtt cttgacaact ctgctccttt gggttccagt tgatgggcaa gtggacacca caaaggcagt gatcactttg cagcctccat gggtcagcgt gttccaagag gaaaccgtaa ccttgcattg tgaggtgctc catctgcctg ggagcagctc tacacagtgg tttctcaatg gcacagccac tcagacctcg acccccagct acagaatcac ctctgccagt gtcaatgaca gtggtgaata caggtgccag agaggtctct cagggcgaag tgaccccata cagctggaaa tccacagagg ctggctacta ctgcaggtct ccagcagagt cttcacggaa ggagaacctc tggccttgag gtgtcatgcg tggaaggata agctggtgta caatgtgctt tactatcgaa atggcaaagc ctttaagttt ttccactgga attctaacct caccattctg aaaaccaaca taagtcacaa tggcacctac cattgctcag gcatgggaaa gcatcgctac acatcagcag gaatatctgt cactgtgaaa gagctatttc cagctccagt gctgaatgca tctgtgacat ccccactcct ggaggggaat ctggtcaccc tgagctgtga aacaaagttg
```

-continued

```
ctcttgcaga ggcctggttt gcagctttac ttctccttct acatgggcag caagaccctg cgaggcagga acacatcctc tgaataccaa atactaactg ctagaagaga agactctggg ttatactggt gcgaggctgc cacagaggat ggaaatgtcc ttaagcgcag ccctgagttg gagcttcaag tgcttggttt gttctttcca cctgggtacc aagtctcttt ctgcttggtg atggtactcc tttttgcagt ggacacagga ctatatttct ctgtgaagac aaacattcga agctcaacaa gagactggaa ggaccataaa tttaaatgga gaaaggaccc tcaagacaaa
```

SEQ ID NO. 6

```
atgtggttct tgacaactct gctcctttgg gttccagttg atgggcaagt ggacaccaca aaggcagtga tcactttgca gcctccatgg gtcagcgtgt tccaagagga aaccgtaacc ttgcactgtg aggtgctcca tctgcctggg agcagctcta cacagtggtt tctcaatggc acagccactc agacctcgac ccccagctac agaatcacct ctgccagtgt caatgacagt ggtgaataca ggtgccagag aggtctctca gggcgaagtg accccataca gctggaaatc cacagaggat ggctactact gcaggtctcc agcagagtct tcacggaagg agaacctctg gccttgaggt gtcatgcgtg gaaggataag ctggtgtaca atgtgcttta ctatcgaaat ggcaaagcct ttaagttttt ccactgaaac tctaacctca ccattctgaa aaccaacata agtcacaatg gcacctacca ttgctcaggc atgggaaagc atcgctacac atcagcagga atatctgtca ctgtgaaaga gctatttcca gctccagtgc tgaatgcatc tgtgacatcc ccactcctgg aggggaatct ggtcaccctg agctgtgaaa caaagttgct cttgcagagg cctggtttgc agctttactt ctccttctac atgggcagca agaccctgcg aggcaggaac acatcctctg aataccaaat actaactgct agaagagaag actctgggtt atactggtgc gaggctgcca cagaggatgg aaatgtcctt aagcgcagcc ctgagttgga gcttcaagtg cttggcttct ttccacctgg gtaccaagtc tctttctgct tggtgatggt actccttttt gcagtggaca caggactata tttctctgtg aagacaaaca ttcgaagctc aacaagagac tggaaggacc ataaatttaa atggagaaag gaccctcaag acaaa
```

Accordingly, provided herein are clonal iPSCs genetically engineered to comprise, among other edits as contemplated and described herein, an exogenous CD16 (e.g., a high-affinity non-cleavable CD16 receptor (hnCD16)), wherein the genetically engineered iPSCs are capable of differentiating into effector cells comprising the exogenous CD16 introduced to the iPSCs. In some embodiments, the derived effector cells comprising exogenous CD16 are NK cells. In some embodiments, the derived effector cells comprising exogenous CD16 are T cells. The exogenous CD16 expressed in iPSCs or derivative cells therefrom has high affinity in binding to not only ADCC antibodies or fragments thereof, but also to bi-, tri-, or multi-specific engagers or binders that recognize the CD16 or CD64 extracellular binding domains of said exogenous CD16 and variants thereof. The bi-, tri-, or multi-specific engagers or binders are further described below in this application (see below). As such, the present application provides a derivative effector cell or a cell population thereof preloaded with one or more pre-selected ADCC antibodies through high-affinity binding with the extracellular domain of the exogenous CD16 expressed on the derivative effector cell, in an amount sufficient for therapeutic use in a treatment of a condition, a disease, or an infection as further detailed below, wherein said exogenous CD16 comprises an extracellular binding domain of CD64, or of CD16 having F176V and S197P.

In some other embodiments, the native CD16 transmembrane- and/or the intracellular-domain of a hnCD16 is further modified or replaced, such that a chimeric Fc receptor (CFcR) comprising a non-native transmembrane domain, a non-native stimulatory domain and/or a non-native signaling domain is produced. The term "non-native" used herein means that the transmembrane, stimulatory and/or signaling domains are derived from a different receptor other than the receptor which provides the extracellular domain. In the exemplary illustration here, the CFcR based on CD16 or variants thereof does not have a transmembrane, stimulatory or signaling domain that is derived from CD16. In some embodiments, the exogenous CD16-based CFcR comprises a non-native transmembrane domain derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or a T cell receptor polypeptide. In some embodiments, the exogenous CD16-based CFcR comprises a non-native stimulatory/inhibitory domain derived from CD27, CD28, 4-1BB, OX40, ICOS, PD-1, LAG-3, 2B4, BTLA, DAP10, DAP12, CTLA-4, or NKG2D polypeptide. In some embodiments, the exogenous CD16-based CFcR comprises a non-native signaling domain derived from CD3ζ, 2B4, DAP10, DAP12, DNAM1, CD137 (4-1BB), IL21, IL7, IL12, IL15, NKp30, NKp44, NKp46, NKG2C, or NKG2D polypeptide. In one embodiment, the provided chimeric receptor comprises a transmembrane domain and a signaling domain both derived from one of IL7, IL12, IL15, NKp30, NKp44, NKp46, NKG2C, and NKG2D polypeptide. One particular embodiment of the CD16-based chimeric Fc receptor comprises a transmembrane domain of NKG2D, a stimulatory domain of 2B4, and a signaling domain of CD3ζ; wherein the extracellular domain of the hnCD16 is derived from a full length or partial sequence of the extracellular domain of CD64 or CD16, wherein the extracellular domain of CD16 comprises F176V and S197P. Another embodiment of the CD16-based chimeric Fc receptor comprises a transmembrane domain and a signaling domain of CD3ζ; wherein the extracellular domain of the hnCD16 is derived from a full length or partial sequence of the extracellular domain of CD64 or CD16, wherein the extracellular domain of CD16 comprises F176V and S197P.

The various embodiments of CD16-based chimeric Fc receptors as described above are capable of binding, with high affinity, to the Fc region of an antibody or fragment thereof; or to the Fc region of a bi-, tri-, or multi-specific engager or binder. Upon binding, the stimulatory and/or signaling domains of the chimeric receptor enable the activation and cytokine secretion of the effector cells, and the killing of the tumor cells targeted by the antibody, or said bi-, tri-, or multi-specific engager or binder having a tumor antigen binding component as well as the Fc region. Without being limited by theory, through the non-native transmembrane, stimulatory and/or signaling domains, or through an engager binding to the ectodomain, of the CD16-based chimeric Fc receptor, the CFcR could contribute to effector cells' killing ability while increasing the effector cells' proliferation and/or expansion potential. The antibody and the engager can bring tumor cells expressing the antigen and the effector cells expressing the CFcR into close proximity with each other, which also contributes to the enhanced killing of the tumor cells. Exemplary tumor antigens for bi-, tri-, multi-specific engagers or binders include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, and ROR1. Some non-limiting exemplary bi-, tri-, multi-specific engagers or binders suitable for engaging effector cells expressing the CD16-based CFcR in attacking tumor cells include CD16 (or CD64)-CD30, CD16 (or CD64)-BCMA, CD16 (or CD64)-IL15-EPCAM, and CD16 (or CD64)-IL15-CD33.

Unlike the endogenous CD16 receptor expressed by primary NK cells which gets cleaved from the cellular surface following NK cell activation, the various non-cleavable versions of CD16 in derivative NK cells avoid CD16 shedding and maintain constant expression. In derivative NK cells, non-cleavable CD16 increases expression of TNFα and CD107a, indicative of improved cell functionality. Non-cleavable CD16 also enhances antibody-dependent cell-mediated cytotoxicity (ADCC), and the engagement of bi-, tri-, or multi-specific engagers. ADCC is a mechanism of NK cell mediated lysis through the binding of CD16 to antibody-coated target cells. The additional high affinity characteristics of the introduced hnCD16 in derived NK cells also enables in vitro loading of ADCC antibody to the NK cells through hnCD16 before administering the cell to a subject in need of a cell therapy. As provided, the hnCD16 may comprise F176V and S197P in some embodiments, or may comprise a full or partial ectodomain originated from CD64 as exemplified by SEQ ID NOs: 1, 2 or 3, or may further comprise at least one of a non-native transmembrane domain, stimulatory domain and signaling domain. As disclosed, the present application also provides a derivative NK cell or a cell population thereof, preloaded with one or more pre-selected ADCC antibodies in an amount sufficient for therapeutic use in a treatment of a condition, a disease, or an infection as further detailed below.

Unlike primary NK cells, mature T cells from a primary source (i.e., natural/native sources such as peripheral blood, umbilical cord blood, or other donor tissues) do not express CD16. It was unexpected that iPSCs comprising an expressed exogenous non-cleavable CD16 did not impair T cell developmental biology and were able to differentiate into functional derivative T lineage cells that not only express the exogenous CD16, but also are capable of carrying out functions through an acquired ADCC mechanism. This acquired ADCC in the derivative T lineage cell can additionally be used as an approach for dual targeting and/or to rescue antigen escape which often occurs with CAR-T cell therapy, where the tumor relapses with reduced or lost CAR-T targeted antigen expression or expression of a mutated antigen to avoid recognition by the CAR. When said derivative T lineage cell comprises acquired ADCC through exogenous CD16, including functional variants and CD16 based CFcR, expression, and when an antibody targets a different tumor antigen from the one targeted by the CAR, the antibody can be used to rescue CAR-T antigen escape and reduce or prevent relapse or recurrence of the targeted tumor often seen in CAR-T treatment. Such a strategy to reduce and/or prevent antigen escape while achieving dual targeting is equally applicable to NK cells expressing one or more CARs. The various CARs that can be used in this antigen escape reduction and prevention strategy is further delineated below.

As such, embodiments of the present invention provide a derivative T lineage cell comprising an exogenous CD16. In some embodiments, the CD16 comprised in the derivative T lineage cell is an hnCD16 comprising F176V and S197P. In some other embodiments, the hnCD16 comprised in the derivative T lineage cell comprises a full or partial ectodomain originated from CD64 as exemplified by SEQ ID NO: 1, 2 or 3, or may further comprise at least one of a non-native transmembrane domain, stimulatory domain and signaling domain. As explained, such derivative T lineage cells have an acquired mechanism to target tumors with a monoclonal antibody mediated by ADCC to enhance the therapeutic effect of the antibody. As disclosed, the present application also provides a derivative T lineage cell or a cell population thereof, preloaded with one or more pre-selected ADCC antibodies in an amount sufficient for therapeutic use in a treatment of a condition, a disease, or an infection as further detailed below.

Additionally provided in this application is a master cell bank comprising single cell sorted and expanded clonal engineered iPSCs having at least one phenotype as provided herein, including but not limited to, an exogenous CD16, wherein the cell bank provides a platform for additional iPSC engineering and a renewable source for manufacturing off-the-shelf, engineered, homogeneous cell therapy products, including but not limited to derivative NK and T cells, which are well-defined and uniform in composition, and can be mass produced at significant scale in a cost-effective manner.

2. CAR Expression

Applicable to the genetically engineered iPSC and derivative effector cell thereof may be any CAR design known in the art. CAR, a chimerical antigen receptor, is a fusion protein generally including an ectodomain that comprises an antigen recognition region, a transmembrane domain, and an endodomain. In some embodiments, the ectodomain can further include a signal peptide or leader sequence and/or a spacer. In some embodiments, the CARs described herein are designed to be expressed and function in induced pluripotent stem cells (iPSCs), and derivative effector cells that are differentiated from the iPSCs engineered to comprise the CAR. In some embodiments, the CAR described herein is designed such that it does not disrupt iPSC differentiation, and/or it promotes differentiation of iPSC directed to a desired effector cell type. In some embodiments, the CAR enhances effector cell expansion, persistence, survival, cytotoxicity, resistance to allorejection, tumor penetration, migration, ability in activating and/or recruiting bystander immune cells, and/or ability to overcome tumor suppression. In embodiments, the CARs provided herein can also be expressed directly in cell-line cells and cells from a primary source, i.e., natural/native sources such as peripheral blood, umbilical cord blood, or other donor tissues.

In some embodiments, the CAR is suitable to activate either T or NK lineage cells expressing said CAR. In some embodiments, the CAR is NK cell specific by comprising NK-specific signaling components. In certain embodiments, said T lineage cells are derived from CAR expressing iPSCs, and the derivative T lineage cells may comprise T helper cells, cytotoxic T cells, memory T cells, regulatory T cells, natural killer T cells, αβ T cells, γδ T cells, or a combination thereof. In certain embodiments, said NK lineage cells are derived from a CAR expressing iPSCs. In some embodiments, the CAR comprising NK cell-specific signaling components is also suitable for T cells, or other cell types. In some embodiments, the CAR is T cell specific by comprising T cell-specific signaling components. In some embodiments, the CAR comprising T cell-specific signaling components are also suitable for NK cell, or other cell types. In some embodiments, the CAR is NKT cell specific by comprising NKT cell-specific signaling components. In some embodiments, the CAR comprising NKT cell-specific signaling components is also suitable for NK or T cell, or other cell types.

In certain embodiments, said antigen recognition region comprises a murine antibody, a human antibody, a humanized antibody, a camel Ig, a shark heavy-chain-only antibody (VNAR), Ig NAR, a chimeric antibody, a recombinant antibody, or antibody fragment thereof. Non-limiting examples of antibody fragment include Fab, Fab', F(ab') 2, F(ab') 3, Fv, single chain antigen binding fragment (scFv), (scFv)$_2$, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody. Non-limiting examples of antigen that may be targeted by the CAR(s) comprised in genetically engineered iPSCs and derivative effector cells include ADGRE2, carbonic anhydrase IX (CAIX), CCR1, CCR4, carcinoembryonic antigen (CEA), CD3, CD5, CD7, CD8, CD10, CD19, CD20, CD22, CD30, CD33, CD34, CD38, CD41, CD44, CD44V6, CD49f, CD56, CD70, CD74, CD99, CD123, CD133, CD138, CD269 (BCMA), CDS, CLEC12A, an antigen of a cytomegalovirus (CMV) infected cell (e.g., a cell surface antigen), epithelial glycoprotein 2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBCI, TRBC2, vascular endothelial growth factor R2 (VEGF-R2), Wilms tumor protein (WT-1), and various pathogenic antigens known in the art. Non-limiting examples of pathogens include virus, bacteria, fungi, parasite and protozoa capable of causing diseases.

In some embodiments, the transmembrane domain of a CAR comprised in genetically engineered iPSCs and derivative effector cells comprises a full length or at least a portion of the native or modified transmembrane region of CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NLp44, NKp46, NKG2C, NKG2D, and T cell receptor polypeptide.

In some embodiments, the signaling peptide of the endodomain (or intracellular domain) of a CAR comprised in genetically engineered iPSCs and derivative effector cells comprises a full length or at least a portion of a polypeptide of CD3ζ, 2B4, DAP10, DAP12, DNAM1, CD137 (4-1BB), IL21, IL7, IL12, IL15, NKp30, NKp44, NKp46, NKG2C, or NKG2D. In one embodiment, the signaling peptide of a CAR comprises an amino acid sequence that has at least about 85%, about 90%, about 95%, about 96%, about 97%, about 98%, or about 99% identity to at least one ITAM (immunoreceptor tyrosine-based activation motif) of CD3ζ.

In certain embodiments, said endodomain further comprises at least one costimulatory signaling region. Said costimulatory signaling region comprises a full length or at least a portion of a polypeptide of CD27, CD28, 4-1BB, OX40, ICOS, PD-1, LAG-3, 2B4, BTLA, DAP10, DAP12, CTLA-4, or NKG2D, or any combination thereof. In one embodiment, the CAR applicable to the cells provided in this application comprises a costimulatory domain derived from CD28, and a signaling domain comprising the native or modified ITAM1 of CD3ζ, represented by an amino acid sequence of at least about 85%, about 90%, about 95%, about 96%, about 97%, about 98%, or about 99% identity to SEQ ID NO: 7. In a further embodiment, the CAR comprising a costimulatory domain derived from CD28, and a native or modified ITAM1 of CD3ζ also comprises a hinge domain and transmembrane domain derived from CD28, wherein an scFv may be connected to the transmembrane domain through the hinge, and the CAR comprises an amino acid sequence of at least about 80%, about 85%, about 90%, about 95%, about 96%, about 97%, about 98%, or about 99% identity to SEQ ID NO: 8.

```
                                                      SEQ ID NO: 7
RSKRSRLLHSDYMNMTPRRPGPTRKHYQPYAPPRDFAAYRSRVKFSRSADAPAYQQGQNQ

LYNELNLGRREEYDVLDKRRGRDPEMGGKPRRKNPQEGLFNELQKDKMAEAFSEIGMKGE

RRRGKGHDGLFQGLSTATKDTFDALHMQALPPR
(153 a.a. CD28 co-stim + CD3ζITAM)
                                                      SEQ ID NO: 8
IEVMYPPPYLDNEKSNGTIIHVKGKHLCPSPLFPGPSKPFWVLVVVGGVLACYSLLVTVA

FIIFWVRSKRSRLLHSDYMNMTPRRPGPTRKHYQPYAPPRDFAAYRSRVKFSRSADAPAY

QQGQNQLYNELNLGRREEYDVLDKRRGRDPEMGGKPRRKNPQEGLFNELQKDKMAEAFSE

IGMKGERRRGKGHDGLFQGLSTATKDTFDALHMQALPPR
(219 a.a. CD28 hinge + CD28 TM + CD28 co-stim + CD3ζITAM)
```

In another embodiment, the CAR applicable to the cells provided in this application comprises a transmembrane domain derived from NKG2D, a co-stimulatory domain derived from 2B4, and a signaling domain comprising the native or modified CD3ζ, represented by an amino acid sequence of at least about 85%, about 90%, about 95%, about 96%, about 97%, about 98%, or about 99% identity to SEQ ID NO: 9. Said CAR comprising a transmembrane domain derived from NKG2D, a co-stimulatory domain derived from 2B4, and a signaling domain comprising the native or modified CD3ζ may further comprise a CD8 hinge, wherein the amino acid sequence of such a structure is of at least about 80%, about 85%, about 90%, about 95%, about 96%, about 97%, about 98%, or about 99% identity to SEQ ID NO: 10.

for example, U.S. Pat. No. 8,409,577), or a tandem CAR (see for example, Hegde et al., *J Clin Invest.* 2016; 126(8): 3036-3052); inducible CAR (see for example, U.S. Pub. Nos. 2016/0046700, 2016/0058857, 2017/0166877); switchable CAR (see for example, U.S. Pub. No: 2014/0219975); and any other designs known in the art.

Provided herein therefore includes derivative cells obtained from differentiating genomically engineered iPSCs, wherein both the iPSCs and the derivative cells comprise one or more CARs along with additional modified modalities, including, but not limited to, expression of an exogenous CD16. In one particular embodiment, the iPSC and its derivative cells comprises hnCD16, and a CAR targeting a selected tumor or viral antigen, wherein the derivative cells are NK or T lineage cells, and wherein the

```
                                                      SEQ ID NO: 9
SNLFVASWIAVMIIFRIGMAVAIFCCFFFPSWRRKRKEKQSETSPKEFLTIYEDVKDLKT

RRNHEQEQTFPGGGSTIYSMIQSQSSAPTSQEPAYTLYSLIQPSRKSGSRKRNHSPSFNS

TIYEVIGKSQPKAQNPARLSRKELENFDVYSRVKFSRSADAPAYKQGQNQLYNELNLGRR

EEYDVLDKRRGRDPEMGGKPRRKNPQEGLYNELQKDKMAEAYSEIGMKGERRRGKGHDGL

YQGLSTATKDTYDALHMQALPPR
(263 a.a NKG2D TM + 2B4 + CD3ζ)
                                                      SEQ ID NO: 10
TTTPAPRPPTPAPTIASQPLSLRPEACRPAAGGAVHTRGLDFACDSNRFVASWIAVMIIF

RIGMAVAIFCCFFFPSWRRKRKEKQSETSPKEFLTIYEDVKDLKTRRNHEQEQTFPGGGS

TIYSMIQSQSSAPTSQEPAYTLYSLIQPSRKSGSRKRNHSPSFNSTIYEVIGKSQPKAQN

PARLSRKELENFDVYSRVKFSRSADAPAYKQGQNQLYNELNLGRREEYDVLDKRRGRDPE

MGGKPRRKNPQEGLYNELQKDKMAEAYSEIGMKGERRRGKGHDGLYQGLSTATKDTYDAL

HMQALPPR
(308 a.a CD8 hinge + NKG2D TM + 2B4 + CD3ζ)
```

Non-limiting CAR strategies further include heterodimeric, conditionally activated CAR through dimerization of a pair of intracellular domains (see for example, U.S. Pat. No. 9,587,020); split CAR, where homologous recombination of antigen binding, hinge, and endodomains to generate a CAR (see for example, U.S. Pub. No. 2017/0183407); multi-chain CAR that allows non-covalent linking between two transmembrane domains connected to an antigen binding domain and a signaling domain, respectively (see for example, U.S. Pub. No. 2014/0134142); CARs having bispecific antigen binding domains (see for example, U.S. Pat. No. 9,447,194), or having a pair of antigen binding domains recognizing the same or different antigens or epitopes (see derivative cells may be used with, through hnCD16 binding, one or more ADCC antibodies or a bi-, tri- or multi-specific engager that targets a tumor antigen different from the one targeted by the CAR to avoid or to reduce tumor antigen escape while achieving dual targeting of the same tumor.

In a further embodiment, the iPSC and its derivative T lineage cells comprising a CAR have the CAR inserted in a TCR α or β constant region (TRAC or TRBC), leading to TCR knockout, and optionally placing CAR expression under the control of the endogenous TCR promoter. Additional CAR insertion sites include, but are not limited to, AAVS1, CCR5, ROSA26, collagen, HTRP, H11, GAPDH, RUNX1, B2M, TAP1, TAP2, tapasin, NLRC5, CIITA, RFXANK, RFX5, RFXAP, NKG2A, NKG2D, CD25, CD38, CD44, CD54, CD56, CD58, CD69, CD71, OX40, 4-1BB, CIS, CBL-B, SOCS2, PD1, CTLA4, LAGS, TIM3, and TIGIT. In some embodiments, derivative TCR negative CAR-T cells derived from engineered iPSCs further comprise exogenous CD16 having an ectodomain native to CD16 (F176V and/or S197P) or derived from CD64, and native or non-native transmembrane, stimulatory and signaling domains. In one particular embodiment of the iPSC derivative cell comprising TCR null and a CAR comprising one of the endodomains as provided, said derivative cell is a T lineage cell. In another embodiment, the iPSC and its derivative NK lineage cells comprising a CAR have the CAR inserted in the NKG2A locus or NKG2D locus, leading to NKG2A or NKG2D knock out, and optionally placing CAR expression under the control of the endogenous NKG2A or NKG2D promoter. In one particular embodiment of the iPSC derivative cell comprising NKG2A or NKG2D null and a CAR, said derivative cell is an NK lineage cell.

3. Exogenously Introduced Cytokine and/or Cytokine Signaling

By avoiding systemic high-dose administration of clinically relevant cytokines, the risk of dose-limiting toxicities due to such a practice is reduced while cytokine mediated cell autonomy being established. To achieve lymphocyte autonomy without the need to additionally administer soluble cytokines, a signaling complex comprising a partial or full length peptide of one or more of IL2, IL4, IL6, IL7, IL9, IL10, IL11, IL12, IL15, IL18, IL21, and/or their respective receptor is introduced to the cell to enable cytokine signaling with or without the expression of the cytokine itself, thereby maintaining or improving cell growth, proliferation, expansion, and/or effector function with reduced risk of cytokine toxicities. In some embodiments, the introduced cytokine and/or its respective native or modified receptor for cytokine signaling (signaling complex) are expressed on the cell surface. In some embodiments, the cytokine signaling is constitutively activated. In some embodiments, the activation of the cytokine signaling is inducible. In some embodiments, the activation of the cytokine signaling is transient and/or temporal.

Various construct designs for introducing a protein complex for signaling of cytokines including, but not limited to, IL2, IL4, IL6, IL7, IL9, IL10, IL11, IL12, IL15, IL18 and IL21, into the cell are provided herein.

FIG. 1 presents several construct designs using IL15 as an illustrative example. The transmembrane (TM) domain of any of the designs in FIG. 1 can be native to the IL15 receptor, or may be modified or replaced with transmembrane domain of any other membrane bound proteins.

Design 1: IL15 and IL15Rα are co-expressed by using a self-cleaving peptide, mimicking trans-presentation of IL15, without eliminating cis-presentation of IL15.

Design 2: IL15Rα is fused to IL15 at the C-terminus through a linker, mimicking trans-presentation without eliminating cis-presentation of IL15 as well as ensuring IL15 membrane-bound. The recombinant protein comprises an amino acid sequence at least about 85%, 90%, 91%, 92%, 93%, 94%, 95%, 96%, 97%, 98% or 99% identical to SEQ ID NO: 11, and the recombination protein comprises an IL15 pro-peptide downstream of a signal peptide. SEQ ID NO: 12 describes an exemplary DNA sequence encoding the amino acid sequence of SEQ ID NO: 11.

SEQ ID NO: 11
MDWTWILFLVAAATRVHSGIHVFILGCFSAGLPKTEANWVNVISDLKKIEDLIQSMHIDA

TLYTESDVHPSCKVTAMKCFLLELQVISLESGDASIHDTVENLIILANNSLSSNGNVTES

GCKECEELEEKNIKEFLQSFVHIVQMFINTSSGGGSGGGGSGGGGSGGGGSGGGSLQITC

PPPMSVEHADIWVKSYSLYSRERYICNSGFKRKAGTSSLTECVLNKATNVAHWTTPSLKC

IRDPALVHQRPAPPSTVTTAGVTPQPESLSPSGKEPAASSPSSNNTAATTAAIVPGSQLM

PSKSPSTGTTEISSHESSHGTPSQTTAKNWELTASASHQPPGVYPQGHSDTTVAISTSTV

LLCGLSAVSLLACYLKSRQTPPLASVEMEAMEALPVTWGTSSRDEDLENCSHHL
(414 a.a.)

SEQ ID NO: 12
ATGGACTGGACCTGGATTCTGTTCCTGGTCGCGGCTGCAACGCGAGTCCATAGCGGTATC

CATGTTTTTATTCTTGGGTGTTTTTCTGCTGGGCTGCCTAAGACCGAGGCCAACTGGGTA

AATGTCATCAGTGACCTCAAGAAAATAGAAGACCTTATACAAAGCATGCACATTGATGCT

ACTCTCTACACTGAGTCAGATGTACATCCCTCATGCAAAGTGACGGCCATGAAATGTTTC

CTCCTCGAACTTCAAGTCATATCTCTGGAAAGTGGCGACGCGTCCATCCACGACACGGTC

GAAAACCTGATAATACTCGCTAATAATAGTCTCTCTTCAAATGGTAACGTAACCGAGTCA

GGTTGCAAAGAGTGCGAAGAGTTGGAAGAAAAAAACATAAAGGAGTTCCTGCAAAGTTTC

GTGCACATTGTGCAGATGTTCATTAATACCTCTAGCGGCGGAGGATCAGGTGGCGGTGGA

AGCGGAGGTGGAGGCTCCGGTGGAGGAGGTAGTGGCGGAGGTTCTCTTCAAATAACTTGT

CCTCCACCGATGTCCGTAGAACATGCGGATATTTGGGTAAAATCCTATAGCTTGTACAGC

CGAGAGCGGTATATCTGCAACAGCGGCTTCAAGCGGAAGGCCGGCACAAGCAGCCTGACC

GAGTGCGTGCTGAACAAGGCCACCAACGTGGCCCACTGGACCACCCCTAGCCTGAAGTGC

```
ATCAGAGATCCCGCCCTGGTGCATCAGCGGCCTGCCCCTCCAAGCACAGTGACAACAGCT

GGCGTGACCCCCAGCCTGAGAGCCTGAGCCCTTCTGGAAAAGAGCCTGCCGCCAGCAGC

CCCAGCAGCAACAATACTGCCGCCACCACAGCCGCCATCGTGCCTGGATCTCAGCTGATG

CCCAGCAAGAGCCCTAGCACCGGCACCACCGAGATCAGCAGCCACGAGTCTAGCCACGGC

ACCCCATCTCAGACCACCGCCAAGAACTGGGAGCTGACAGCCAGCGCCTCTCACCAGCCT

CCAGGCGTGTACCCTCAGGGCACAGCGATACCACAGTGGCCATCAGCACCTCCACCGTG

CTGCTGTGTGGACTGAGCGCCGTGTCACTGCTGGCCTGCTACCTGAAGTCCAGACAGACC

CCTCCACTGGCCAGCGTGGAAATGGAAGCCATGGAAGCACTGCCCGTGACCTGGGGCACC

AGCTCGAGAGATGAGGATCTGGAAAACTGCTCCCACCACCTG
(1242 n.a.)
```

Design 3: IL15Rα with truncated intracellular domain is fused to IL15 at the C-terminus through a linker, mimicking trans-presentation of IL15, maintaining IL15 membrane-bound, and additionally eliminating cis-presentation and/or any other potential signal transduction pathways mediated by a normal IL15R through its intracellular domain. The intracellular domain of IL15Rα has been deemed as critical for the receptor to express in the IL15 responding cells, and for the responding cells to expand and function. Such a truncated construct comprises an amino acid sequence of at least 75%, 80%, 85%, 90%, 95% or 99% identity to SEQ ID NO: 13, which may be encoded by an exemplary nucleic acid sequence represented by SEQ ID NO: 14. In one embodiment of the truncated IL15/IL15Rα, the construct does not comprise the last 4 amino acid residues (KSRQ) of SEQ ID NO:13.

```
                                                         SEQ ID NO: 13
MDWTWILFLVAAATRVHSGIHVFILGCFSAGLPKTEANWVNVISDLKKIEDLIQSMHIDATLYT

ESDVHPSCKVTAMKCFLLELQVISLESGDASIHDTVENLIILANNSLSSNGNVTESGCKECEEL

EEKNIKEFLQSFVHIVQMFINTSSGGGSGGGGSGGGGSGGGGSGGGSLQITCPPPMSVEHADIW

VKSYSLYSRERYICNSGFKRKAGTSSLTECVLNKATNVAHWTTPSLKCIRDPALVHQRPAPPST

VTTAGVTPQPESLSPSGKEPAASSPSSNNTAATTAAIVPGSQLMPSKSPSTGTTEISSHESSHG

TPSQTTAKNWELTASASHQPPGVYPQGHSDTTVAISTSTVLLCGLSAVSLLACYLKSRQ
(379 a.a.; signal and linker peptides are underlined)
                                                         SEQ ID NO: 14
ATGGACTGGACCTGGATTCTGTTCCTGGTCGCGGCTGCAACGCGAGTCCATAGCGGTATCCATG

TTTTTATTCTTGGGTGTTTTTCTGCTGGGCTGCCTAAGACCGAGGCCAACTGGGTAAATGTCAT

GAGTGAGCTCAAGAAAATAGAAGACCTTATACAAAGCATGCACATTGATGCTAGTCTCTACACT

GAGTCAGATGTACATCCCTCATGCAAAGTGACGGCCATGAAATGTTTCCTCCTCGAACTTCAAG

TCATATCTCTGGAAAGTGGCGACGCGTCCATCCACGACACGGTCGAAAACCTGATAATACTCGC

TAATAATAGTCTCTCTTCAAATGGTAACGTAACCGAGTCAGGTTGCAAAGAGTGCGAAGAGTTG

GAAGAAAAAAACATAAAGGAGTTCCTGCAAAGTTTCGTGCACATTGTGCAGATGTTCATTAATA

CCTCTAGCGGCGGAGGATCAGGTGGCGGTGGAAGCGGAGGTGGAGGCTCCGGTGGAGGAGGTAG

TGGCGGAGGTTCTCTTCAAATAACTTGTCCTCCACCGATGTCCGTAGAACATGCGGATATTTGG

GTAAAATCCTATAGCTTGTACAGCCGAGAGCGGTATATCTGCAACAGCGGCTTCAAGCGGAAGG

CCGGCACAAGCAGCCTGACCGAGTGCGTGCTGAACAAGGCCACCAACGTGGCCCACTGGACCAC

CCCTAGCCTGAAGTGCATCAGAGATCCCGCCCTGGTGCATCAGCGGCCTGCCCCTCCAAGCACA

GTGACAACAGCTGGCGTGACCCCCAGCCTGAGAGCCTGAGCCCTTCTGGAAAAGAGCCTGCCG

CCAGCAGCCCCAGCAGCAACAATACTGCCGCCACCACAGCCGCCATCGTGCCTGGATCTCAGCT

GATGCCCAGCAAGAGCCCTAGCACCGGCACCACCGAGATCAGCAGCCACGAGTCTAGCCACGGC
```

```
ACCCCATCTCAGACCACCGCCAAGAACTGGGAGCTGACAGCCAGCGCCTCTCACCAGCCTCCAG

GCGTGTACCCTCAGGGCCACAGCGATACCACAGTGGCCATCAGCACCTCCACCGTGCTGCTGTG

TGGACTGAGCGCCGTGTCACTGCTGGCCTGCTACCTGAAGTCCAGACAGTGA
(1140 n.a.)
```

One having ordinary skill in the art would appreciate that the signal peptide and the linker sequences above are illustrative and in no way limit their variations suitable for use as a signal peptide or linker. There are many suitable signal peptide or linker sequences known and available to those skilled in the art, and one skilled in the art understands that the signal peptide and/or linker sequences may be substituted for another sequence without altering the activity of the functional peptide led by the signal peptide or linked by the linker.

Design 4: Since the Design 3 construct was shown to be functional in promoting effector cell survival and expansion, demonstrating that the cytoplasmic domain of IL15Rα can be omitted without negatively impacting the autonomous feature of the effector cell equipped with IL15 in such a design, Design 4 is a construct providing another working alternative of Design 3, from which essentially the entire IL15Rα is removed except for the Sushi domain, fused with IL15 at one end and a transmembrane domain on the other (mb-Sushi), optionally with a linker between the Sushi domain and the trans-membrane domain. The fused IL5/mb-Sushi is expressed at the cell surface through the transmembrane domain of any membrane bound protein. With a construct such as Design 4, unnecessary signaling through IL15Rα, including cis-presentation, is eliminated when only the desirable trans-presentation of IL15 is retained. In some embodiments, the component comprising IL15 fused with the Sushi domain comprises an amino acid sequence of at least 75%, 80%, 85%, 90%, 95% or 99% identity to SEQ ID NO: 15, which may be encoded by an exemplary nucleic acid sequence represented by SEQ ID NO: 16.

```
                                                      SEQ ID NO: 15
MDWTWILFLVAAATRVHSGIHVFILGCFSAGLPKTEANWVNVISDLKKIEDLIQSMHIDATLYT

ESDVHPSCKVTAMKCFLLELQVISLESGDASIHDTVENLIILANNSLSSNGNVTESGCKECEEL

EEKNIKEFLQSFVHIVQMFINTSSGGGSGGGGSGGGGSGGGGSGGGSLQITCPPPMSVEHADIW

VKSYSLYSRERYICNSGFKRKAGTSSLTECVLNKATNVAHWTTPSLKCIR
(242 a.a.; signal and linker peptides are underlined)
                                                      SEQ ID NO: 16
ATGGACTGGACCTGGATTCTGTTCCTGGTCGCGGCTGCAACGCGAGTCCATAGCGGTATCCATG

TTTTTATTCTTGGGTGTTTTTCTGCTGGGCTGCCTAAGACCGAGGCCAACTGGGTAAATGTCAT

CAGTGAGCTCAAGAAAATAGAAGACCTTATACAAAGCATGCACATTGATGCTAGTCTCTACACT

GAGTCAGATGTACATCCCTCATGCAAAGTGACGGCCATGAAATGTTTCCTCCTCGAACTTCAAG

TCATATCTCTGGAAAGTGGCGACGCGTCCATCCACGACACGGTCGAAAACCTGATAATACTCGC

TAATAATAGTCTCTCTTCAAATGGTAACGTAACCGAGTCAGGTTGCAAAGAGTGCGAAGAGTTG

GAAGAAAAAACATAAAGGAGTTCCTGCAAAGTTTCGTGCACATTGTGCAGATGTTCATTAATA

CCTCTAGCGGCGGAGGATCAGGTGGCGGTGGAAGCGGAGGTGGAGGCTCCGGTGGAGGAGGTAG

TGGCGGAGGTTCTCTTCAAATAACTTGTCCTCCACCGATGTCCGTAGAACATGCGGATATTTGG

GTAAAATCCTATAGCTTGTACAGCCGAGAGCGGTATATCTGCAACAGCGGCTTCAAGCGGAAGG

CCGGCACAAGCAGCCTGACCGAGTGCGTGCTGAACAAGGCCACCAACGTGGCCCACTGGACCAC

CCCTAGCCTGAAGTGCATCAGA
(726 n.a.)
```

One having ordinary skill in the art would appreciate that the signal peptide and the linker sequences above are illustrative and in no way limit their variations suitable for use as a signal peptide or linker. There are many suitable signal peptide or linker sequences known and available to those in the art, and one skilled in the art understands that the signal peptide and/or linker sequences may be substituted for another sequence without altering the activity of the functional peptide led by the signal peptide or linked by the linker.

Design 5: A native or modified IL15β is fused to IL15 at the C-terminus through a linker, enabling constitutive signaling and maintaining IL15 membrane-bound and trans-representation.

Design 6: A native or modified common receptor γC is fused to IL15 at the C-terminus through a linker for constitutive signaling and membrane bound trans-presentation of the cytokine. The common receptor γC is also called the common gamma chain or CD132, also known as IL2 receptor subunit gamma or IL2RG. γC is a cytokine receptor sub-unit that is common to the receptor complexes for many interleukin receptors, including, but not limited to, IL2, IL4, IL7, IL9, IL15 and IL21 receptor.

Design 7: Engineered IL15β that forms a homodimer in absence of IL15 is useful for producing constitutive signaling of the cytokine.

In some embodiments, one or more of cytokines IL2, IL4, IL6, IL7, IL9, IL10, IL11, IL12, IL15, IL18 and IL21, and/or receptors thereof, may be introduced to iPSC using one or more of the designs shown in FIG. 1, and to its derivative cells upon iPSC differentiation. In some embodiments, IL2 or IL15 cell surface expression and signaling is through the construct illustrated in any one of Designs 1-7. In some embodiments, IL4, IL7, IL9, or IL21 cell surface expression and signaling is through the construct illustrated in Design 5, 6, or 7, by using either a common receptor or a cytokine specific receptor. In some embodiments, IL7 surface expression and signaling is through the construct illustrated in Design 5, 6, or 7, by using either a common receptor or a cytokine specific receptor, such as an IL4 receptor. The transmembrane (TM) domain of any of the designs in FIG. 1 can be native to a respective cytokine receptor, or may be modified or replaced with a transmembrane domain of any other membrane bound proteins.

In iPSCs and derivative cells therefrom comprising both CAR and exogenous cytokine and/or cytokine receptor signaling (signaling complex, or "IL"), the CAR and IL may be expressed in separate constructs, or may be co-expressed in a bi-cistronic construct comprising both CAR and IL. In some further embodiments, the signaling complex is in a form represented by any of the construct designs in FIG. 1 and can be linked to either the 5' or the 3' end of a CAR expression construct through a self-cleaving 2A coding sequence, illustrated as, for example, CAR-2A-IL15 or IL15-2A-CAR. As such, the IL15 and CAR are in a single open reading frame (ORF). In one embodiment, the CAR-2A-IL15 or IL15-2A-CAR construct comprises IL15 as shown in Design 3 of FIG. 1. In another embodiment, the CAR-2A-IL15 or IL15-2A-CAR construct comprises IL15 as shown in Design 4 of FIG. 1. In yet another embodiment, the CAR-2A-IL15 or IL15-2A-CAR construct comprises IL15 as shown in Design 7 of FIG. 1. When CAR-2A-IL15 or IL15-2A-CAR is expressed, the self-cleaving 2A peptide allows the expressed CAR and IL15 dissociate, and the dissociated IL15 can then be presented at cell surface. The CAR-2A-IL15 or IL15-2A-CAR bi-cistronic design allows a coordinated CAR and IL15 expression both in timing and quantity, and under the same control mechanism that may be chosen to incorporate, for example, an inducible promoter for the expression of the single ORF. Self-cleaving peptides are found in members of the Picornaviridae virus family, including aphthoviruses such as foot-and-mouth disease virus (FMDV), equine rhinitis A virus (ERAV), Thosea asigna virus (TaV) and porcine tescho virus-1 (PTV-I) (Donnelly, M L, et al, J. Gen. Virol, 82, 1027-101 (2001); Ryan, M D, et al., J. Gen. Virol., 72, 2727-2732 (2001)), and cardioviruses such as Theilovirus (e.g., Theiler's murine encephalomyelitis) and encephalomyocarditis viruses. The 2A peptides derived from FMDV, ERAV, PTV-I, and TaV are sometimes also referred to as "F2A", "E2A", "P2A", and "T2A", respectively.

The bi-cistronic CAR-2A-IL15 or IL15-2A-CAR embodiment as disclosed herein for IL15 is also contemplated for expression of any other cytokine provided herein, for example, IL2, IL4, IL6, IL7, IL9, IL10, IL11, IL12, IL18, and IL21. In some embodiments, IL2 cell surface expression and signaling is through the construct illustrated in any of the Designs 1-7. In some other embodiments, IL4, IL7, IL9, or IL21 cell surface expression and signaling is through the construct illustrated in Design 5, 6, or 7, either using a common receptor and/or a cytokine specific receptor.

In some embodiments, the iPSC, and its derivative effector cells comprising a genotype that comprises one or more attributes including $CAR^+$, $IL^+$ and $CD16^+$ may further comprise any one of the additional attributes in Table 1, including one or more of $lig^-$ (ligand negative), $inR^+$ (inactivation CAR positive), $cs\text{-}CD3^+$ (cell surface CD3 positive), $En^+$ (engager positive), and $Ab^+$ (antibody or checkpoint inhibitor positive).

4. Inactivation CAR and Alloantigen

CAR, a chimerical antigen receptor, as described previously herein, is a fusion protein generally including an ectodomain that comprises an antigen recognition region, a transmembrane domain, and an endo-domain. In some embodiments, the ectodomain can further include a signal peptide or leader sequence and/or a spacer. In some embodiments, the endodomain can further comprise a signaling peptide that activates the effector cell expressing the CAR. Here, "inactivating CAR", abbreviated as $inR^+$ in Table 1, is an antagonistic CAR comprising a binding domain specific to an upregulated surface protein (also referred to as alloantigen or ligand herein, abbreviated as $lig^-$ in Table 1) that is expressed on activated, or alloreactivated, T, B or NK cells, thereby eliminating or reducing such cells. Expressing such inactivating CAR in a synthetic effector cell derived from engineered iPSC is a solution for allogeneic rejection control in the off-the-shelf allogeneic adoptive cell therapy setting using said derivative effector cells.

It is believed that multiple HLA class I and class II proteins must be matched for histocompatibility in allogeneic recipients to avoid allogeneic rejection problems. Without MHC matching, one approach that has been investigated in allogeneic adoptive cell therapy is to eliminate or substantially reduce the expression of both HLA class I and HLA class II proteins. HLA class I deficiency can be achieved by functional deletion of any region of the HLA class I locus (chromosome 6p21), or by deleting or reducing the expression level of HLA class-I associated genes including, but not limited to, beta-2 microglobulin (B2M) gene, TAP1 gene, TAP2 gene and Tapasin. For example, the B2M gene encodes a common subunit essential for cell surface expression of all HLA class I heterodimers. B2M null cells are HLA-I deficient. HLA class II deficiency can be achieved by functional deletion or reduction of HLA-II associated genes including, but not limited to, RFXANK, CIITA, RFX5 and RFXAP. CIITA is a transcriptional coactivator, functioning through activation of the transcription factor RFX5 required for class II protein expression. CIITA null cells are HLA-II deficient. However, lacking HLA class I expression increases susceptibility to lysis by NK cells. Further, deficiency in both HLA-I and HLA-II still does not prevent allorejection mediated by alloantigens other than the MEW of the allogeneic adoptive cells. Moreover, HLA-I-dependent NK cell education processes, such as licensing, arming, or disarming are believed to have an impact on innate immune responsiveness toward allogeneic cells that may cause reactivity, or partial reactivity, of recipient NK cells against allogeneic donor cells, even when those donor cells are HLA-I sufficient.

The upregulated surface proteins/ligands of alloreactivated cells include, but are not limited to, CD40L, OX40, and 4-1BB. As such, the corresponding inactivation-CAR includes a CD40L-CAR, OX40-CAR, or a 4-1BB-CAR. Therefore, to keep HLA-I, or HLA-II, or both intact in allogeneic effector cells (i.e., comprising HLA-I wildtype, or HLA-II wildtype, or both) while avoiding allorejection by eliminating or reducing activated T, B cells and NK cells in the recipient of one or more synthetic effector cells derived from an engineered iPSC, the iPSC and effector cells derived therefrom as provided herein may comprise at least one inactivation-CAR. Further, to avoid fratricide among the inactivation-CAR expressing effector cell population, in some embodiments, the iPSC and effector cells derived therefrom are further negative in the surface protein specifically targeted by said inactivation-CAR, thus having a genotype such as, CD40L-CAR/CD40L$^-$, OX40-CAR/OX40$^-$, or 4-1BB-CAR/4-1BB$^-$. In some other embodiments, the iPSC and effector cells derived therefrom are only negative in the surface protein without the corresponding inactivation-CAR, and such cells can be used in combination with an antibody against said surface proteins of reactive cells without eliminating the effector cells.

5. Cell Surface Presentation of CD3 in TCR Negative Cells

Disrupting the constant region of TCR alpha or TCR beta (TRAC or TRBC), either through direct editing of a T cell or through iPSC editing as a source for obtaining modified derivative T lineage cells, is one of the approaches to produce a TCR$^{neg}$ T cell. For example, an insertion of a 2A sequence, at a pre-selected position in TRAC or TRBC, either operatively linked to an endogenous promoter of the TRAC or TRBC or to an exogenous promoter, can lead to TRAC or TRBC disruption (or truncation in this example) and a TCR negative cell (TCR$^{neg}$). In some embodiments, the targeted truncation or disruption using a self-cleaving peptide such as 2A could optionally take place concomitantly with integration of one or more exogenous genes of interest at the location of truncation or disruption, and the expression of the integrated gene(s) could be driven by an operatively linked exogenous promoter or by an endogenous promoter of TCR alpha or TCR beta upon integration, which leads to TRAC or TRBC knockout, and thus TCR$^{neg}$ while expressing one or more exogenous genes inserted at the TRAC or TRBC locus.

In a particular embodiment, the TCR$^{neg}$ cell is an iPSC. In another embodiment, the TCR$^{neg}$ cell is an NK lineage cell. As used herein, the term "TCR negative" or "TCR$^{neg}$" refers to the lack of endogenous TCR expression, either due to disruption of TCR gene expression (such as in T lineage cells: primary or iPSC-derived T lineage cells) or due to a natural absence of TCR gene expression despite the existence of a TCR locus in the genome (for example, iPSCs, or NK linage cells: primary or iPSC-derived NK lineage cells). The subsequent directed differentiation of clonally selected engineered iPSC to hematopoietic cells make it possible to generate iPSC-derived immune effector cells, and/or a homogenous population thereof, without TCR expression.

iPSC-derived TCR negative T lineage cells (with or without exogenous gene integration) obtained using this approach do not require HLA matching, have reduced alloreactivity and are able to prevent GvHD (Graft versus Host Disease) when used in allogeneic adoptive cell therapies. However, it has been found that TCR disruption also results in the elimination of the CD3 signaling complex from the T cell surface despite the CD3 subunit gene expression in the cell. The lack of cell surface CD3 may alter the cells' capacity for expansion and/or survival and reduce the cells' functional potential due to incompatibility with technologies requiring cell surface CD3 recognition and binding, which include, but are not limited to: BiTE, BiKE, or TRiKE (or collectively called, engager) technology; CD3/CD28 T cell activation bead technology; and anti-CD3 antibody or CD3-CAR stimulation technology. For cells that do not express TCR despite the existence of TCR genes, for example, NK or NK progenitor cells, the cell surface CD3 complex, or one or more subunits or subdomains thereof (cs-CD3) can function as cell surface triggering receptors for binding with molecules including, but not limited to, antibodies or functional variants thereof, and/or bi- or multi-specific engagers recognizing cell surface CD3. Applicable constructs and genomic editing methods and compositions for obtaining cs-CD3$^+$ iPSC and iPSC-derived effector cells are described in greater detail in International Pub. No. WO2020/210398, the complete disclosure of which is incorporated herein by reference.

6. Engager

Engagers are fusion proteins consisting of two or more single-chain variable fragments (scFvs), or other functional variants, of different antibodies or fragments thereof, with at least one scFv that binds to an effector cell surface molecule or surface triggering receptor, and at least another to a target cell via a target cell specific surface molecule. Examples of engagers include, but are not limited to, bi-specific T cell engagers (BiTEs), bi-specific killer cell engagers (BiKEs), tri-specific killer cell engagers (TriKEs), multi-specific killer cell engagers, or universal engagers compatible with multiple immune cell types. Engagers can be bispecific or multi-specific. Such bispecific or multi-specific engagers are capable of directing an effector cell (e.g., a T cell, a NK cell, an NKT cell, a B cell, a macrophage, and/or a neutrophil) to a tumor cell and activating the immune effector cell, and have shown great potential to maximize the benefits of CAR-T cell therapy.

In some embodiments, the engager is used in combination with a population of synthetic effector cells by concurrent or consecutive administration, wherein the synthetic effector cells comprise a surface molecule, or surface triggering receptor, that is recognized by the engager. In some other embodiments, the engager is a bispecific antibody expressed by a synthetic effector cell through genetically engineering an iPSC and directed differentiation of the engineered iPSC. Exemplary effector cell surface molecules, or surface triggering receptors, that can be used for bi- or multi-specific engager recognition, or coupling thereof, include, but are not limited to, CD3, CD28, CD5, CD16, NKG2D, CD64, CD32, CD89, NKG2C, and a chimeric Fc receptor as disclosed herein. In some embodiments, the exogenous CD16 expressed on the surface of the synthetic effector cells for engager recognition is a hnCD16, comprising a CD16 (containing F176V and optionally S197P) or a CD64 extracellular domain, and native or non-native transmembrane, stimulatory and/or signaling domains as described herein. In some embodiments, the CD16 expressed on the surface of effector cells for engager recognition is a CD16-based chimeric Fc receptor (CFcR). In some embodiments, the CD16-based CFcR comprises a transmembrane domain of NKG2D, a stimulatory domain of 2B4, and a signaling domain of CD3; wherein the extracellular domain of the CD16 is derived from a full length or partial sequence of the extracellular domain of CD64 or CD16; and wherein the extracellular domain of CD16 comprises F176V and optionally S197P.

In some embodiments, the target cell for an engager is a tumor cell. The exemplary tumor cell surface molecules for bi- or multi-specific engager recognition include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, ROR1. In one embodiment, the bispecific engager is a bispecific antibody specific to CD3 and CD19 (CD3-CD19). In another embodiment, the bispecific antibody is CD16-CD30 or CD64-CD30. In another embodiment, the bispecific antibody is CD16-BCMA or CD64-BCMA. In still another embodiment, the bispecific antibody is CD3-CD33.

In yet another embodiment, the bispecific antibody further comprises a linker between the effector cell and tumor cell antigen binding domains. For example, a modified IL15 is used as a linker for effector NK cells to facilitate cell expansion (called TriKE, or Tri-specific Killer Engager, in some publications). In one embodiment, the TriKE is CD16-IL15-EPCAM or CD64-IL15-EPCAM. In another embodiment, the TriKE is CD16-IL15-CD33 or CD64-IL15-CD33. In yet another embodiment, the TriKE is NKG2C-IL15-CD33. The IL15 in the TriKE may also originate from other cytokines including, but not limited to, IL2, IL4, IL6, IL7, IL9, IL10, IL11, IL12, IL18, and IL21.

In some embodiments, the surface triggering receptor for bi- or multi-specific engager could be endogenous to the effector cells, sometimes depending on the cell types. In some other embodiments, one or more exogenous surface triggering receptors could be introduced to the effector cells using the methods and compositions provided herein, e.g., through additional engineering of an iPSC comprising a genotype listed in Table 1, then directing the differentiation of the iPSC to T, NK or any other effector cells comprising the same genotype and the surface triggering receptor as the source iPSC.

7. Antibodies for Immunotherapy

In some embodiments, in addition to the genomically engineered effector cells as provided herein, additional therapeutic agents comprising an antibody, or an antibody fragment that targets an antigen associated with a condition, a disease, or an indication may be used with these effector cells in a combinational therapy. In some embodiments, the antibody is used in combination with a population of synthetic effector cells by concurrent or consecutive administration to a subject. In some other embodiments, such antibody or a fragment thereof may be expressed by the effector cells by genetically engineering an iPSC using an exogenous polynucleotide sequence encoding said antibody, or a fragment thereof, and directed differentiation of the engineered iPSC. In some embodiments, the effector cell expresses a CD16 variant, wherein the cytotoxicity of the effector cell is enhanced by the antibody via ADCC. In some embodiments, the antibody is a monoclonal antibody. In some embodiments, the antibody is a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC-derived effector cells to enhance their killing ability. In some embodiments, the antibodies suitable for combinational treatment as an additional therapeutic agent to the administered iPSC-derived effector cells include, but are not limited to, anti-CD20 (rituximab, veltuzumab, ofatumumab, ublituximab, ocaratuzumab, obinutuzumab), anti-HER2 (trastuzumab, pertuzumab), anti-CD52 (alemtuzumab), anti-EGFR (certuximab), anti-GD2 (dinutuximab), anti-PDL1 (avelumab), anti-CD38 (daratumumab, isatuximab, MOR202), anti-CD123 (7G3, CSL362), anti-SLAMF7 (elotuzumab); and their humanized or Fc modified variants or fragments, or their functional equivalents and biosimilars.

8. Checkpoint Inhibitors

Checkpoints are cell molecules, often cell surface molecules, capable of suppressing or downregulating immune responses when not inhibited. It is now clear that tumors co-opt certain immune-checkpoint pathways as a major mechanism of immune resistance, particularly against T cells that are specific for tumor antigens. Checkpoint inhibitors (CIs) are antagonists capable of reducing checkpoint gene expression or gene products, or decreasing activity of checkpoint molecules, thereby blocking inhibitory checkpoints, and restoring immune system function. The development of checkpoint inhibitors targeting PD1/PDL1 or CTLA4 has transformed the oncology landscape, with these agents providing long term remissions in multiple indications. However, many tumor subtypes are resistant to checkpoint blockade therapy, and relapse remains a significant concern. One aspect of the present application provides a therapeutic approach to overcome CI resistance by including genomically-engineered functional derivative cells as provided in a combination therapy with CI. In some embodiments, the checkpoint inhibitor is used in combination with a population of synthetic effector cells by concurrent or consecutive administration to a subject. In some other embodiments, the checkpoint inhibitor is expressed by the effector cells by genetically engineering an iPSC using an exogenous polynucleotide sequence encoding said checkpoint inhibitor, or a fragment or variant thereof, and directed differentiation of the engineered iPSC.

In some embodiments, the exogenous polynucleotide sequence encoding the checkpoint inhibitor, or a fragment thereof is co-expressed with a CAR, either in separate constructs or in a bi-cistronic construct. In some further embodiments, the sequence encoding the checkpoint inhibitor or the fragment thereof can be linked to either the 5' or the 3' end of a CAR expression construct through a self-cleaving 2A coding sequence, illustrated as, for example, CAR-2A-CI or CI-2A-CAR. As such, the coding sequences of the checkpoint inhibitor and the CAR are in a single open reading frame (ORF). When the checkpoint inhibitor is delivered, expressed and secreted as a payload by the derivative effector cells capable of infiltrating the tumor microenvironment (TME), it counteracts the inhibitory checkpoint molecule upon engaging the TME, allowing activation of the effector cells by activating modalities such as CAR or activating receptors. In one embodiment of the combination therapy, the derivative cells are NK lineage cells. In another embodiment of the combination therapy, the derivative cells are T lineage cells.

Suitable checkpoint inhibitors for combination therapy with the derivative NK lineage cells or T lineage cells as provided herein include, but are not limited to, antagonists of PD-1 (Pdcd1, CD279), PDL-1 (CD274), TIM-3 (Havcr2), TIGIT (WUCAM and Vstm3), LAG-3 (Lag3, CD223), CTLA-4 (Ctla4, CD152), 2B4 (CD244), 4-1BB (CD137), 4-1BBL (CD137L), $A_{2A}R$, BATE, BTLA, CD39 (Entpd1), CD47, CD73 (NT5E), CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

In some embodiments, the antagonist inhibiting any of the above checkpoint molecules is an antibody. In some embodiments, the checkpoint inhibitory antibodies may be murine antibodies, human antibodies, humanized antibodies, a camel Ig, a shark heavy-chain-only antibody (VNAR), Ig NAR, chimeric antibodies, recombinant antibodies, or antibody fragments thereof. Non-limiting examples of antibody fragments include Fab, Fab', F(ab')2, F(ab')3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the checkpoint inhibitors comprise at least one of atezolizumab (anti-PDL1 mAb), avelumab (anti-PDL1 mAb), durvalumab (anti-PDL1 mAb), tremelimumab (anti-CTLA4 mAb), ipilimumab (anti-CTLA4 mAb), IPH4102 (anti-KIR), IPH43 (anti-MICA), IPH33 (anti-TLR3), lirimumab (anti-KIR), monalizumab (anti-NKG2A), nivolumab (anti-PD1 mAb), pembrolizumab (anti-PD1 mAb), and any derivatives, functional equivalents, or biosimilars thereof.

In some embodiments, the antagonist inhibiting any of the above checkpoint molecules is microRNA-based, as many miRNAs are found as regulators that control the expression of immune checkpoints (Dragomir et al., Cancer Biol Med. 2018, 15(2):103-115). In some embodiments, the checkpoint antagonistic miRNAs include, but are not limited to, miR-28, miR-15/16, miR-138, miR-342, miR-20b, miR-21, miR-130b, miR-34a, miR-197, miR-200c, miR-200, miR-17-5p, miR-570, miR-424, miR-155, miR-574-3p, miR-513, and miR-29c.

In some embodiments, the checkpoint inhibitor co-expressed with CAR inhibits at least one of the checkpoint molecules: PD-1, PDL-1, TIM-3, TIGIT, LAG-3, CTLA-4, 2B4, 4-1BB, 4-1BBL, $A_{2A}R$, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR. In some embodiments, the checkpoint inhibitor co-expressed with CAR in a derivative cell having a genotype listed in Table 1 is selected from a group comprising atezolizumab, avelumab, durvalumab, tremelimumab, ipilimumab, IPH4102, IPH43, IPH33, lirimumab, monalizumab, nivolumab, pembrolizumab, and their humanized, or Fc modified variants, fragments and their functional equivalents or biosimilars. In some embodiments, the checkpoint inhibitor co-expressed with CAR is atezolizumab, or its humanized, or Fc modified variants, fragments or their functional equivalents or biosimilars. In some other embodiments, the checkpoint inhibitor co-expressed with CAR is nivolumab, or its humanized, or Fc modified variants, fragments or their functional equivalents or biosimilars. In some other embodiments, the checkpoint inhibitor co-expressed with CAR is pembrolizumab, or its humanized, or Fc modified variants, fragments or their functional equivalents or biosimilars.

In some other embodiments of the combination therapy comprising the derivative cells provided herein and at least one antibody inhibiting a checkpoint molecule, said antibody is not produced by, or in, the derivative cells and is additionally administered before, with, or after the administering of the derivative cells as provided herein. In some embodiments, the administering of one, two, three or more checkpoint inhibitors in a combination therapy with the provided derivative NK lineage cells or T lineage cells are simultaneous or sequential. In one embodiment of the combinational treatment comprising derived NK lineage cells or T lineage cells, the checkpoint inhibitor included in the treatment is one or more of atezolizumab, avelumab, durvalutnab, tremelimumab, ipilimumab, IPH4102, IPH43, IPH33, lirimumab, monalizumab, nivolumab, pembrolizumab, and their humanized or Fc modified variants, fragments and their functional equivalents or biosimilars. In some embodiments of the combination treatment comprising derived NK cells or T cells, the checkpoint inhibitor included in the treatment is atezolizumab, or its humanized or Fc modified variant, fragment and its functional equivalent or biosimilar. In some embodiments of the combination treatment comprising derived NK lineage cells or T lineage cells, the checkpoint inhibitor included in the treatment is nivolumab, or its humanized or Fc modified variant, fragment or its functional equivalent or biosimilar. In some embodiments of the combination treatment comprising derived NK lineage cells or T lineage cells, the checkpoint inhibitor included in the treatment is pembrolizumab, or its humanized or Fc modified variant, fragment or its functional equivalent or biosimilar.

9. Genetically Engineered iPSC Line and Derivative Cells Provided Herein

In light of the above, the present application provides an iPSC, an iPS cell line cell, or a derivative cell therefrom comprising an exogenous polynucleotide encoding at least a CAR, and optionally exogenous polynucleotides encoding one or both of exogenous CD16 and a cytokine and/or its receptor (IL) variant (CAR(CD16/IL) in Table 1), wherein the derivative cells are functional effector cells obtained from differentiation of an engineered iPSC comprising exogenous polynucleotides encoding a CAR, and one or both of an exogenous CD16 and an IL. In some embodiments, the derivative cells are hematopoietic lineage cells including, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages. In some embodiments, the functional derivative hematopoietic cells comprise effector cells such as T, NK, and regulatory cells.

In some embodiments, the derivative cells comprise NK or T lineage cells. iPSC-derived NK or T lineage cells comprising both exogenous CD16 and CAR are useful for overcoming or reducing tumor relapse associated with tumor antigen escape observed in CAR-T only therapies by combining an antibody with a CAR targeted treatment, provided that the antibody and the CAR have specificity to different antigens of the tumor. Derivative CAR-T cells expressing hnCD16 have acquired ADCC, providing an additional mechanism for tumor killing in addition to CAR targeting. In some embodiments, the derivative cells comprise NK lineage cells. iPSC-derived NK cells comprising hnCD16 and CAR have enhanced cytotoxicity, are effective in recruiting by-stander cells including T cells to infiltrate and kill tumor cells.

Additionally provided is an iPSC, an iPS cell line cell, or a derivative cell therefrom comprising a polynucleotide encoding an exogenous CD16, a polynucleotide encoding a CAR, and a polynucleotide encoding at least one exogenous cytokine and/or its receptor (IL) to enable cytokine signaling contributing to cell survival, persistence and/or expansion, wherein the iPSC line is capable of directed differentiation to produce functional derivative hematopoietic lineage cells having improved survival, persistency, expansion, and effector cell function. The exogenously introduced cytokine signaling(s) comprise the signaling of any one, two, or more of IL2, IL4, IL6, IL7, IL9, IL10, IL11, IL12, IL15, IL18, and IL21.

In some embodiments, the introduced partial or full cytokine and/or its respective receptor for cytokine signaling are expressed on the cell surface. In some embodiments, the cytokine signaling is constitutively activated. In some embodiments, the activation of the cytokine signaling is inducible. In some embodiments, the activation of the cytokine signaling is transient and/or temporal. In some embodiments, the transient/temporal expression of a cell surface cytokine/cytokine receptor is through a retrovirus, Sendai virus, an adenovirus, an episome, mini-circle, or RNAs including mRNA.

In some embodiments, the exogenous cell surface cytokine and/or receptor comprised in the hnCD16/CAR iPSC or derivative cells therefrom enables IL7 signaling. In some embodiments, the exogenous cell surface cytokine and/or receptor comprised in the hnCD16/CAR iPSC or derivative cells therefrom enables IL10 signaling. In some embodiments, the exogenous cell surface cytokine and/or receptor comprised in the hnCD16/CAR iPSC or derivative cells therefrom enables IL15 signaling. In some embodiments of said hnCD16/CAR/IL iPSC, the IL15 expression is through Design 3 of FIG. 1. In some embodiments of said hnCD16/CAR/IL iPSC, the IL15 expression is through Design 4 of FIG. 1. Thus, said hnCD16/CAR/IL iPSC and its derivative cells of the above embodiments are capable of maintaining or improving cell growth, proliferation, expansion, and/or effector function autonomously without contacting additionally supplied soluble cytokines in vitro or in vivo. In some embodiments, the hnCD16/CAR/IL iPSC and its derivative effector cells can be used with an antibody to induce ADCC to synergize with CAR targeted tumor killing by reducing or eliminating tumor antigen escape and the subsequent tumor relapse.

In some embodiments, the iPSC-derived effector cells comprise hematopoietic lineage cells comprising an exogenous polynucleotide encoding at least a CAR, and optionally exogenous polynucleotides encoding one or both of hnCD16 and a cytokine and/or its receptor (IL) variant (CAR(CD16/IL) in Table 1), and may further comprise one or more of attributes comprising lig⁻, inR⁺, cs-CD3⁺, En⁺, and Ab⁺, respectively, alloantigen knock out, inactivation CAR expression, cell-surface CD3 expression, engager expression, and antibody expression. In some embodiments, the iPSC-derived effector cells comprise CAR(CD16/IL) iNK cells further comprising a genotype listed in Table 1. In some embodiments, the iPSC-derived effector cells comprise CAR(CD16/IL) iT cells further comprising a genotype listed in Table 1.

In some other embodiments, the iPSC-derived effector cells comprising an exogenous polynucleotide encoding at least a CAR, and optionally exogenous polynucleotides encoding one or both of hnCD16 and a cytokine and/or its receptor (IL), and one or more of the attributes comprising lig⁻, inR⁺, cs-CD3⁺, En⁺, and Ab⁺ (see Table 1), may additionally comprise HLA-I and/or HLA-II deficiency.

Multiple HLA class I and class II proteins must be matched for histocompatibility in allogeneic recipients to avoid allogeneic rejection problems. Provided herein is an iPSC cell line and its derivative cells differentiated therefrom with eliminated or substantially reduced expression of both HLA class I and HLA class II proteins. HLA class I deficiency can be achieved by functional deletion of any region of the HLA class I locus (chromosome 6p21), or deletion or reducing the expression level of HLA class I associated genes including, but not limited to, beta-2 microglobulin (B2M) gene, TAP 1 gene, TAP 2 gene and Tapasin. For example, the B2M gene encodes a common subunit essential for cell surface expression of all HLA class I heterodimers. B2M negative cells are HLA-I deficient. HLA class II deficiency can be achieved by functional deletion or reduction of HLA-II associated genes including, but not limited to, RFXANK, CIITA, RFX5 and RFXAP. CIITA is a transcriptional coactivator, functioning through activation of the transcription factor RFX5 required for class II protein expression. CIITA negative cells are HLA-II deficient.

For some cell types, a lack of HLA class I expression leads to lysis by NK cells. To overcome this "missing self" response, HLA-G may be optionally knocked-in to avoid NK cell recognition and killing of the HLA-I deficient effector cells derived from an engineered iPSC. In one embodiment, the HLA-I deficient iPSC and its derivative cells further comprise HLA-G knock-in. In some embodiments, the provided HLA-I deficient iPSC and its derivative cells further comprise one or both of CD58 knockout and CD54 knock-out. CD58 (or LFA-3) and CD54 (or ICAM-1) are adhesion proteins initiating signal-dependent cell interactions, and facilitating cell, including immune cell, migration. It was shown that CD58 knock-out has a higher efficiency in reducing allogeneic NK cell activation than CD54 knock-out; while double knock-out of both CD58 and CD54 has the most enhanced reduction of NK cell activation. In some observations, the CD58 and CD54 double knock-out is even more effective than HLA-G overexpression for HLA-I deficient cells in overcoming "missing-self" effect. As provided herein, in some embodiments, the HLA-I and HLA-II deficient iPSC and its derivative cells have an exogenous polynucleotide encoding HLA-G. In some embodiments, the HLA-I and HLA-II deficient iPSC and its derivative cells are CD58 null. In some other embodiments, the HLA-I and HLA-II deficient iPSC and its derivative cells are CD54 null. In yet some other embodiments, the HLA-I and HLA-II deficient iPSC and its derivative cells are CD58 null and CD54 null. A cell bank provides a platform for additional iPSC engineering, and a renewable source for manufacturing off-the-shelf, engineered, homogeneous cell therapy products, which are well-defined and uniform in composition, and can be mass produced at a significant scale in a cost-effective manner.

In view of the above, in yet some other embodiments, the iPSC-derived effector cells comprising an exogenous polynucleotide encoding at least a CAR, and optionally exogenous polynucleotides encoding one or both of hnCD16 and a cytokine and/or its receptor (IL) variant, one or more of the attributes comprising lig⁻, inR⁺, cs-CD3⁺, En⁺, and Ab⁺ (see Table 1), may additionally comprise deletion or reduced expression of at least one of B2M, CIITA, TAP1, TAP2, Tapasin, NLRC5, PD1, LAG3, TIM3, RFXANK, RFX5, RFXAP, RAG1, and any gene in the chromosome 6p21 region; or introduced or increased expression of at least one of HLA-E, HLA-G, 41BBL, CD4, CD8, CD16, CD47, CD113, CD131, CD137, CD80, PDL1, $A_{2A}R$, TCR, Fc receptor, and surface triggering receptor for coupling with bi-, multi-specific or universal engagers.

TABLE 1

Additional Attributes and Cell Genotype:

| CAR(CD16/IL) | lig−/− (ligand) | inR+ (ligand inactivation receptor) | cs-CD3+ (cell-surface CD3) | En+ (engager) | Ab+ (antibody/Check point inhibitor) | Genotype in addition to CAR(CD16/IL) |
|---|---|---|---|---|---|---|
| ✓ | ✓ | | | | | 1. lig−/− |
| ✓ | | ✓ | | | | 2. inR+ |
| ✓ | | | ✓ | | | 3. cs-CD3+ |
| ✓ | | | | ✓ | | 4. En+ |
| ✓ | | | | | ✓ | 5. Ab+ |
| ✓ | ✓ | ✓ | | | | 6. lig−/− inR+ |
| ✓ | ✓ | | ✓ | | | 7. lig−/− cs-CD3+ |
| ✓ | ✓ | | | ✓ | | 8. lig−/− En+ |
| ✓ | ✓ | | | | ✓ | 9. lig−/− Ab+ |
| ✓ | | ✓ | ✓ | | | 10. inR+ cs-CD3+ |
| ✓ | | ✓ | | ✓ | | 11. inR+ En+ |
| ✓ | | ✓ | | | ✓ | 12. inR+ Ab+ |
| ✓ | | | ✓ | ✓ | | 13. cs-CD3+ En+ |
| ✓ | | | ✓ | | ✓ | 14. cs-CD3+ Ab+ |
| ✓ | | | | ✓ | ✓ | 15. En+Ab+ |
| ✓ | ✓ | ✓ | ✓ | | | 16. lig−/− inR+ cs-CD3+ |
| ✓ | ✓ | ✓ | | ✓ | | 17. lig−/− inR+ En+ |
| ✓ | ✓ | ✓ | | | ✓ | 18. lig−/− inR+ Ab+ |
| ✓ | ✓ | | ✓ | ✓ | | 19. lig−/− cs-CD3+ En+ |
| ✓ | ✓ | | ✓ | | ✓ | 20. lig−/− cs-CD3+ Ab+ |
| ✓ | ✓ | | | ✓ | ✓ | 21. lig−/− En+ Ab+ |
| ✓ | | ✓ | ✓ | ✓ | | 22. inR+ cs-CD3+ En+ |
| ✓ | | ✓ | ✓ | | ✓ | 23. inR+ cs-CD3+ Ab+ |
| ✓ | | | ✓ | ✓ | ✓ | 24. cs-CD3+ En+ Ab+ |
| ✓ | ✓ | ✓ | ✓ | ✓ | | 25. lig−/− inR+ cs-CD3+ En+ |
| ✓ | ✓ | ✓ | ✓ | | ✓ | 26. lig−/− inR+ cs-CD3+ Ab+ |
| ✓ | ✓ | | ✓ | ✓ | ✓ | 27. lig−/− cs-CD3+ En+ Ab+ |
| ✓ | | ✓ | ✓ | ✓ | ✓ | 28. inR+ cs-CD3+ En+ Ab+ |
| ✓ | ✓ | ✓ | ✓ | ✓ | ✓ | 29. lig−/− inR+ cs-CD3+ En+ Ab+ |

As such, one aspect of the present application provides a composition comprising two or more synthetic effector cell types that have been differentiated from genomically engineered iPSCs. Thus, in various embodiments, the composition comprises a first population of synthetic effector cells that have been differentiated from genomically engineered iPSCs, and a second population of synthetic effector cells that have been differentiated from genomically engineered iPSCs. In one embodiment of the composition, the first type of synthetic effector cell or population thereof (i.e., first population) is a functionally enhanced iPSC-derived T cell, and the second type of synthetic effector cell or population thereof (i.e., second population) is a functionally enhanced iPSC-derived NK cell. In some embodiments, the functionally enhanced iPSC-derived T cell comprises at least a (first) CAR. In some embodiments, the functionally enhanced iPSC-derived NK cell comprises at least a (second) CAR, and one or both of a CD16 variant and a partial or full length of a cell surface expressed exogenous cytokine and/or a receptor thereof. In various embodiments, the CD16 variant is a high affinity non-cleavable CD16 (hnCD16).

As provided, the embodiments of said high affinity non-cleavable CD16 (hnCD16) or a variant thereof comprise at least one of the following: (a) F176V and S197P in ectodomain domain of CD16; (b) a full or partial ectodomain originated from CD64; (c) a non-native (or non-CD16) transmembrane domain; (d) a non-native (or non-CD16) intracellular domain; (e) a non-native (or non-CD16) signaling domain; (f) a non-native stimulatory domain; and (g) transmembrane, signaling, and stimulatory domains that are not originated from CD16, and are originated from the same or different polypeptides. In some embodiments, the non-native transmembrane domain is derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide, in some embodiments, the non-native stimulatory domain is derived from CD27, CD28, 4-1BB, OX40, ICOS, PD-1, LAG-3, 2B4, BTLA, DAP10, DAP12, CTLA-4, or NKG2D polypeptide. In some other embodiments, the non-native signaling domain is derived from CD3ζ, 2B4, DAP10, DAP12, DNAM1, CD137 (4-1BB), IL21, IL7, IL12, IL15, NKp30 NKp44, NKp46, NKG2C, or NKG2D polypeptide. In yet some other embodiments, the non-native transmembrane domain is derived from NKG2D, the non-native stimulatory domain is derived from 2B4, and the non-native signaling domain is derived from CD3ζ.

As provided, the first CAR of the synthetic cells in the first population and the second CAR of the synthetic cells in the second population provide targeting specificity to the synthetic cells. In some embodiments, the first CAR and the second CAR have the same targeting specificity. In some embodiments, the first CAR and the second CAR are different in targeting specificity. In some embodiments, the first CAR and the second CAR are the same or are different in targeting specificity, and the first CAR and/or the second CAR may have any one of the following characteristics, such that the first and/or the second CAR is: (i) T cell specific; (ii) NK cell specific; (iii) a bi-specific antigen binding CAR; (iv) a switchable CAR; (v) a dimerized CAR; (vi) a split CAR; (vii) a multi-chain CAR; or (viii) an inducible CAR. In some other embodiments, the first and/or the second CAR is co-expressed with yet another CAR, which may have the same or different targeting specificity as either of the first or second CAR.

In some embodiments, the first and/or the second CAR is co-expressed with a partial or full length peptide of a cell surface expressed exogenous cytokine and/or a receptor thereof, optionally in separate constructs or in a bi-cistronic construct. In yet some other embodiments, the first and/or the second CAR is co-expressed with a checkpoint inhibitor, optionally in separate constructs or in a bi-cistronic construct. In some embodiments, the first and/or the second CAR is specific to CD19 or BCMA. In other embodiments, the first and/or the second CAR is specific to at least one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen.

In some embodiments of the CAR-expressing cells of the first or the second population, the cells also express a partial or full length peptide of an exogenous cell surface cytokine and/or a receptor thereof. In some embodiments, the exogenous cell surface cytokine and/or a receptor variant thereof comprises at least one of IL2, IL4, IL6, IL7, IL9, IL10, IL11, IL12, IL15, IL18, IL21, and/or respective receptor thereof. In some other embodiments, the cytokine and/or a receptor variant thereof comprises at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL15Rβ, and any one of (i)-(vii) can be co-expressed with a CAR in separate constructs or in a bi-cistronic construct. In some embodiments, the partial or full length peptide of a cell surface exogenous cytokine and/or a receptor thereof is transiently expressed in the cell.

In some embodiments, the genetically modified iPSC and the functionally enhanced derivative effective cells therefrom, which include, but are not limited to iPSC-derived T and NK cells, comprise: (i) HLA-I deficiency, or B2M null or low; (ii) HLA-II deficiency, or CIITA null or low; (iii) introduced expression of HLA-G or non-cleavable HLA-G; (iv) at least one of $lig^-$, $inR^+$, $cs$-$CD3^+$, $En^+$, and $Ab^+$; wherein "$lig^-$" is negative in an expressed alloantigen; "$inR^+$" is positive in an expressed inactivation-CAR corresponding to the negative alloantigen; "$cs$-$CD3^+$" is positive in cell surface expressed CD3; "$En^+$" is positive in at least one expressed engager, wherein the engager comprises a bi-specific T cell engager (BiTE), or a tri-specific killer cell engager (TriKE); and "$Ab^+$" is positive in at least one expressed antibody or checkpoint inhibitor; (v) one or more of deletion or reduced expression of TAP1, TAP2, Tapasin, NLRC5, PD1, LAG3, TIM3, RFXANK, RFX5, RFXAP, RAG1, and any gene in the chromosome 6p21 region; and (vi) introduced or increased expression of at least one of HLA-E, HLA-G, 4-1BBL, CD4, CD8, CD16, CD47, CD113, CD131, CD137, CD80, PDL1, $A_{2A}R$, TCR, Fc receptor, and surface triggering receptor for coupling with bi-, multi-specific or universal engagers.

In some embodiments, said alloantigen to be knocked-out or knocked down in the iPSC-derived effector cells, including the derivative NK or T cells, comprises CD40L, OX40, or 4-1BB, which are up-regulated in activated recipient T, NK or B cells. In some embodiments, said inactivation-CAR in the iPSC-derived effector cells comprises CD40L-CAR, OX40-CAR, or 4-1BB-CAR, corresponding to the knocked-out alloantigen molecule in the iPSC-derived effector cells.

In some embodiments, the BiTE or TriKE expressed in the iPSC-derived effector cells recognize at least one immune cell surface molecule comprising CD3, CD28, CD5, CD16, NKG2D, CD64, CD32, CD89, NKG2C, or a chimeric Fc receptor thereof, and at least one tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1. In some embodiments, the BiTE expressed in the iPSC-derived effector cells comprises CD3-CD19, CD16-CD30, CD64-CD30, CD16-BCMA, CD64-BCMA, or CD3-CD33. In some embodiments, the TriKE expressed in the iPSC-derived effector cells comprises CD16-IL15-EPCAM, CD64-IL15-EPCAM, CD16-IL15-CD33, CD64-IL15-CD33, or NKG2C-IL15-CD33.

In some embodiments of the iPSC-derived effector cells, the cells express an antibody, wherein the antibody includes, but is not limited to an anti-CD20, anti-HER2, anti-CD52, anti-EGFR, anti-CD123, anti-GD2, anti-PDL1, antibody, or an anti-CD38 antibody. In some embodiments of the iPSC-derived effector cells, the cells express a checkpoint inhibitor, which includes, but is not limited to, an antagonist to a checkpoint molecule comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR. In some embodiments, the expressed checkpoint inhibitor in the iPSC-derived effector cells is one of atezolizumab, avelumab, durvalumab, ipilimumab, IPH4102, IPH43, IPH33, lirimumab, monalizumab, nivolumab, pembrolizumab, or a derivative or functional equivalent thereof. In yet another embodiment, the checkpoint inhibitor expressed in the iPSC-derived effector cells is one of atezolizumab, nivolutnab, and pembrolizumab.

As provided herein, the synthetic cells including, but not limited to iPSC-derived T cells or the iPSC-derived NK cells, of the first and the second cell populations of the composition each comprise one or more exogenous polynucleotides that contribute to the unique features of the synthetic cells. In some embodiments, the iPSC-derived T cells and/or the iPSC-derived NK cells comprise one or more exogenous polynucleotides integrated in one desired integration site. In some other embodiments, the iPSC-derived T cells and/or the iPSC-derived NK cells comprise more than two exogenous polynucleotides integrated in different desired integration sites. In some embodiments, the desired integration site(s) comprises at least one of AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD25, CD38, CD40L, CD44, CD54, CD56, CD58, CD69, CD71, OX40, 4-1BB, CIS, CBL-B, SOCS2, PD1, CTLA4, LAG3, TIM3, and TIGIT. In some other embodiments, the desired integration site(s) comprises TCR α or β constant region (TRAC or TRBC), CD25, CD38, CD40L, CD44, CD54, CD58, CD69, CD71, OX40 or 4-1BB. In yet some other embodiments, TCRα or TCRβ, CD25, CD38, CD40L, CD44, CD54, CD58, CD69, CD71, OX40 or 4-1BB is knocked-out as a result of integrating said one or more exogenous polynucleotides at the respective integration site(s).

In the embodiments of the composition comprising two or more synthetic cell populations, the synthetic cells of each population are derived from genomically engineered iPSC. In various embodiments, the first population is a population of iPSC-derived T cells and the second population is a population of iPSC-derived NK cells, or vice versa (i.e., the first population is a population of iPSC-derived NK cells and the second population is a population of iPSC-derived T cells). In some embodiments, the first population of iPSC-derived T cells and the second population of iPSC-derived NK cells each have at least one of the following characteristics: (i) improved persistency and/or survival, (ii) increased resistance to native immune cells, (iii) increased cytotoxicity, (iv) improved tumor penetration, (v) enhanced or acquired ADCC. (vi) enhanced ability in migrating, and/or activating or recruiting bystander immune cells to tumor sites; (vii) enhanced ability to reduce tumor immunosuppression, and (viii) improved ability in rescuing tumor antigen escape, in comparison to their native counterpart cells obtained from peripheral blood, umbilical cord blood, or any other donor tissues. In addition, the iPSC-derived T cells and/or the iPSC-derived NK cells comprise longer telomeres in comparison to their respective native counterpart cells obtained from peripheral blood, umbilical cord blood, or any other donor tissues.

In some embodiments of the composition comprising two or more synthetic cell populations, the synthetic cells of the first and/or the second population that are derived from genomically engineered iPSC are modulated. In some embodiments, the modulated synthetic cells of the first population are iPSC-derived. T cells, and the first population comprises an increased number or ratio of naïve T cells, stem cell memory T cells, and/or central memory T cells in comparison to the first cell population without modulation. In some embodiments, the modulated synthetic cells of the second population are iPSC-derived NK cells, and the second cell population comprises an increased number or ratio of type I NKT cells, and/or adaptive NK cells in comparison to the cell population without modulation.

In some embodiments of the composition comprising a first synthetic cell population comprising derivative T cells differentiated from engineered iPSC, and a second synthetic cell population comprising derivative NK cells differentiated from engineered iPSC, the derivative T cells and the derivative NK cells are in a ratio ranging from 100:1 to 1:100. In some embodiments, the derivative T cells and the derivative NK cells are in a ratio ranging from 50:1 to 1:50. In some embodiments, the derivative T cells and the derivative NK cells are in a ratio ranging from 20:1 to 1:20. In some other embodiments, the derivative T cells and the derivative NK cells are in a ratio ranging from 10:1 to 1:10. In yet some other embodiments, the derivative T cells and the derivative NK cells are in a ratio of 1:1.

In some embodiments of the composition comprising a first synthetic cell population comprising derivative T cells differentiated from engineered iPSC, and a second synthetic cell population comprising derivative NK cells differentiated from engineered iPSC, the composition further comprises one or more additional cell populations. In one embodiment, the additional cell population comprises regulatory cells. In another embodiment, the additional cell population comprises myeloid derived suppressor cells (MDSCs). In yet another embodiment, the MDSCs of the additional cell population are derived from iPSC.

Yet another aspect of this application provides a composition as described above that further comprises one or more therapeutic agents in addition to at least two synthetic cell populations comprising iPSC-derived T cells and iPSC-derived NK cells, respectively. Suitable therapeutic agents, including, but not limited to, antibodies and checkpoint inhibitors that can be used with the synthetic cells are further detailed below.

II. Methods for Targeted Genome Editing at Selected Locus in iPSCs

Genome editing, or genomic editing, or genetic editing, as used interchangeably herein, is a type of genetic engineering in which DNA is inserted, deleted, and/or replaced in the genome of a targeted cell. Targeted genome editing (interchangeable with "targeted genomic editing" or "targeted genetic editing") enables insertion, deletion, and/or substitution at pre-selected sites in the genome. When an endogenous sequence is deleted at the insertion site during targeted editing, an endogenous gene comprising the affected sequence may be knocked-out or knocked-down due to the sequence deletion. Therefore, targeted editing may also be used to disrupt endogenous gene expression with precision. Similarly used herein is the term "targeted integration," referring to a process involving insertion of one or more exogenous sequences, with or without deletion of an endogenous sequence at the insertion site. In comparison, randomly integrated genes are subject to position effects and silencing, making their expression unreliable and unpredictable. For example, centromeres and sub-telomeric regions are particularly prone to transgene silencing. Reciprocally, newly integrated genes may affect the surrounding endogenous genes and chromatin, potentially altering cell behavior or favoring cellular transformation. Therefore, inserting exogenous DNA in a pre-selected locus such as a safe harbor locus, or genomic safe harbor (GSH) is important for safety, efficiency, copy number control, and for reliable gene response control.

Targeted editing can be achieved either through a nuclease-independent approach, or through a nuclease-dependent approach. In the nuclease-independent targeted editing approach, homologous recombination is guided by homologous sequences flanking an exogenous polynucleotide to be inserted, through the enzymatic machinery of the host cell.

Alternatively, targeted editing could be achieved with higher frequency through specific introduction of double strand breaks (DSBs) by specific rare-cutting endonucleases. Such nuclease-dependent targeted editing utilizes DNA repair mechanisms including non-homologous end joining (NHEJ), which occurs in response to DSBs. Without a donor vector containing exogenous genetic material, the NHEJ often leads to random insertions or deletions (in/dels) of a small number of endogenous nucleotides. In comparison, when a donor vector containing exogenous genetic material flanked by a pair of homology arms is present, the exogenous genetic material can be introduced into the genome during homology directed repair (HDR) by homologous recombination, resulting in a "targeted integration." In some situations, the targeted integration site is intended to be within a coding region of a selected gene, and thus the targeted integration could disrupt the gene expression, resulting in simultaneous knock-in and knock-out (KI/KO) in one single editing step.

Inserting one or more transgenes at a selected position in a gene locus of interest (GOI) to knock-out the gene at the same time can be achieved. Gene loci suitable for simultaneous knock-in and knock-out (KI/KO) include, but are not limited to, B2M, TAP1, TAP2, tapasin, NLRC5, CIITA, RFXANK, RFX5, RFXAP, TCR α or β constant region (TRAC or TRBC), NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, and TIGIT. With respective site-specific targeting homology arms for position-selective insertion, it allows the transgene(s) to express either under an endogenous promoter at the site or under an exogenous promoter comprised in the construct. When two or more transgenes are to be inserted at a selected location (e.g., in a CD38 locus), a linker sequence, for example, a 2A linker or IRES, is placed between any two transgenes. The 2A linker encodes a self-cleaving peptide derived from FMDV, ERAV, PTV-I, or TaV (referred to as "F2A", "E2A", "P2A", and "T2A", respectively), allowing for separate proteins to be produced from a single translation. In some embodiments, insulators are included in the construct to reduce the risk of transgene and/or exogenous promoter silencing. In various embodiments, the exogenous promoter may be CAG, or other constitutive, inducible, temporal-, tissue-, or cell type-specific promoters including, but not limited to CMV, EF1α, PGK, and UBC.

Available endonucleases capable of introducing specific and targeted DSBs include, but are not limited to, zinc-finger nucleases (ZFN), transcription activator-like effector nucleases (TALEN), RNA-guided CRISPR (Clustered Regular Interspaced Short Palindromic Repeats) systems. Additionally, the DICE (dual integrase cassette exchange) system utilizing phiC31 and Bxb1 integrases is also a promising tool for targeted integration.

ZFNs are targeted nucleases comprising a nuclease fused to a zinc finger DNA binding domain. By a "zinc finger DNA binding domain" or "ZFBD", it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but are not limited to, $C_2H_2$ zinc fingers, $C_3H$ zinc fingers, and $C_4$ zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO98/53058; WO98/53059; WO98/53060; WO02/016536 and WO03/016496, the complete disclosures of which are incorporated herein by reference. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the FokI nuclease with a zinc finger DNA binding domain.

A TALEN is a targeted nuclease comprising a nuclease fused to a TAL effector DNA binding domain. By "transcription activator-like effector DNA binding domain", "TAL effector DNA binding domain", or "TALE DNA binding domain", it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a targeted Spo11 nuclease, a polypeptide comprising a Spo11 polypeptide having nuclease activity fused to a DNA binding domain, e.g. a zinc finger DNA binding domain, a TAL effector DNA binding domain, etc. that has specificity for a DNA sequence of interest.

Additional examples of targeted nucleases suitable for the present invention include, but not limited to Bxb1, phiC31, R4, PhiBT1, and Wβ/SPBc/TP901-1, whether used individually or in combination.

Other non-limiting examples of targeted nucleases include naturally occurring and recombinant nucleases; CRISPR related nucleases from families including cas, cpf, cse, csy, csn, csd, cst, csh, csa, csm, and cmr; restriction endonucleases; meganucleases; homing endonucleases, and the like.

Using Cas9 as an example, CRISPR/Cas9 typically requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences. These two components can then be delivered to mammalian cells via transfection or transduction. Use of the CRISPR/Cpf system, typically requires (1) a Cpf endonuclease (e.g., Cpf1, MAD7 and many more known in the art) and (2) the gNA, which often does not need tracrRNA, to guide Cpf endonuclease to target selected sequences.

DICE mediated insertion uses a pair of recombinases, for example, phiC31 and Bxb1, to provide unidirectional integration of an exogenous DNA that is tightly restricted to each enzymes' own small attB and attP recognition sites. Because these target att sites are not naturally present in mammalian genomes, they must be first introduced into the genome, at the desired integration site. See, for example, U.S. Pub. No. 2015/0140665, the disclosure of which is incorporated herein by reference.

One aspect of the present invention provides a construct comprising one or more exogenous polynucleotides for targeted genome integration. Thus, the synthetic cells of the first and second populations of the composition of the invention may be produced using one or more constructs comprising one or more exogenous polynucleotides for targeted genome integration. In one embodiment, the construct further comprises a pair of homologous arms specific to a desired integration site, and the method of targeted integration comprises introducing the construct to cells to enable site specific homologous recombination by the cell host enzymatic machinery. In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration.

Promising sites for targeted integration include, but are not limited to, safe harbor loci, or genomic safe harbor (GSH), which are intragenic or extragenic regions of the human genome that, theoretically, are able to accommodate predictable expression of newly integrated DNA without adverse effects on the host cell or organism. A useful safe harbor must permit sufficient transgene expression to yield desired levels of the vector-encoded protein or non-coding RNA. A safe harbor also must not predispose cells to malignant transformation nor alter cellular functions. For an integration site to be a potential safe harbor locus, it ideally needs to meet criteria including, but not limited to: absence of disruption of regulatory elements or genes, as judged by sequence annotation; is an intergenic region in a gene dense area, or a location at the convergence between two genes transcribed in opposite directions; keep distance to minimize the possibility of long-range interactions between vector-encoded transcriptional activators and the promoters of adjacent genes, particularly cancer-related and microRNA genes; and has apparently ubiquitous transcriptional activity, as reflected by broad spatial and temporal expressed sequence tag (EST) expression patterns, indicating ubiquitous transcriptional activity. This latter feature is especially important in stem cells, where during differentiation, chromatin remodeling typically leads to silencing of some loci and potential activation of others. Within the region suitable for exogenous insertion, a precise locus chosen for insertion should be devoid of repetitive elements and conserved sequences and to which primers for amplification of homology arms could easily be designed.

Suitable sites for human genome editing, or specifically, targeted integration, include, but are not limited to the adeno-associated virus site 1 (AAVS1), the chemokine (CC motif) receptor 5 (CCR5) gene locus and the human orthologue of the mouse ROSA26 locus. Additionally, the human orthologue of the mouse H11 locus may also be a suitable site for insertion using the composition and method of targeted integration disclosed herein. Further, collagen and HTRP gene loci may also be used as safe harbor for targeted integration. However, validation of each selected site has been shown to be necessary especially in stem cells for specific integration events, and optimization of insertion strategy including promoter election, exogenous gene sequence and arrangement, and construct design is often needed.

For targeted in/dels, the editing site is often comprised in an endogenous gene whose expression and/or function is intended to be disrupted. In some embodiments, the endogenous gene comprising a targeted in/del is associated with immune response regulation and modulation. In some other embodiments, the endogenous gene comprising a targeted in/del is associated with targeting modality, receptors, signaling molecules, transcription factors, drug target candidates, immune response regulation and modulation, or proteins suppressing engraftment, trafficking, homing, viability, self-renewal, persistence, and/or survival of stem cells and/or progenitor cells, and the derived cells therefrom.

As such, another aspect of the present invention provides a method of targeted integration in a selected locus including genome safe harbor or a preselected locus known or proven to be safe and well-regulated for continuous or temporal gene expression such as the B2M, TAP1, TAP2, tapasin, TRAC, or CD38 locus as provided herein; and the synthetic cells of the first and second populations of the composition of the invention may be produced using such method. In one embodiment, the genome safe harbor for the method of targeted integration comprises one or more desired integration site comprising AAVS1, CCR5, ROSA26, collagen, HTRP, H11, beta-2 microglobulin, CD38, GAPDH, TCR or RUNX1, or other loci meeting the criteria of a genome safe harbor. In some embodiments, the targeted integration is in one or more gene loci where the knock-down or knock-out of the gene as a result of the integration is desired, wherein such gene loci include, but are not limited to, B2M, TAP1, TAP2, tapasin, NLRC5, CIITA, RFXANK, RFX5, RFXAP, TCR α or β constant region (TRAC or TRBC), NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, and TIGIT.

In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAG3, TIM3, or TIGIT.

Further, as provided herein, the above method for targeted integration in a safe harbor is used to insert any polynucleotide of interest, for example, polynucleotides encoding safety switch proteins, targeting modality, receptors, signaling molecules, transcription factors, pharmaceutically active proteins and peptides, drug target candidates, and proteins promoting engraftment, trafficking, homing, viability, self-renewal, persistence, and/or survival of stem cells and/or progenitor cells. In some other embodiments, the construct comprising one or more exogenous polynucleotides further comprises one or more marker genes. In one embodiment, the exogenous polynucleotide in a construct of the invention is a suicide gene encoding safety switch protein. Suitable suicide gene systems for induced cell death include, but not limited to Caspase 9 (or caspase 3 or 7) and AP1903; thymidine kinase (TK) and ganciclovir (GCV); cytosine deaminase (CD) and 5-fluorocytosine (5-FC). Additionally, some suicide gene systems are cell type specific, for example, the genetic modification of T lymphocytes with the B-cell molecule CD20 allows their elimination upon administration of mAb Rituximab. Further, modified EGFR containing epitope recognized by cetuximab can be used to deplete genetically engineered cells when the cells are exposed to cetuximab. As such, one aspect of the invention provides a method of targeted integration of one or more suicide genes encoding safety switch proteins selected from caspase 9 (caspase 3 or 7), thymidine kinase, cytosine deaminase, modified EGFR, and B-cell CD20.

In some embodiments, one or more exogenous polynucleotides integrated by the method described herein are driven by operatively-linked exogenous promoters comprised in the construct for targeted integration. The promoters may be inducible, or constructive, and may be temporal-, tissue- or cell type-specific. Suitable constructive promoters for methods of the invention include, but not limited to, cytomegalovirus (CMV), elongation factor 1α (EF1α), phosphoglycerate kinase (PGK), hybrid CMV enhancer/chicken β-actin (CAG) and ubiquitin C (UBC) promoters. In one embodiment, the exogenous promoter is CAG.

The exogenous polynucleotides integrated by the method described herein may be driven by endogenous promoters in the host genome, at the integration site. In one embodiment, the method described herein is used for targeted integration of one or more exogenous polynucleotides at AAVS1 locus in the genome of a cell. In one embodiment, at least one integrated polynucleotide is driven by the endogenous AAVS1 promoter. In another embodiment, the method described herein is used for targeted integration at ROSA26 locus in the genome of a cell. In one embodiment, at least one integrated polynucleotide is driven by the endogenous ROSA26 promoter. In still another embodiment, the method of the invention is used for targeted integration at H11 locus in the genome of a cell. In one embodiment, at least one integrated polynucleotide is driven by the endogenous H11 promoter. In another embodiment, the method described herein is used for targeted integration at collagen locus in the genome of a cell. In one embodiment, at least one integrated polynucleotide is driven by the endogenous collagen promoter. In still another embodiment, the method of the invention is used for targeted integration at HTRP locus in the genome of a cell. In one embodiment, at least one integrated polynucleotide is driven by the endogenous HTRP promoter. Theoretically, only correct insertions at the desired location would enable gene expression of an exogenous gene driven by an endogenous promoter.

In some embodiments, the one or more exogenous polynucleotides comprised in the construct for the methods of targeted integration are driven by one promoter. In some embodiments, the construct comprises one or more linker sequences between two adjacent polynucleotides driven by the same promoter to provide greater physical separation between the moieties and maximize the accessibility to enzymatic machinery. The linker peptide of the linker sequences may consist of amino acids selected to make the physical separation between the moieties (exogenous polynucleotides, and/or the protein or peptide encoded therefrom) more flexible or more rigid depending on the relevant function. The linker sequence may be cleavable by a protease or cleavable chemically to yield separate moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the moiety with respect to another adjacent moiety for the moieties to function properly. The linker may also be a simple amino acid sequence of a sufficient length to prevent any steric hindrance between the moieties. In addition, the linker sequence may provide for post-translational modification including, but not limited to, e.g., phosphorylation sites, biotinylation sites, sulfation sites, γ-carboxylation sites, and the like. In some embodiments, the linker sequence is flexible so as not hold the biologically active peptide in a single undesired conformation. The linker may be predominantly comprised of amino acids with small side chains, such as glycine, alanine, and serine, to provide for flexibility. In some embodiments about 80 to 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a 2A linker sequence allows for two separate proteins to be produced from a single translation. Suitable linker sequences can be readily identified empirically. Additionally, suitable size and sequences of linker sequences also can be determined by conventional computer modeling techniques. In one embodiment, the linker sequence encodes a self-cleaving peptide. In one embodiment, the self-cleaving peptide is 2A. In some other embodiments, the linker sequence provides an Internal Ribosome Entry Sequence (IRES). In some embodiments, any two consecutive linker sequences are different.

The method of introducing into cells a construct comprising exogenous polynucleotides for targeted integration can be achieved using a method of gene transfer to cells known per se. In one embodiment, the construct comprises backbones of viral vectors such as adenovirus vector, adeno-associated virus vector, retrovirus vector, lentivirus vector, Sendai virus vector. In some embodiments, the plasmid vectors are used for delivering and/or expressing the exogenous polynucleotides to target cells (e.g., pA1-11, pXT1, pRc/CMV, pRc/RSV, pcDNAI/Neo) and the like. In some other embodiments, the episomal vector is used to deliver the exogenous polynucleotide to target cells. In some embodiments, recombinant adeno-associated viruses (rAAV) can be used for genetic engineering to introduce insertions, deletions or substitutions through homologous recombinations. Unlike lentiviruses, rAAVs do not integrate into the host genome. In addition, episomal rAAV vectors mediate homology-directed gene targeting at much higher rates compared to transfection of conventional targeting plasmids. In some embodiments, an AAV6 or AAV2 vector is used to introduce insertions, deletions or substitutions in a target site in the genome of iPSCs. In some embodiments, the genomically modified iPSCs and their derivative cells obtained using the methods and compositions described herein comprise at least one genotype listed in Table 1.

III. Method of Obtaining and Maintaining Genome-Engineered iPSCs

In various embodiments, the present invention provides a method of obtaining and maintaining genome-engineered iPSCs comprising one or more targeted edits at one or more desired sites, wherein the one or more targeted edits remain intact and functional in expanded genome-engineered iPSCs or the iPSC-derived non-pluripotent cells at the respective selected editing site. The targeted editing introduces into the genome iPSC, and derivative cells therefrom, insertions, deletions, and/or substitutions (i.e., targeted integration and/ or in/dels at selected sites). In comparison to direct engineering of patient-sourced, peripheral blood originated primary effector cells, the many benefits of obtaining genomically-engineered derivative cells through editing and differentiating iPSC as provided herein include, but are not limited to: unlimited source for engineered effector cells; no need for repeated manipulation of the effector cells, especially when multiple engineered modalities are involved; the obtained effector cells are rejuvenated for having elongated telomere and experiencing less exhaustion; the effector cell population is homogeneous in terms of editing site, copy number, and void of allelic variation, random mutations and expression variegation, largely due to the enabled clonal selection in engineered iPSCs as provided herein.

In particular embodiments, the genome-engineered iPSCs comprising one or more targeted edits at one or more selected sites are maintained, passaged and expanded as single cells for an extended period in the cell culture medium shown in Table 2 as Fate Maintenance Medium (FMM), wherein the iPSCs retain the targeted editing and functional modification at the selected site(s). The components of the medium may be present in the medium in amounts within an optimal range shown in Table 2. The iPSCs cultured in FMM have been shown to continue to maintain their undifferentiated, and ground or naïve, profile; genomic stability without the need for culture cleaning or selection; and readily to give rise to all three somatic lineages, in vitro differentiation via embryoid bodies or monolayer (without formation of embryoid bodies); and in vivo differentiation by teratoma formation. See, for example, International Pub. No. WO2015/134652, the disclosure of which is incorporated herein by reference.

TABLE 2

Exemplary media for iPSC reprogramming and maintenance

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum | Knockout Serum | Knockout Serum |
| | N2 | |
| | B27 | |
| Glutamine | Glutamine | Glutamine (1×) |
| Non-Essential Amino Acids | Non-Essential Amino Acids | Non-Essential Amino Acids |
| β-mercaptoethanol | β-mercaptoethanol | β-mercaptoethanol |
| bFGF (0.2-50 ng/mL) | bFGF (2-500 ng/mL) | bFGF (2-500 ng/mL) |
| | LIF (0.2-50 ng/mL) | LIF (0.2-50 ng/mL) |
| | Thiazovivin (0.1-25 μM) | Thiazovivin (0.1-25 μM) |
| | PD0325901 (0.005-2 μM) | PD0325901 (0.005-2 μM) |
| | CHIR99021 (0.02-5 μM) | CHIR99021 (0.02-5 μM) |
| | SB431542 (0.04-10 μM) | |
| In combination with MEF | Feeder-free, in combination with Matrigel ™ or Vitronectin | |

In some embodiments, the genome-engineered iPSCs comprising one or more targeted integration and/or in/dels are maintained, passaged and expanded in a medium comprising a MEK inhibitor, a GSK inhibitor, and a ROCK inhibitor, and free of, or essentially free of, TGFβ receptor/ ALK5 inhibitors, wherein the iPSCs retain the intact and functional targeted edits at the selected sites.

Another aspect of the invention provides a method of generating genome-engineered iPSCs through targeted editing of iPSCs; or through first generating genome-engineered non-pluripotent cells by targeted editing, and then reprogramming the selected/isolated genome-engineered non-pluripotent cells to obtain iPSCs comprising the same targeted editing as the non-pluripotent cells. A further aspect of the invention provides genome-engineering non-pluripotent cells which are concurrently undergoing reprogramming by introducing targeted integration and/or targeted in/dels to the cells, wherein the contacted non-pluripotent cells are under sufficient conditions for reprogramming, and wherein the conditions for reprogramming comprise contacting non-pluripotent cells with one or more reprogramming factors and small molecules. In various embodiments of the method for concurrent genome-engineering and reprogramming, the targeted integration and/or targeted in/dels may be introduced to the non-pluripotent cells prior to, or essentially concomitantly with, initiating reprogramming by contacting the non-pluripotent cells with one or more reprogramming factors and optionally one or more small molecules.

In some embodiments, to concurrently genome-engineer and reprogram non-pluripotent cells, the targeted integration and/or in/dels may also be introduced to the non-pluripotent cells after the multi-day process of reprogramming is initiated by contacting the non-pluripotent cells with one or more reprogramming factors and small molecules, and wherein the vectors carrying the constructs are introduced before the reprogramming cells present stable expression of one or more endogenous pluripotent genes including, but not limited to, SSEA4, Tra181 and CD30.

In some embodiments, the reprogramming is initiated by contacting the non-pluripotent cells with at least one reprogramming factor, and optionally a combination of a TGFβ receptor/ALK inhibitor, a MEK inhibitor, a GSK3 inhibitor and a ROCK inhibitor (FRM; Table 2). In some embodiments, the genome-engineered iPSCs produced through any methods above are further maintained and expanded using a mixture comprising a combination of a MEK inhibitor, a GSK3 inhibitor and a ROCK inhibitor (FMM; Table 2).

In some embodiments of the method of generating genome-engineered iPSCs, the method comprises: genomically engineering an iPSC by introducing one or more targeted integrations and/or in/dels into iPSCs to obtain genome-engineered iPSCs having at least one genotype listed in Table 1. Alternatively, the method of generating genome-engineered iPSCs comprises: (a) introducing one or more targeted edits into non-pluripotent cells to obtain genome-engineered non-pluripotent cells comprising targeted integrations and/or in/dels at selected sites, and (b) contacting the genome-engineered non-pluripotent cells with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted integrations and/or in/dels at selected sites. Alternatively, the method of generating genome-engineered iPSCs comprises: (a) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate the reprogramming of the non-pluripotent cells; (b) introducing one or more targeted integrations and/or in/dels into the reprogramming non-pluripotent cells for genome-engineering; and (c) obtaining genome-engineered iPSCs comprising targeted integrations and/or in/dels at selected sites. Any of the above methods may further comprise single cell sorting of the genome-engineered iPSCs to obtain a clonal iPSC. Through clonal expansion of the genome-engineered iPSCs, a master cell bank is generated to comprise single cell sorted and expanded clonal engineered iPSCs having at least one phenotype as provided herein. The master cell bank is subsequently cryopreserved, providing a platform for additional iPSC engineering and a renewable source for manufacturing off-the-shelf, engineered, homogeneous cell therapy products, which are well-defined and uniform in composition, and can be mass produced at significant scale in a cost-effective manner.

The reprogramming factors are selected from the group consisting of OCT4, SOX2, NANOG, KLF4, LIN28, C-MYC, ECAT1, UTF1, ESRRB, SV40LT, HESRG, CDH1, TDGF1, DPPA4, DNMT3B, ZIC3, L1 TD1, and any combinations thereof, as disclosed in International Pub. Nos. WO2015/134652 and WO2017/066634, the disclosures of which are incorporated herein by reference. The one or more reprogramming factors may be in the form of a polypeptide. The reprogramming factors may also be in the form of polynucleotides encoding the reprogramming factors, and thus may be introduced to the non-pluripotent cells by vectors such as, a retrovirus, a Sendai virus, an adenovirus, an episome, a plasmid, and a mini-circle. In particular embodiments, the one or more polynucleotides encoding at least one reprogramming factor are introduced by a lentiviral vector. In some embodiments, the one or more polynucleotides introduced by an episomal vector. In various other embodiments, the one or more polynucleotides are introduced by a Sendai viral vector. In some embodiments, the one or more polynucleotides introduced by a combination of plasmids. See, for example, International Pub. No. WO2019/075057A1, the disclosure of which is incorporated herein by reference.

In some embodiments, the non-pluripotent cells are transfected with multiple constructs comprising different exogenous polynucleotides and/or different promoters by multiple vectors for targeted integration at the same or different selected sites. These exogenous polynucleotides may comprise a suicide gene, or a gene encoding targeting modality, receptors, signaling molecules, transcription factors, pharmaceutically active proteins and peptides, drug target candidates, or a gene encoding a protein promoting engraftment, trafficking, homing, viability, self-renewal, persistence, and/or survival of the iPSCs or derivative cells therefrom. In some embodiments, the exogenous polynucleotides encode RNA, including but not limited to siRNA, shRNA, miRNA and antisense nucleic acids. These exogenous polynucleotides may be driven by one or more promoters selected form the group consisting of constitutive promoters, inducible promoters, temporal-specific promoters, and tissue or cell type specific promoters. Accordingly, the polynucleotides are expressible when under conditions that activate the promoter, for example, in the presence of an inducing agent or in a particular differentiated cell type. In some embodiments, the polynucleotides are expressed in iPSCs and/or in cells differentiated from the iPSCs. In one embodiment, one or more suicide genes are driven by a constitutive promoter, for example Capase-9 driven by CAG. These constructs comprising different exogenous polynucleotides and/or different promoters can be transfected to non-pluripotent cells either simultaneously or consecutively. The non-pluripotent cells subjected to targeted integration of multiple constructs can simultaneously contact the one or more reprogramming factors to initiate the reprogramming concurrently with the genomic engineering, thereby obtaining genome-engineered iPSCs comprising multiple targeted integrations in the same pool of cells. As such, this robust method enables a concurrent reprogramming and engineering strategy to derive a clonal genomically-engineered iPSC with multiple modalities integrated to one or more selected target sites. In some embodiments, the genomically modified iPSCs and their derivative cells obtained using the methods and composition provided herein comprise at least one genotype listed in Table 1.

IV. A Method of Obtaining Synthetic Effector Cells by Differentiating Genome-Engineered iPSC A further aspect of the present invention provides a method of in vivo differentiation of genome-engineered iPSCs by teratoma formation, wherein the differentiated cells derived in vivo from the genome-engineered iPSCs retain the intact and functional targeted edits including targeted integration(s) and/or in/dels at the desired site(s). In some embodiments, the differentiated cells derived in vivo from the genome-engineered iPSCs via teratoma formation comprise one or more inducible suicide genes integrated at one or more desired sites comprising AAVS1, CCR5, ROSA26, collagen, HTRP H11, beta-2 microglobulin, CD38, GAPDH, TCR or RUNX1, or other loci meeting the criteria of a genome safe harbor. In some other embodiments, the differentiated cells derived in vivo from the genome-engineered iPSCs via teratoma formation comprise polynucleotides encoding targeting modalities, or encoding proteins promoting trafficking, homing, viability, self-renewal, persistence, and/or survival of stem cells and/or progenitor cells. In some embodiments, the differentiated cells derived in vivo from the genome-engineered iPSCs via teratoma formation comprising one or more inducible suicide genes further comprise one or more in/dels in endogenous genes associated with immune response regulation and mediation. In some embodiments, the in/del is comprised in one or more endogenous checkpoint genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAGS, TIM3, and TIGIT. In one embodiment, the genome-engineered iPSCs comprising one or more exogenous polynucleotides at selected site(s) further comprise a targeted edit in a B2M (beta-2-microglobulin) encoding gene.

In particular embodiments, the genome-engineered iPSCs comprising one or more genetic modifications as provided herein are used to derive hematopoietic cell lineages or any other specific cell types in vitro, wherein the derived non-pluripotent cells retain the functional genetic modifications including targeted editing at the selected site(s). In some embodiments, the genome-engineered iPSCs used to derive hematopoietic cell lineages or any other specific cell types in vitro are master cell bank cells that are cryopreserved and thawed right before their usage. In one embodiment, the genome-engineered iPSC-derived cells include, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages, wherein the cells derived from the genome-engineered iPSCs retain the functional genetic modifications including targeted editing at the desired site(s).

Applicable differentiation methods and compositions for obtaining iPSC-derived hematopoietic cell lineages include those depicted in, for example, International Pub. No. WO2017/078807, the disclosure of which is incorporated herein by reference. As provided, the methods and compositions for generating hematopoietic cell lineages are through definitive hemogenic endothelium (HE) derived from pluripotent stem cells, including iPSCs under serum-free, feeder-free, and/or stromal-free conditions and in a scalable and monolayer culturing platform without the need of EB formation. Cells that may be differentiated according to the provided methods range from pluripotent stem cells, to progenitor cells that are committed to particular terminally differentiated cells and transdifferentiated cells, and to cells of various lineages directly transitioned to hematopoietic fate without going through a pluripotent intermediate. Similarly, the cells that are produced by differentiating stem cells range from multipotent stem or progenitor cells, to terminally differentiated cells, and to all intervening hematopoietic cell lineages.

The methods for differentiating and expanding cells of the hematopoietic lineage from pluripotent stem cells in monolayer culturing comprise contacting the pluripotent stem cells with a BMP pathway activator, and optionally, bFGF. As provided, the pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion and homogeneous differentiation of the cells in a population, and is laborious and of low efficiency.

The provided monolayer differentiation platform facilitates differentiation towards definitive hemogenic endothelium resulting in the derivation of hematopoietic stem cells and differentiated progeny such as T, B, NKT and NK cells. The monolayer differentiation strategy combines enhanced differentiation efficiency with large-scale expansion, and enables the delivery of a therapeutically relevant number of pluripotent stem cell-derived hematopoietic cells for various therapeutic applications. Further, monolayer culturing using the methods provided herein leads to functional hematopoietic lineage cells that enable a full range of in vitro differentiation, ex vivo modulation, and in vivo long term hematopoietic self-renewal, reconstitution and engraftment. As provided, the iPSC-derived hematopoietic lineage cells include, but are not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

Thus, in various embodiments, the method for directing differentiation of pluripotent stem cells into cells of a definitive hematopoietic lineage, comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential.

In some embodiments, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs, or naïve iPSCs, or iPSCs comprising one or more genetic imprints; and the one or more genetic imprints comprised in the iPSCs are retained in the hematopoietic cells differentiated therefrom. In some embodiments of the method for directing differentiation of pluripotent stem cells into cells of a hematopoietic lineage, the differentiation of the pluripotent stem cells into cells of hematopoietic lineage is void of generation of embryoid bodies, and is in a monolayer culturing form.

In some embodiments of the above method, the obtained pluripotent stem cell-derived definitive hemogenic endothelium cells are $CD34^+$. In some embodiments, the obtained definitive hemogenic endothelium cells are $CD34^+CD43^-$. In some embodiments, the definitive hemogenic endothelium cells are $CD34^+CD43^-CXCR4^-CD73^-$. In some embodiments, the definitive hemogenic endothelium cells are $CD34^+CXCR4^-CD73^-$. In some embodiments, the definitive hemogenic endothelium cells are $CD34^+CD43^-CD93^-$. In some embodiments, the definitive hemogenic endothelium cells are $CD34^+CD93^-$.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are $CD34^+CD45^+CD7^+$. In some embodiments of the method, the pluripotent stem cell-derived T cell progenitors are $CD45^+CD7^+$.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are $CD3^-CD45^+CD56^+CD7^+$. In some embodiments, the pluripotent stem cell-derived NK cells are $CD3^-CD45^+CD56^+$, and optionally further defined by being $NKp46^+$, $CD57^+$ and $CD16^+$.

Therefore, using the above differentiation methods, one may obtain one or more populations of iPSC-derived hematopoietic cells: (i) $CD34^+$ HE cells (iCD34), using one or more culture medium selected from iMPP-A, iTC-A2, iTC-B2, iNK-A2, and iNK-B2; (ii) definitive hemogenic endothelium (iHE), using one or more culture medium selected from iMPP-A, iTC-A2, iTC-B2, iNK-A2, and iNK-B2; (iii) definitive HSCs, using one or more culture medium selected from iMPP-A, iTC-A2, iTC-B2, iNK-A2, and iNK-B2; (iv) multipotent progenitor cells (iMPP), using iMPP-A; (v) T cell progenitors (ipro-T), using one or more culture medium selected from iTC-A2, and iTC-B2; (vi) T cells (iTC), using iTC-B2; (vii) NK cell progenitors (ipro-NK), using one or more culture medium selected from iNK-A2, and iNK-B2; and/or (viii) NK cells (iNK), and iNK-B2. In some embodiments, the medium:

a. iCD34-C comprises a ROCK inhibitor, one or more growth factors and cytokines selected from the group consisting of bFGF, VEGF, SCF, IL6, IL11, IGF, and EPO, and optionally, a Wnt pathway activator; and is free of TGFβ receptor/ALK inhibitor;

b. iMPP-A comprises a BMP activator, a ROCK inhibitor, and one or more growth factors and cytokines selected from the group consisting of TPO, IL3, GMCSF, EPO, bFGF, VEGF, SCF, IL6, Flt3L and IL11;

c. iTC-A2 comprises a ROCK inhibitor; one or more growth factors and cytokines selected from the group consisting of SCF, Flt3L, TPO, and IL7; and optionally, a BMP activator;

d. iTC-B2 comprises one or more growth factors and cytokines selected from the group consisting of SCF, Flt3L, and IL7;

e. iNK-A2 comprises a ROCK inhibitor, and one or more growth factors and cytokines selected from the group consisting of SCF, Flt3L, TPO, IL3, IL7, and IL15; and optionally, a BMP activator, and f. iNK-B2 comprises one or more growth factors and cytokines selected from the group consisting of SCF, Flt3L, IL7 and IL15.

In some embodiments, the genome-engineered iPSC-derived cells obtained from the above methods comprise one or more inducible suicide gene integrated at one or more desired integration sites comprising AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD44, CD54, CD56, CD58, CD69, CD71, OX40, 4-1BB, CIS, CBL-B, SOCS2, PD1, CTLA4, LAGS, TIM3, and TIGIT, or other loci meeting the criteria of a genome safe harbor. In some other embodiments, the genome-engineered iPSC-derived cells comprise polynucleotides encoding safety switch proteins, targeting modality, receptors, signaling molecules, transcription factors, pharmaceutically active proteins and peptides, drug target candidates, or proteins promoting trafficking, homing, viability, self-renewal, persistence, and/or survival of stem cells and/or progenitor cells. In some embodiments, the genome-engineered iPSC-derived cells comprising one or more suicide genes further comprise one or more in/dels comprised in one or more endogenous genes associated with immune response regulation and mediation, including, but not limited to, checkpoint genes, endogenous T cell receptor genes, and MHC class I suppressor genes. In one embodiment, the genome-engineered iPSC-derived cells comprising one or more suicide genes further comprise an in/del in B2M gene, wherein the B2M is knocked-out.

Additionally, applicable dedifferentiation methods and compositions for obtaining genomic-engineered hematopoietic cells of a first fate to genomic-engineered hematopoietic cells of a second fate include those depicted in, for example, International Pub. No. WO2011/159726, the disclosure of which is incorporated herein by reference. The method and composition provided therein allows partially reprogramming a starting non-pluripotent cell to a non-pluripotent intermediate cell by limiting the expression of endogenous Nanog gene during reprogramming; and subjecting the non-pluripotent intermediate cell to conditions for differentiating the intermediate cell into a desired cell type. In some embodiments, the genomically modified iPSCs and their derivative cells obtained using the methods and composition herein comprise at least one genotype listed in Table 1.

V. Therapeutic Use of Combined Synthetic Effector Cell Types Differentiated from Genetically Engineered iPSCs The present invention provides, in some embodiments, a composition comprising two or more synthetic effector cell types or two or more populations of different synthetic effector cell types, where each of the synthetic effector cells have been differentiated from genomically engineered iPSCs using the methods and compositions as disclosed. In some embodiments, the engineered iPSCs comprise one or more targeted genetic edits which are retainable in the iPSC-derived effector cells, resulting in synthetic effector cells having enhanced functional modalities, wherein the genetically engineered iPSCs and derivative synthetic effector cells are suitable for cell-based adoptive therapies. In one embodiment, the enhanced synthetic effector cells comprise iPSC-derived CD34 cells. In one embodiment, the enhanced synthetic effector cells comprise iPSC-derived HSC cells. In one embodiment, the enhanced synthetic effector cells comprise iPSC-derived proT or T cells. In one embodiment, the enhanced synthetic effector cells comprise iPSC-derived proNK or NK cells. In one embodiment, the enhanced synthetic effector cells comprise iPSC-derived immune regulatory cells or myeloid derived suppressor cells (MDSCs).

In some embodiments, the iPSC-derived enhanced synthetic effector cells are further modulated ex vivo for improved therapeutic potential. In one embodiment, at least one of the isolated populations or subpopulations of enhanced synthetic effector cells that have been derived from iPSCs comprises an increased number or ratio of naïve T cells, stem cell memory T cells, and/or central memory T cells. In one embodiment, at least one of the isolated populations or subpopulations of enhanced synthetic effector cells that have been derived from iPSCs comprises an increased number or ratio of type I NKT cells. In another embodiment, at least one of the isolated populations or subpopulations of enhanced synthetic effector cells that have been derived from iPSCs comprises an increased number or ratio of adaptive NK cells. In some embodiments, at least one of the isolated populations or subpopulations of enhanced synthetic CD34 cells, HSC cells, T cells, NK cells, or myeloid derived suppressor cells derived from iPSCs is allogeneic. In some other embodiments, at least one of the isolated populations or subpopulations of enhanced synthetic CD34 cells, HSC cells, T cells, NK cells, or MDSCs derived from iPSCs is autologous.

In some embodiments of the composition comprising two or more synthetic effector cell types or two or more populations of different synthetic effector cell types, where each of the synthetic effector cells have been differentiated from genomically engineered iPSCs, the first type of synthetic effector cell is a functionally enhanced iPSC-derived T cell, and the second type of synthetic effector cell is a functionally enhanced iPSC-derived NK cell. In some embodiments, the functionally enhanced iPSC-derived T cells comprise at least a first CAR. In some embodiments, the functionally enhanced iPSC-derived NK cell comprises at least a second CAR, and one or both of a CD16 variant and a partial or full length of an exogenous cell surface expressed cytokine and/or a receptor thereof. In some embodiments, the two different types of synthetic effector cells are in two separate populations. In some embodiments, the two separate populations of synthetic effector cells are combined into a mixed population (i.e., the two populations are mixed).

In some embodiments, the iPSCs for differentiation comprise additional genetic imprints selected to convey desirable therapeutic attributes in derived effector cells, provided that cell development biology during differentiation is not disrupted, and provided that the genetic imprints are retained and functional in the differentiated hematopoietic cells derived from said iPSC.

In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC-derived hematopoietic lineage cells.

In some embodiments, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells therefrom.

In still some other embodiments, the iPSC-derived hematopoietic lineage cells comprise the therapeutic attributes of the source specific immune cell relating to a combination of at least two of the following: (i) expression of one or more antigen targeting receptors; (ii) modified HLA; (iii) resistance to tumor microenvironment; (iv) recruitment of bystander immune cells and immune modulations; (iv) improved on-target specificity with reduced off-tumor effect; and (v) improved homing, persistence, cytotoxicity, or antigen escape rescue.

In some embodiments, the synthetic effector cells described herein and/or compositions comprising first and second populations of synthetic effector cells are useful in treating and/or ameliorating various diseases. In one embodiment of the method of treating a subject using the composition as provided herein, the method comprises administering a first synthetic cell population that comprises iPSC-derived NK cells, wherein the iPSC-derived NK cells comprise: (a) a high affinity non-cleavable CD16 (hnCD16) or a variant thereof; and (b) one or both of a first chimeric antigen receptor (CAR), and a partial or full length peptide of an exogenous cell surface expressed cytokine or a receptor thereof; and administering a second synthetic cell population that comprises iPSC-derived T cells, wherein the iPSC-derived T cells comprise: at least a second chimeric antigen receptor (CAR), wherein the second CAR is expressed under the control of an endogenous promoter of said TCR locus, and wherein the first CAR and the second CAR have the same or different targeting specificity. This method, as disclosed, provides, among many other advantages, durable responses in cytotoxicity, multi-antigen targeting, and is effective to overcome tumor antigen escape, and has diverse applications in multiple lines of indication.

In some embodiments, the iPSC-derived hematopoietic cells comprise a genotype listed in Table 1, and said cells express at least one cytokine and/or its receptor comprising IL2, IL4, IL6, IL7, IL9, IL10, IL11, IL12, IL15, IL18, or IL21, or any modified protein thereof, and express at least a CAR. In some embodiments, the engineered expression of the cytokine(s) and the CAR(s) is NK cell specific. In some other embodiments, the engineered expression of the cytokine(s) and the CAR(s) is T cell specific. In one embodiment, the CAR of the derivative hematopoietic cell comprises a binding domain recognizing any one of CD19, BCMA, CD20, CD22, CD38, CD123, HER2, CD52, EGFR, GD2, and PDL1 antigen. In some embodiments, the antigen specific iPSC-derived effector cells target a liquid tumor. In some embodiments, the antigen specific iPSC-derived effector cells target a solid tumor/cancer. In some embodiments, the antigen specific iPSC-derived effector cells are capable of rescuing tumor antigen escape.

A variety of diseases may be treated and/or ameliorated by introducing two or more types of the synthetic effector cells of the invention to a subject suitable for adoptive cell therapy. In some embodiments, the two or more types of iPSC-derived hematopoietic cells are provided for allogeneic adoptive cell therapies. Additionally, the present invention provides, in some embodiments, therapeutic use of the above therapeutic compositions by introducing the composition comprising two or more types of iPSC-derived effector cells to a subject suitable for adoptive cell therapy, wherein the subject has an autoimmune disorder; a hematological malignancy; a solid tumor; or an infection associated with HIV, RSV, EBV, CMV, adenovirus, or BK polyomavirus.

Examples of hematological malignancies include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes. Examples of solid cancers include, but are not limited to, cancer of the brain, prostate, breast, lung, colon, uterus, skin, liver, bone, pancreas, ovary, testes, bladder, kidney, head, neck, stomach, cervix, rectum, larynx, and esophagus. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV- (human immunodeficiency virus), HSV- (herpes simplex virus), KSHV- (Kaposi's sarcoma-associated herpesvirus), RSV- (Respiratory Syncytial Virus), EBV- (Epstein-Barr virus), CMV- (cytomegalovirus), VZV (Varicella zoster virus), adenovirus-, a lentivirus-, a BK polyomavirus-associated disorders.

The treatment using a composition comprising two or more types of iPSC-derived hematopoietic lineage cells as disclosed herein could be carried out upon symptom presentation, or for relapse prevention or treatment. The terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any intervention of a disease in a subject and includes: preventing the disease from occurring in a subject which may be predisposed to the disease but has not yet been diagnosed as having it; and inhibiting the disease, i.e., arresting its development; or relieving the disease, i.e., causing regression of the disease. The composition comprising two or more types of iPSC-derived hematopoietic lineage cells may be administered before, during or after the onset of a disease or an injury. Treatment of ongoing disease, where the treatment stabilizes or reduces the undesirable clinical symptoms of the patient, is also of particular interest. In particular embodiments, the subject in need of a treatment has a disease, a condition, and/or an injury that can be contained, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g., a hyperproliferative disorder or a cancer of hematopoietic system, a subject having or at risk of developing a tumor, e.g., a solid tumor, a subject who has or is at risk of having a viral infection or a disease associated with a viral infection.

When evaluating responsiveness to the treatment with a composition comprising two or more types of iPSC-derived hematopoietic lineage cells as disclosed herein, the response can be measured by criteria comprising at least one of: clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST (Response Evaluation Criteria In Solid Tumors) criteria.

The therapeutic composition comprising two or more types of iPSC-derived hematopoietic lineage cells as disclosed herein can be administered to a subject before, during, and/or after other treatments. As such, a method of combinational therapy is provided, which can involve the administration or preparation of the two or more iPSC-derived effector cell types before, during, and/or after the use of an additional therapeutic agent. In one embodiment, the composition comprises two or more synthetic effector cell types derived from genomically engineered iPSCs, wherein the composition comprises at least one or two or more of: iPSC-derived NK cells, iPSC-derived T cells, iPSC-derived CD34$^+$ HE cells, iPSC-derived HSCs, iPSC-derived NKT cells, iPSC-derived B cells, iPSC-derived T progenitors, iPSC-derived NK progenitors, and iPSC-derived MDSCs, which cells are made by the methods and compositions disclosed herein. A composition comprising two or more types of iPSC-derived hematopoietic lineage cells as disclosed herein can be administered concurrently or consecutively by intravenous, intraperitoneal, enteral, or tracheal administration methods. In some embodiments, when the two types of derivative effector cells are administered concurrently, each type of cell is in its respective separate population, or the two types of derivative effector cells are administered in one mixed population. In some embodiments, each population of the composition is administered concurrently or consequently with one or more suitable therapeutic agents to effect the desired treatment goals.

As provided above, the one or more additional therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). Immunomodulatory drugs (IMiDs) such as thalidomide, lenalidomide, and pomalidomide stimulate both NK cells and T cells. As provided herein, IMiDs may be used with the iPSC-derived therapeutic effector cells for cancer treatments.

The administration of the two or more types of iPSC-derived effector cells can be separated in time from the administration of an additional therapeutic agent by hours, days, or even weeks. Additionally, or alternatively, the administration can be combined with other biologically active agents or modalities such as, but not limited to, an antineoplastic agent, or a non-drug therapy, such as, surgery.

In some embodiments of a combinational cell therapy, the therapeutic composition comprising the two or more types of iPSC-derived hematopoietic lineage cells provided herein comprises an additional therapeutic agent that is an antibody, or an antibody fragment. In some embodiments, the antibody is a monoclonal antibody. In some embodiments, the antibody may be a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC-derived hematopoietic lineage cells to enhance their killing ability. In some embodiments, the antibodies suitable for combinational treatment as an additional therapeutic agent to the administered iPSC-derived hematopoietic lineage cells include, but are not limited to, anti-CD20 (e.g., rituximab, veltuzumab, ofatumumab, ublituximab, ocaratuzumab, obinutuzumab, ibritumomab, ocrelizumab), anti-CD22 (inotuzumab, moxetumomab, epratuzumab), anti-HER2 (e.g., trastuzumab, pertuzumab), anti-CD52 (e.g., alemtuzumab), anti-EGFR (e.g., certuximab), anti-GD2 (e.g., dinutuximab), anti-PDL1 (e.g., avelumab), anti-CD38 (e.g., daratumumab, isatuximab, MOR202), anti-CD123 (e.g., 7G3, CSL362), anti-SLAMF7 (elotuzumab), and their humanized or Fc modified variants or fragments or their functional equivalents or biosimilars.

In some embodiments, the additional therapeutic agent comprises one or more checkpoint inhibitors. Checkpoints are cell molecules, often cell surface molecules, capable of suppressing or downregulating immune responses when not inhibited. Checkpoint inhibitors are antagonists capable of reducing checkpoint gene expression or gene products, or deceasing activity of checkpoint molecules. Suitable checkpoint inhibitors for combination therapy with the derivative effector cells provided herein include, but are not limited to, antagonists of PD-1 (Pdcdl, CD279), PDL-1 (CD274), TIM-3 (Havcr2), TIGIT (WUCAM and Vstm3), LAG-3 (Lag3, CD223), CTLA-4 (Ctla4, CD152), 2B4 (CD244), 4-1BB (CD137), 4-1BBL (CD137L), $A_{2A}R$, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

Some embodiments of the combination therapy comprising the provided two or more types of derivative effector cells further comprise at least one inhibitor targeting a checkpoint molecule. Some other embodiments of the combination therapy with the provided two or more types of derivative effector cells comprise two, three or more inhibitors such that two, three, or more checkpoint molecules are targeted. In some embodiments, the two types of effector cells for combination therapy as described herein include a population of derivative T cells and a population of derivative NK cells as provided. In some embodiments, the derivative T or NK cells are functionally enhanced as provided herein. In some embodiments, the two, three or more checkpoint inhibitors may be administered in a combination therapy with, before, or after the administering of the two types of derivative effector cells. In some embodiments, the two or more checkpoint inhibitors are administered at the same time, or one at a time (sequential).

In some embodiments, the antagonist inhibiting any of the above checkpoint molecules is an antibody. In some embodiments, the checkpoint inhibitory antibodies may be murine antibodies, human antibodies, humanized antibodies, a camel Ig, a shark heavy-chain-only antibody (VNAR), Ig NAR, chimeric antibodies, recombinant antibodies, or antibody fragments thereof. Non-limiting examples of antibody fragments include Fab, Fab', F(ab')2, F(ab')3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab, avelumab, durvalumab, ipilimumab, IPH4102, IPH43, IPH33, lirimumab, monalizumab, nivolumab, pembrolizumab, and their derivatives or functional equivalents.

The combination therapies comprising the two types of derivative effector cells and one or more checkpoint inhibitors are applicable to treatment of liquid and solid cancers, including but not limited to cutaneous T-cell lymphoma, non-Hodgkin lymphoma (NHL), Mycosis fungoides, Pagetoid reticulosis, Sezary syndrome, Granulomatous slack skin, Lymphomatoid papulosis, *Pityriasis lichenoides* chronica, *Pityriasis lichenoides* et varioliformis acuta, CD30+ cutaneous T-cell lymphoma, Secondary cutaneous CD30+ large cell lymphoma, non-mycosis fungoides CD30 cutaneous large T-cell lymphoma, Pleomorphic T-cell lymphoma, Lennert lymphoma, subcutaneous T cell lymphoma, angiocentric lymphoma, blastic NK-cell lymphoma, B cell Lymphomas, hodgkins lymphoma (HL), Head and neck tumor; Squamous cell carcinoma, rhabdomyocarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, pancreatic cancer, thyroid papillary cancer, intrahepatic cholangiocellular carcinoma, hepatocellular carcinoma, bone cancer, metastasis, and nasopharyngeal carcinoma.

In some embodiments, other than the two types of derivative effector cells as provided herein, a combination for therapeutic use further comprises one or more additional therapeutic agents comprising a chemotherapeutic agent or a radioactive moiety. As used herein, chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's The Pharmacological Basis of Therapeutics, Ninth Edition, McGraw-Hill, N.Y., 1995) or through the National Cancer Institute website (fda.gov/cder/cancer/druglistfrarne.htm), both as updated from time to time.

In one embodiment, the combinational cell therapy comprises a therapeutic protein or peptide that is a CD3 engager and two populations of synthetic effector cells derived from genomically engineered iPSCs, wherein the derived synthetic NK or T cells comprise cell surface CD3 (cs-CD3). In some embodiments, the CD3 engager comprises one of blinatumomab, catumaxomab, ertumaxomab, R06958688, AFM11, MT110/AMG 110, MT111/AMG211/MEDI-565, AMG330, MT112/BAY2010112, MOR209/ES414, MGD006/580880, MGD007, and/or FBTA05. In yet some other embodiments, the CD3 engager comprises one of blinatumomab, catumaxomab, and ertumaxomab, and the derived NK or T cells comprise a CAR targeting CD19, BCMA, CD38, CD20, CD22, or CD123, hnCD16, and cs-CD3. In still some additional embodiments, the CD3 engager comprises one of blinatumomab, catumaxomab, and ertumaxomab, and the synthetic NK or T cells derived from genomically engineered iPSCs comprise cs-CD3, hnCD16, a CAR and one or more exogenous cytokine.

Other than the two or more types of iPSC-derived hematopoietic lineage cells included in the therapeutic compositions, the compositions suitable for administration to a subject can further include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, $17^{th}$ ed. 1985, the disclosure of which is hereby incorporated by reference in its entirety).

These pharmaceutically acceptable carriers and/or diluents can be present in amounts sufficient to maintain a pH of the therapeutic composition of between about 3 and about 10. As such, a buffering agent can be as much as about 5% on a weight to weight basis of the total composition. Electrolytes such as, but not limited to, sodium chloride and potassium chloride can also be included in the therapeutic composition. In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, the therapeutic composition includes a buffer having a pH in one of said pH ranges. In another embodiment, the therapeutic composition has a pH of about 7. Alternatively, the therapeutic composition has a pH in a range from about 6.8 to about 7.4. In still another embodiment, the therapeutic composition has a pH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the iPSC-derived effector cells in accordance with embodiments of the invention are suitable for use as a pharmaceutical cell culture medium. In particular embodiments, the pharmaceutically acceptable cell culture medium is a serum free, and/or feeder-free medium. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

The iPSC-derived hematopoietic lineage cells can have at least 50%, 60%, 70%, 80%, 90%, 95%, 98%, or 99% T cells, NK cells, NKT cells, proT cells, proNK cells, $CD34^+$ HE cells, HSCs, B cells, myeloid-derived suppressor cells (MDSCs), regulatory macrophages, regulatory dendritic cells, or mesenchymal stromal cells. In some embodiments, the iPSC-derived hematopoietic lineage cells have about 95% to about 100% T cells, NK cells, proT cells, proNK cells, $CD34^+$ HE cells, or myeloid-derived suppressor cells (MDSCs). In some embodiments, the present invention provides therapeutic compositions having purified T cells or NK cells, such as a composition having an isolated population of about 95% T cells, NK cells, proT cells, proNK cells, $CD34^+$ HE cells, or myeloid-derived suppressor cells (MDSCs) to treat a subject in need of the cell therapy. In a composition as provided herein comprising two or more types of synthetic effector cells derived from engineered iPSCs, the ratio of the two types of cells in cell count is between 100:1 and 1:100, or between 50:1 and 1:50, or between 20:1 to 1:20, or between 10:1 to 1:10, or between 2:1 to 1:2, or in any range in between.

As a person of ordinary skill in the art would understand, both autologous and allogeneic hematopoietic lineage cells derived from iPSC based on the methods and compositions provided herein can be used in therapies utilizing combined cell types as described above. For autologous transplantation, the isolated populations of derived hematopoietic lineage cells are either complete or partial HLA-matched with the subject. In another embodiment, the derived hematopoietic lineage cells are not HLA-matched to the subject, wherein the derived hematopoietic lineage cells are NK cells or T cells with HLA-I and HLA-II null.

In some embodiments, the number of each type of derived hematopoietic lineage cells in the composition is at least $0.1 \times 10^5$ cells, at least $1 \times 10^5$ cells, at least $5 \times 10^5$ cells, at least $1 \times 10^6$ cells, at least $5 \times 10^6$ cells, at least $1 \times 10^7$ cells, at least $5 \times 10^7$ cells, at least $1 \times 10^8$ cells, at least $5 \times 10^8$ cells, at least $1 \times 10^9$ cells, or at least $5 \times 10^9$ cells, per dose, with the cell count ratio of the two types of cells in between 100:1 and 1:100, 50:1 and 1:50, 20:1 to 1:20, 10:1 to 1:10, 2:1 to 1:2, 1:1, or any range in between. In some embodiments, the number of each type of derived hematopoietic lineage cells in the composition is about $0.1 \times 10^5$ cells to about $1 \times 10^6$ cells, per dose; about $0.5 \times 10^6$ cells to about $1 \times 10^7$ cells, per dose; about $0.5 \times 10^7$ cells to about $1 \times 10^8$ cells, per dose; about $0.5 \times 10^8$ cells to about $1 \times 10^9$ cells, per dose; about $1 \times 10^9$ cells to about $5 \times 10^9$ cells, per dose; about $0.5 \times 10^9$ cells to about $8 \times 10^9$ cells, per dose; about $3 \times 10^9$ cells to about $3 \times 10^{10}$ cells, per dose, with the cell count ratio of the two types of cells in between 100:1 and 1:100, 50:1 and 1:50, 20:1 to 1:20, 10:1 to 1:10, 2:1 to 1:2, 1:1, or any range in between. Generally, $1 \times 10^8$ cells/dose translates to $1.67 \times 10^6$ cells/kg for a 60 kg patient/subject.

In one embodiment, the number of each type of the derived hematopoietic lineage cells in the composition is the number of immune cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.75 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, at least $30 \times 10^6$ cells/kg of bodyweight, $1 \times 10^8$ cells/kg of bodyweight, $5 \times 10^8$ cells/kg of bodyweight, or $1 \times 10^9$ cells/kg of bodyweight, with the cell count ratio of the two types of cells in between 100:1 and 1:100, 50:1 and 1:50, 20:1 to 1:20, 10:1 to 1:10, 2:1 to 1:2, 1:1, or any range in between.

In one embodiment, a dose of two types of derived hematopoietic lineage cells is delivered to a subject. In one illustrative embodiment, the effective amount of cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells, with the cell count ratio of the two types of cells in between 100:1 and 1:100, 50:1 and 1:50, 20:1 to 1:20, 10:1 to 1:10, 2:1 to 1:2, 1:1 or any range in between.

In another illustrative embodiment, the effective amount of cells, with the cell count ratio of the two types of cells in between 100:1 and 1:100, 50:1 and 1:50, 20:1 to 1:20, 10:1 to 1:10, 2:1 to 1:2, 1:1 or any range in between, provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of cells, with the cell count ratio of the two types of cells in between 100:1 and 1:100, 50:1 and 1:50, 20:1 to 1:20, 10:1 to 1:10, 2:1 to 1:2, 1:1 or any range in between, provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

In some embodiments, the therapeutic use of the composition comprising two or more types of derived hematopoietic lineage cells is a single-dose treatment, wherein the two or more types of cells are administered concurrently or consecutively. In some embodiments, the therapeutic use of the composition comprising two or more types of derived hematopoietic lineage cells is a multi-dose treatment. In some embodiments, the multi-dose treatment is one dose every day, every 3 days, every 7 days, every 10 days, every 15 days, every 20 days, every 25 days, every 30 days, every 35 days, every 40 days, every 45 days, or every 50 days, or any number of days in-between, with each dose of the two types of cells being administered concurrently or consecutively.

In some embodiments, the compositions comprising two or more types of synthetic effector cells that are derived from engineered iPSC can be sterile, post-thaw, and can be suitable and ready for administration (i.e., can be administered without any further processing) to human patients/subjects. A cell-based composition that is ready for administration means that the composition does not require any further processing or manipulation prior to transplant or administration to a subject. In other embodiments, the invention provides two or more types of isolated populations of derived hematopoietic lineage cells that are expanded and/or modulated prior to administration with one or more agents including small chemical molecules. The modulation may be through contacting the derived hematopoietic lineage cells with a small chemical molecule, a protein, a nucleic acid, or a selected cell or a cell component thereof. The compositions and methods for modulating immune cells including iPSC-derived effector cells are described in greater detail, for example, in International Pub. No. WO2017/127755, the relevant disclosure of which is incorporated herein by reference. For derived hematopoietic lineage cells that genetically engineered to express recombinant TCR or CAR, the cells can be activated and expanded using methods as described, for example, in U.S. Pat. No. 6,352,694.

In certain embodiments, the primary stimulatory signal and the co-stimulatory signal for the derived hematopoietic lineage cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Pub. Nos. 2004/0101519 and 2006/0034810, the disclosures of which are incorporated by reference, for artificial antigen presenting cells (aAPCs) that are contemplated for use in activating and expanding T lymphocytes in embodiments of the present invention.

Some variation in dosage, frequency, and protocol will necessarily occur depending on the condition of the subject being treated. The person responsible for administration will, in any event, determine the appropriate dose, frequency and protocol for the individual subject.

EXAMPLES

The following examples are offered by way of illustration and not by way of limitation.

Example 1—Materials and Methods

To effectively select and test suicide systems under the control of various promoters in combination with different safe harbor loci integration strategies, a proprietary iPSC platform of the applicant was used, which enables single cell passaging and high-throughput, 96-well plate-based flow cytometry sorting, to allow for the derivation of clonal iPSCs with single or multiple genetic modulations.

iPSC Maintenance in Small Molecule Culture: iPSCs were routinely passaged as single cells once confluency of the culture reached 75%-90%. For single-cell dissociation, iPSCs were washed once with PBS (Mediatech) and treated with Accutase (Millipore) for 3-5 min at 37° C. followed with pipetting to ensure single-cell dissociation. The single-cell suspension was then mixed in equal volume with conventional medium, centrifuged at 225×g for 4 min, resuspended in FMM, and plated on Matrigel-coated surface. Passages were typically 1:6-1:8, transferred tissue culture plates previously coated with Matrigel for 2-4 hr in 37° C. and fed every 2-3 days with FMM. Cell cultures were maintained in a humidified incubator set at 37° C. and 5% $CO_2$.

Human iPSC engineering with ZFN, CRISPR for targeted editing of modalities of interest: Using ROSA26 targeted insertion as an example, for ZFN mediated genome editing, 2 million iPSCs were transfected with a mixture of 2.5 µg ZFN-L (FTV893), 2.5 µg ZFN-R (FTV894) and 5 ug donor construct, for AAVS1 targeted insertion. For CRISPR mediated genome editing, 2 million iPSCs were transfected with mixture of 5 µg ROSA26-gRNA/Cas9 (FTV922) and 5 ug donor construct, for ROSA26 targeted insertion. Transfection was done using Neon transfection system (Life Technologies) using parameters 1500V, 10 ms, 3 pulses. On day 2 or 3 after transfection, transfection efficiency was measured using flow cytometry if the plasmids contain artificial promoter-driver GFP and/or RFP expression cassette. On day 4 after transfection, puromycin was added to the medium at concentration of 0.1 ug/ml for the first 7 days and 0.2 µg/ml after 7 days to select the targeted cells. During the puromycin selection, the cells were passaged onto fresh matrigel-coated wells on day 10. On day 16 or later of puromycin selection, the surviving cells were analyzed by flow cytometry for $GFP^+$ iPS cell percentage.

Bulk sort and clonal sort of genome-edited iPSCs: iPSCs with genomic targeted editing using ZFN or CRISPR-Cas9 were bulk sorted and clonal sorted of $GFP^+SSEA4^+TRA181^+$ iPSCs after 20 days of puromycin selection. Single cell dissociated targeted iPSC pools were resuspended in chilled staining buffer containing Hanks' Balanced Salt Solution (MediaTech), 4% fetal bovine serum (Invitrogen), 1× penicillin/streptomycin (Mediatech) and 10 mM Hepes (Mediatech); made fresh for optimal performance. Conjugated primary antibodies, including SSEA4-PE, TRA181-Alexa Fluor-647 (BD Biosciences), were added to the cell solution and incubated on ice for 15 minutes. All antibodies were used at 7 µL in 100 µL staining buffer per million cells. The solution was washed once in staining buffer, spun down at 225 g for 4 minutes and resuspended in staining buffer containing 10 µM Thiazovivn and maintained on ice for flow cytometry sorting. Flow cytometry sorting was performed on FACS Aria II (BD Biosciences). For bulk sort, $GFP^+SSEA4^+TRA181^+$ cells were gated and sorted into 15 ml canonical tubes filled with 7 ml FMM. For clonal sort, the sorted cells were directly ejected into 96-well plates using the 100 µM nozzle, at concentrations of 3 events per well. Each well was prefilled with 200 µL FMM supplemented with 5 µg/mL fibronectin and 1× penicillin/streptomycin (Mediatech) and previously coated overnight with 5×Matrigel. 5× Matrigel precoating includes adding one aliquot of Matrigel into 5 mL of DMEM/F12, then incubated overnight at 4° C. to allow for proper resuspension and finally added to 96-well plates at 50 μL per well followed by overnight incubation at 37° C. The 5×Matrigel is aspirated immediately before the addition of media to each well. Upon completion of the sort, 96-well plates were centrifuged for 1-2 min at 225 g prior to incubation. The plates were left undisturbed for seven days. On the seventh day, 150 μL of medium was removed from each well and replaced with 100 μL FMM. Wells were refed with an additional 100 μL FMM on day 10 post sort. Colony formation was detected as early as day 2 and most colonies were expanded between days 7-10 post sort. In the first passage, wells were washed with PBS and dissociated with 30 μL Accutase for approximately 10 min at 37° C. The need for extended Accutase treatment reflects the compactness of colonies that have sat idle in culture for prolonged duration. After cells are seen to be dissociating, 200 μL of FMM is added to each well and pipetted several times to break up the colony. The dissociated colony is transferred to another well of a 96-well plate previously coated with 5×Matrigel and then centrifuged for 2 min at 225 g prior to incubation. This 1:1 passage is conducted to spread out the early colony prior to expansion. Subsequent passages were done routinely with Accutase treatment for 3-5 min and expansion of 1:4-1:8 upon 75-90% confluency into larger wells previously coated with 1× Matrigel in FMM. Each clonal cell line was analyzed for GFP fluorescence level and TRA1-81 expression level. Clonal lines with near 100% GFP$^+$ and TRA1-81$^+$ were selected for further PCR screening and analysis. Flow cytometry analysis was performed on Guava EasyCyte 8 HT (Millipore) and analyzed using Flowjo (FlowJo, LLC).

Example 2—Enhanced Derivative NK and T Effector Cells

Derivative NK cells from CAR-expressing iPSCs were obtained according to the directed differentiation platform described herein. NK cell maturation was enhanced in the synthetic hnCD16-CAR-IL-15/IL-15Ra iNK cells, as demonstrated by increased production of granzyme B associated with NK killing ability and increased expression of KIR2DL3 and KIR2DL1, conferring licensing status for the NK cells to acquire effector functions. In vitro cytotoxicity of hnCD16-CAR-IL15/IL15Ra iNK cells against Nalm6 and ARH-77 target cell lines were investigated, which showed CAR directed CD19 specific killing and rituximab-induced ADCC against B cell malignancies in vitro.

Peripheral blood derived T cells with targeted insertion of a CD19 CAR into the T cell receptor α (TRAC) locus under the transcriptional control of its endogenous regulatory elements were reprogrammed to generate a single cell-derived clonal TRAC-targeted CAR containing master iPSC line (TRAC-CAR TiPSC). At around day 28 of T cell differentiation, the derived cells were able to grow and expand further in suspension in the absence of TCR expression. This synthetic T cell (TRAC-CAR iT) demonstrated in vitro functional capability of eliciting an efficient cytotoxic T lymphocyte response to CD19 antigen challenge with production of effector cytokines (IFNγ, TNFα, IL2), degranulation (CD107a/b, Perforin, Granzyme B), proliferation (>85% entry into cell cycle) and upregulation of activation markers CD69 and CD25. The production of IFNγ and TNFα by mature TRAC-CAR iT cells is markedly higher than primary T cells expressing CAR. The TRAC-CAR iT also targets tumor in an antigen specific manner, and without variability in antigen specific cytotoxicity seen in primary T cells expressing CAR.

Figure 2:
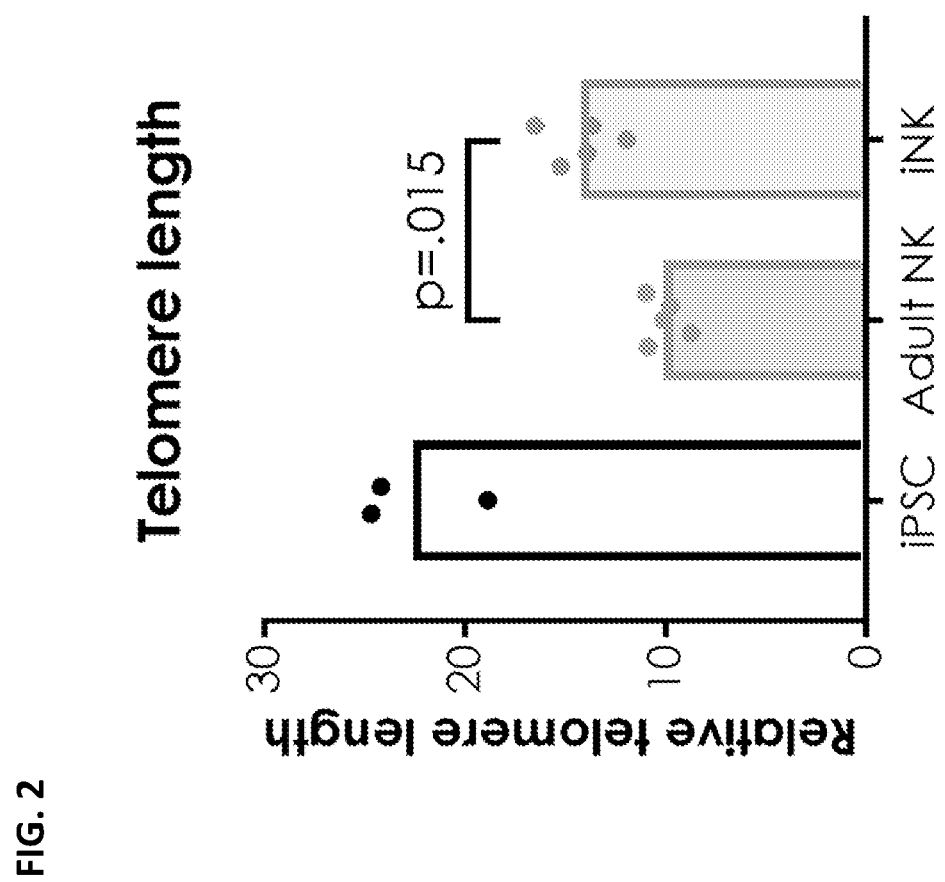
FIG. 2 is a graphic representation of telomere length determined by flow cytometry, and showing that the mature derivative NK cells from iPSC maintain longer telomeres compared to adult peripheral blood NK cells.

It is further shown here that the mature iNK cells obtained through directed differentiation of iPSCs contain longer telomeres compared to adult peripheral blood NK cells. Telomere length was determined by flow cytometry for iPSC, adult peripheral blood NK cells, and iPSC-derived NK cells using the 1301 T cell leukemia line as a control (100%) with correction for the DNA index of $G_{0/1}$ cells. As shown in FIG. 2, iPSC-derived NK cells maintain significantly longer telomere length when compared to adult peripheral blood NK cells (p=0.105, ANOVA), representing greater proliferation, survival and persistence potential in the iPSC-derived NK cells. Similar observation of longer telomere lengthening is also in iPSC-derived T cells. This is consistent with the fact that telomere shortening occurs with cellular aging and is associated with stem cell dysfunction and cellular senescence.

Figure 3:
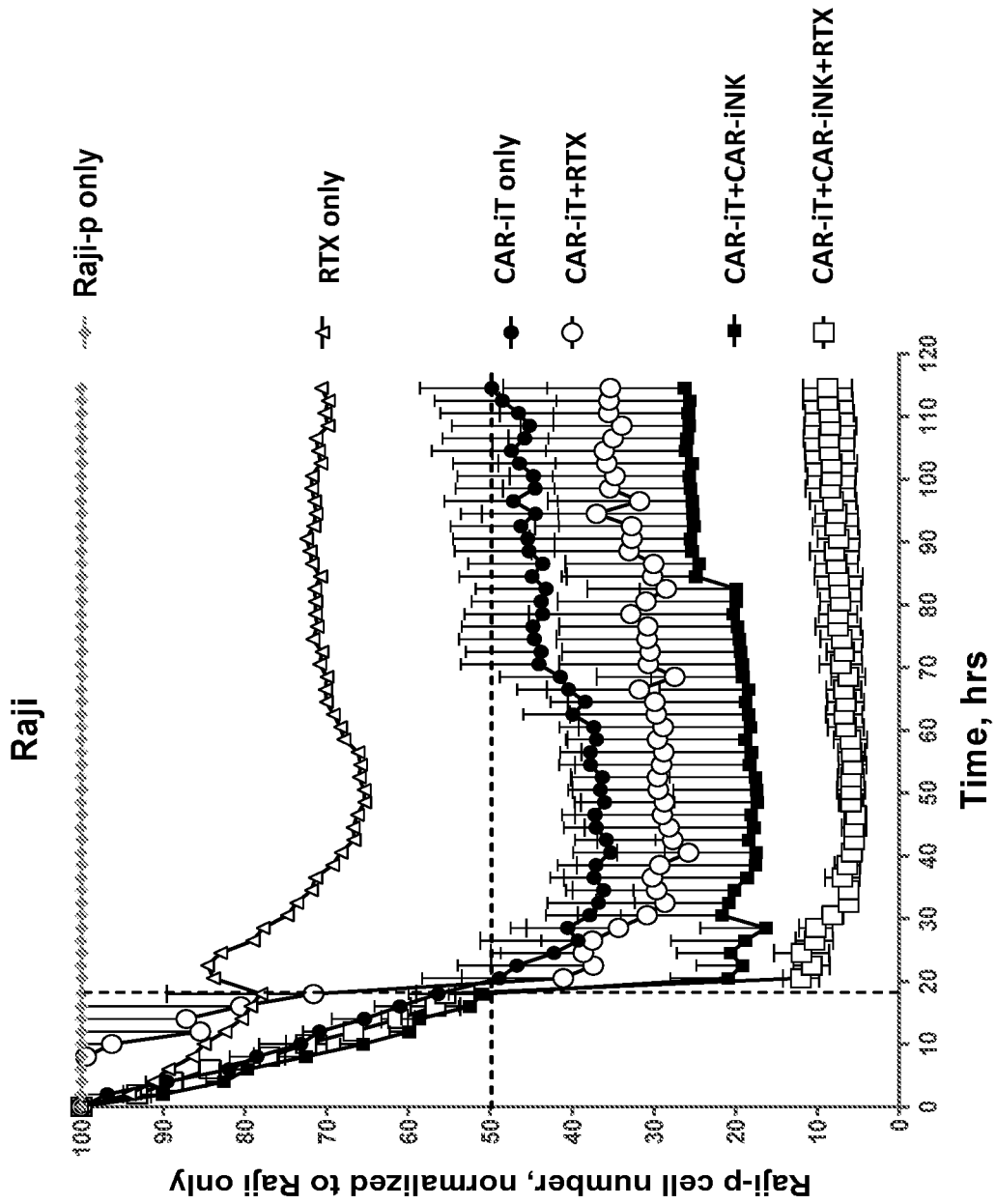
FIG. 3 is a graphic representation showing that sequential addition of CAR-iNK cells improves cytotoxicity of CAR-iT cells, and that the killing of the target tumor cells is further augmented by ADCC.

Example 3—Combination of Effector Cell Types Results in Durable Response Over Multiple Rounds of Cytotoxicity and Multi-Antigen Targeting Raji tumor cells were pre-plated followed by addition of CAR-iT (0.3:1 E:T, o/n), and the subsequent addition either of 0.1 μg/ml RTX (Rituximab), or CAR-iNK and 0.1 ug/ml RTX (0.3:1 E:T ratio) for a total duration of 96 hours. As shown in FIG. 3, the addition of CAR-iNK improves cytotoxicity of CAR-iT, which is augmented further by ADCC.

Figure 4A:
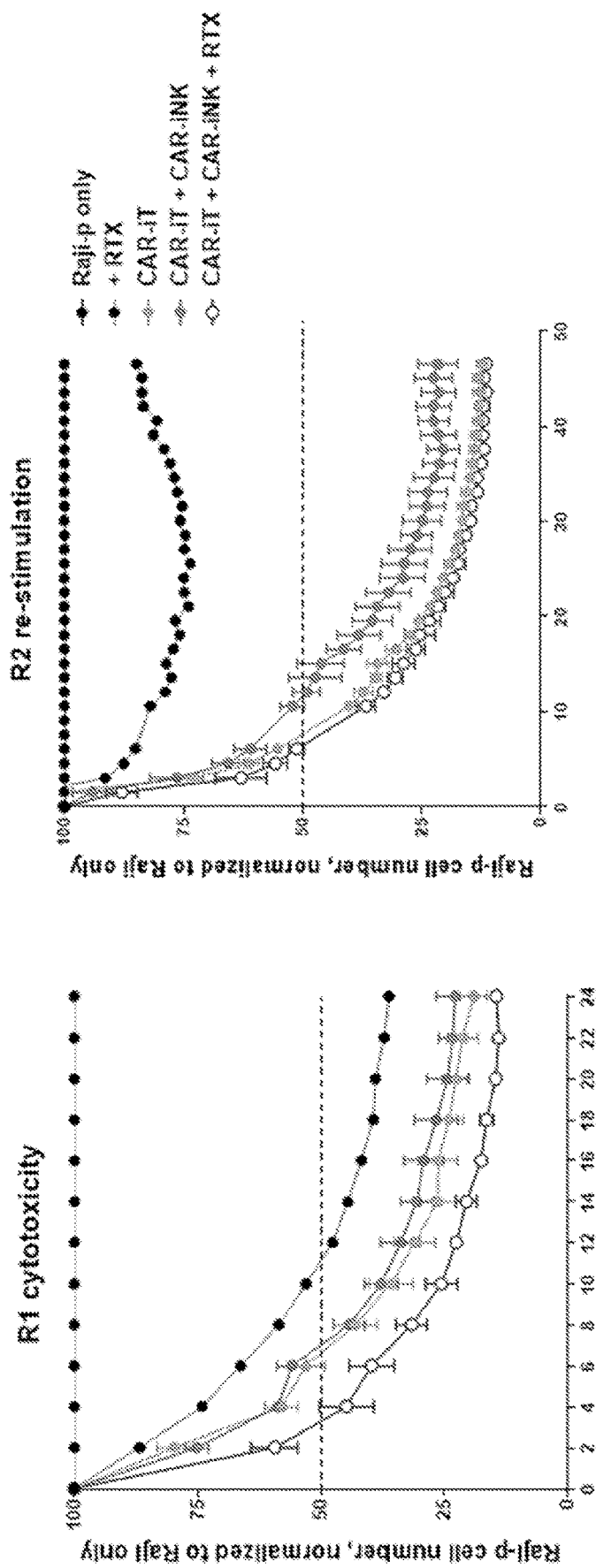
FIGS. 4A and 4B are graphic representations showing the assessment of direct cytotoxicity and ADCC additive effect of CAR-iT and CAR-iNK cells in combination in increased E:T ratio by addition of RTX Raji-parental targets ($CD19^+$; A) and Raji-CD19KO ($CD19^-$; B), with FIG. 4A demonstrating the duo targeting effect, and FIG. 4B further addressing the effector cell combo cytotoxicity to the target cell in a tumor antigen escape setting.
Figure 4B:
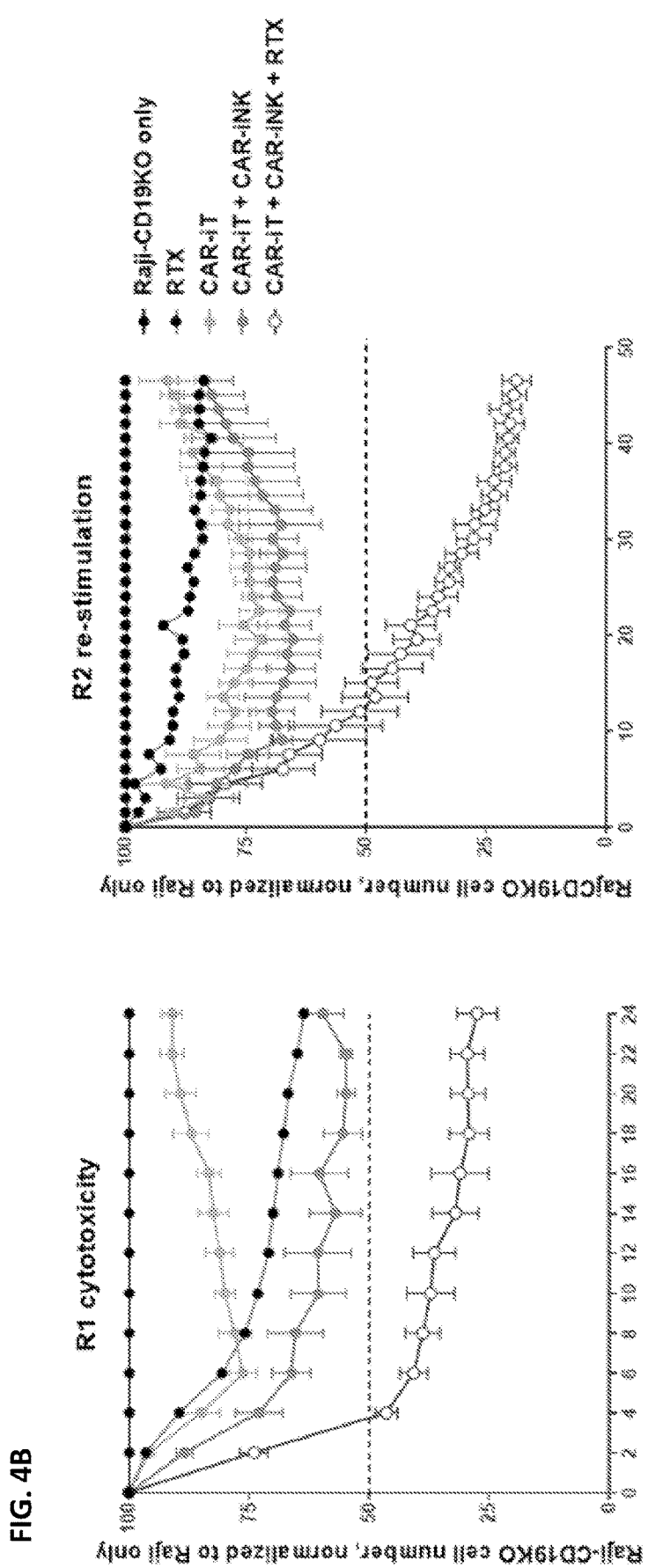

In another assay, the Raji-parental targets (FIG. 4A) and Raji-CD19KO targets (FIG. 4B) were immobilized on the surface of 96 well plates. Targets were pre-cultured as a single type of each, or in a 50/50 combination co-culture to resemble duo targeting mix. As shown in FIG. 4, CAR-iT, CAR-iNK in combination were added in increased E:T ratios, and the combination of the cell products was shown to enable cytotoxicity/targeting in a CD19 antigen escape setting (FIG. 4B), and the further addition of RTX enabled the effect of direct cytotoxicity through ADCC (FIGS. 4A and 4B) resulting in enhanced target elimination.

Figure 5A:
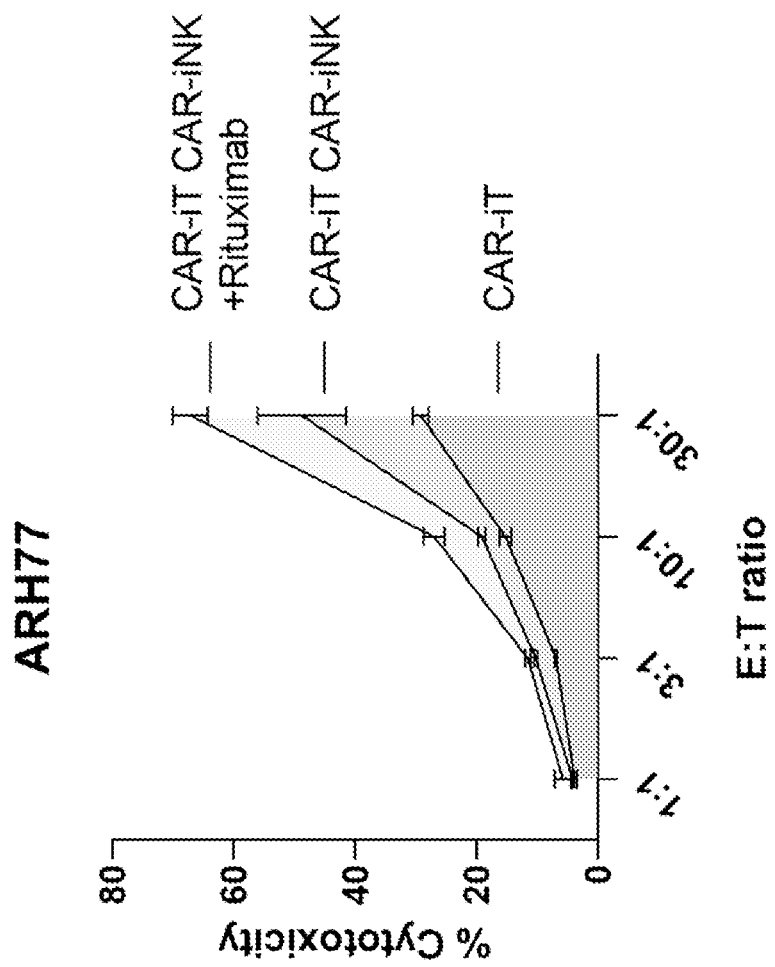
FIG. 5A is a graphic representation showing the titration of effector to target ratios against target cell line ARH-77 ($CD19^+CD20^+$), demonstrating additive increases in antitumor activity with CAR-iT alone, CAR-iT and CAR-iNK, and CAR-iT and CAR-iNK in combination with rituximab.

Example 4—Combination of Effector Cell Types with mAb Increases Efficacy in Diverse B Cell Malignancies Combinations of CAR-iT, CAR-iNK and rituximab were tested against a panel of different tumor cell lines representing B cell malignancies, as well as a primary B cell line transformed with Epstein Barr Virus (EBV), such as the ARH-77 cell line. FIG. 5A shows increases in anti-tumor activity with CAR-iT alone, CAR-iT and CAR-iNK, and CAR-iT and CAR-iNK in combination with Rituximab (0.1 μg/mL) under the titration of effector to target ratios against target cell line ARH-77 (CD19$^+$CD20$^+$). As shown, the combination of both CAR-iT and CAR-iNK in addition to RTX has the highest cytotoxicity.

Figure 5B:
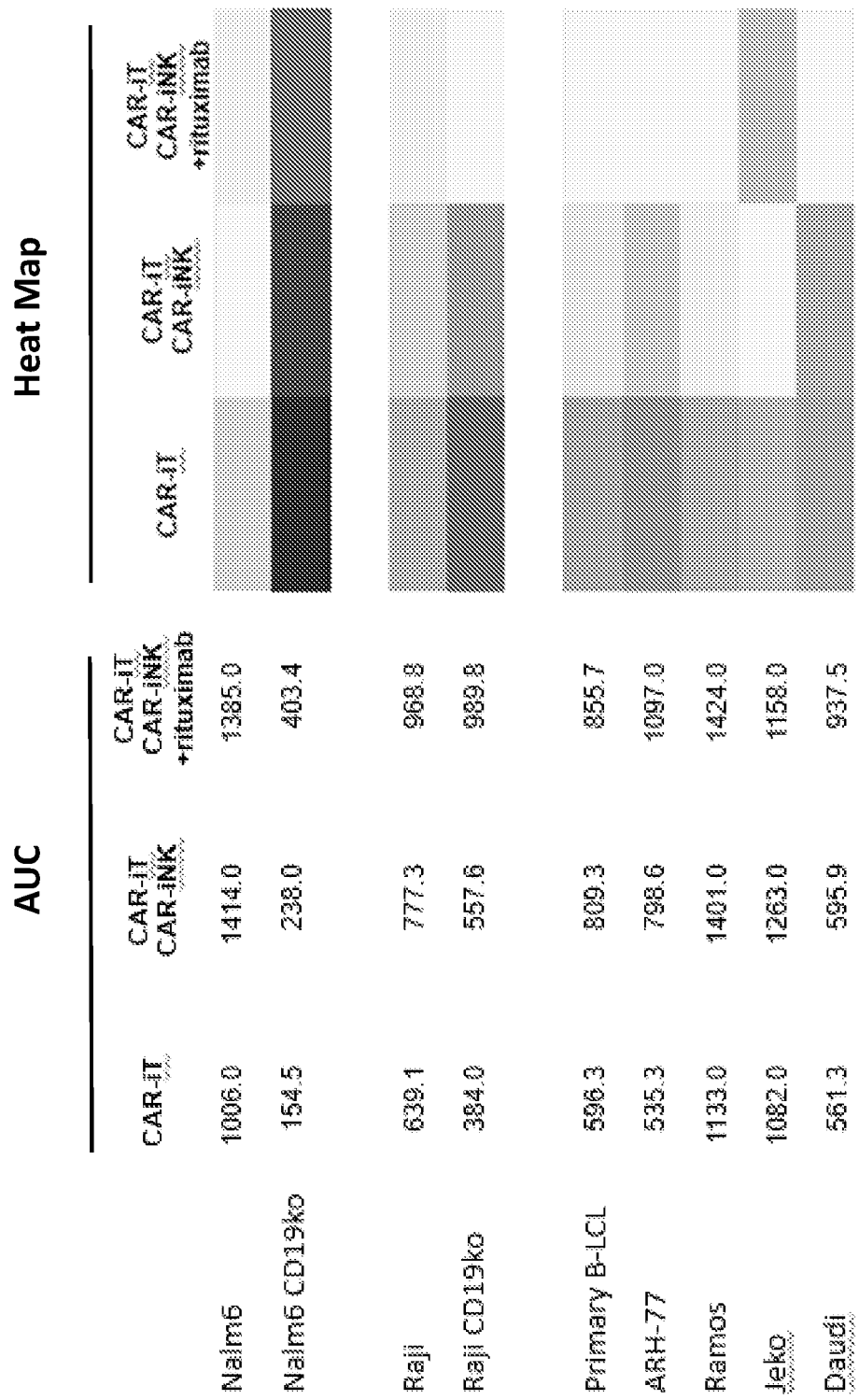
FIG. 5B shows relative activity of CAR-iT alone, CAR-iT and CAR-iNK, and CAR-iT and CAR-iNK in combination with rituximab versus a panel of B tumor lines, calculated as area under the curve (AUC) and illustrated in a heatmap.

Relative activity of CAR-iT, CAR-iNK and rituximab versus a panel of diverse B tumor lines is calculated as area under the curve (AUC) and pictured in the heatmap shown in FIG. 5B. Nalm-6 (CD19$^+$, CD20$^-$) was used as a control to confirm CD19 specificity. As shown in FIG. 5B, the reactivity and the breadth of reactivity across the diverse B cell malignancies increases with the successive addition of CAR-iT alone, CAR-iT and CAR-iNK, and CAR-iT and CAR-iNK in combination with Rituximab (0.1 μg/mL).

Figure 6A:
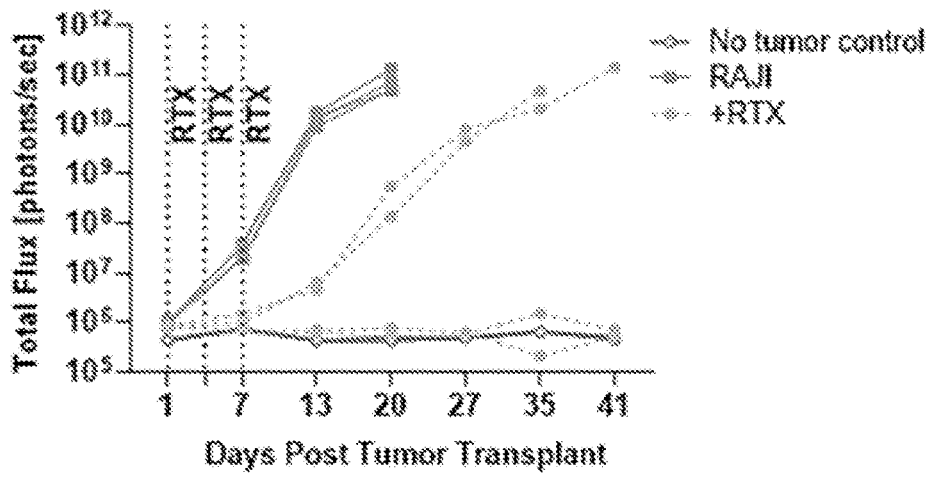
FIGS. 6A-6C are graphic representations showing the results from NSG mice inoculated with RAJI tumor cells and treated with (FIG. 6A) Rituximab alone, (FIG. 6B) primary CAR-T cells, and (FIG. 6C) a combination of CAR-iT, CAR-iNK and rituximab.
Figure 6B:
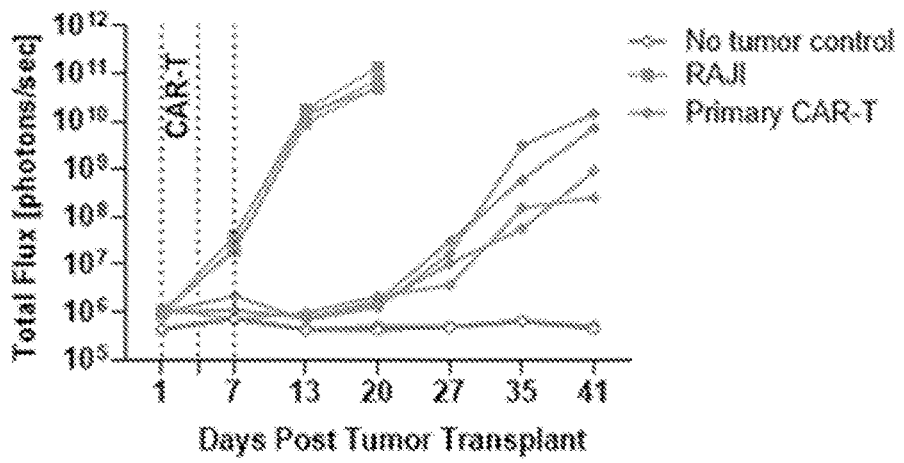
Figure 6C:
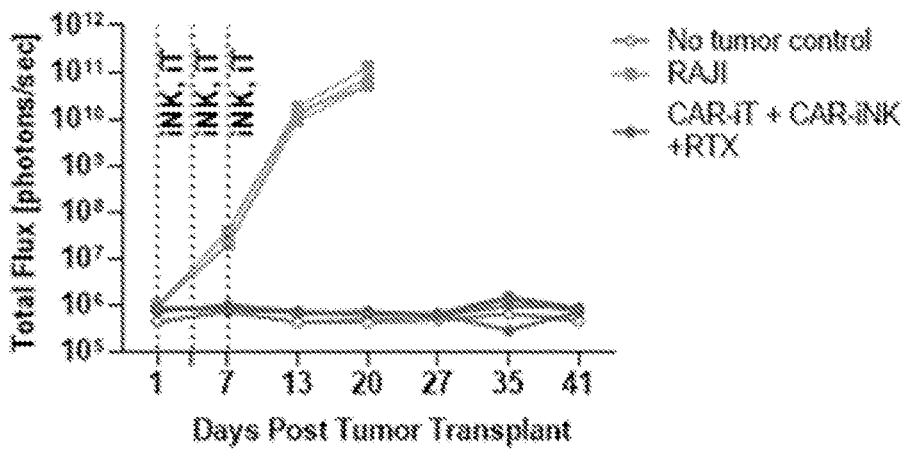
Figure 6D:
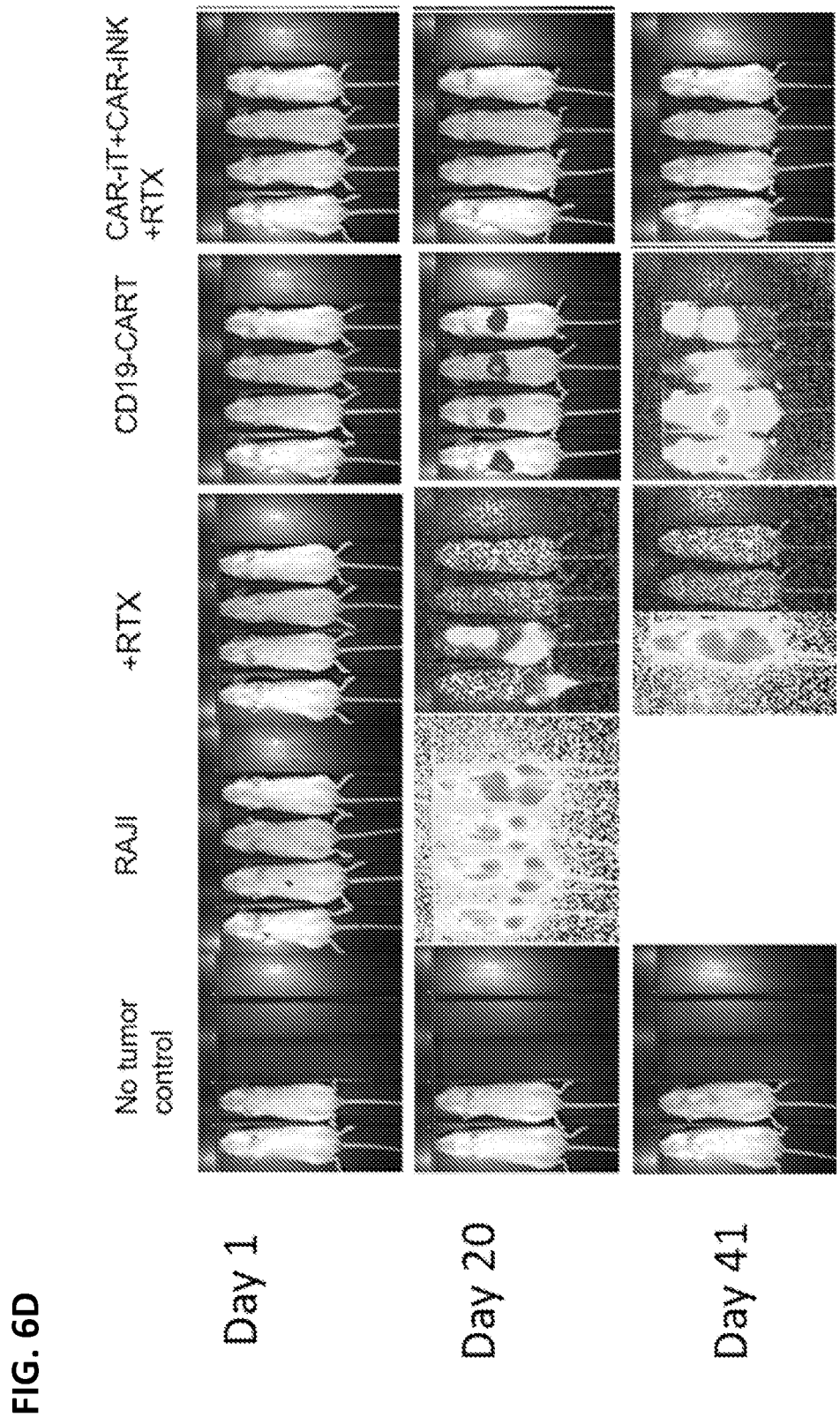
FIG. 6D shows IVIS images of each mouse over a period of 41 days post injection demonstrating effective clearing of Raji tumor cells in an in vivo lymphoma model using a combination of CAR-iT, CAR-iNK and ADCC function.

An in vivo lymphoma model using NSG mice inoculated with RAJI tumor cells shows that treatment of mice with Rituximab alone (3 doses of 3 μg/mouse over 7 days) was partially effective (FIGS. 6A and 6D). Treatment of mice with primary CAR-T cells was more effective than Rituximab alone (FIGS. 6B and 6D). A combination of CAR-iT, CAR-iNK and Rituximab proved the most effective in clearing Raji tumor cells over a period of 41 days (FIGS. 6C and 6D).

Example 5—Combination of Effector Cell Types and Checkpoint Inhibitor Antagonists Checkpoints are cell molecules, often cell surface molecules, capable of suppressing or downregulating immune responses when not inhibited. Checkpoint inhibitors are antagonists capable of reducing checkpoint gene expression or gene products, or deceasing activity of checkpoint molecules. The development of checkpoint inhibitors (CI) targeting PD1/PDL1 or CTLA4 has transformed the oncology landscape, with these agents providing long term remissions in multiple indications. However, many tumor subtypes are resistant to checkpoint blockade therapy, and relapse remains a significant concern. Therefore, novel therapeutic approaches with the ability to overcome CI resistance are needed.

Assays are designed to show whether the derivative NK cells have the ability to both recruit the derivative T cells to the tumor microenvironment (TME) and augment derivative T cell activation at the tumor site. Migration of activated derivative T cells is demonstrated upon secretion of CCL3, CCL4, CXCL10 and other soluble factors by activated derivative NK cells. In this assay, hnCD16 iNK cells are combined with either SKOV-3 or SKOV-3-PDL1 expressing high levels of PDL1 in the presence of an ADCC-inducing anti-PDL1 antibody. After overnight incubation, supernatants are collected and incubated in the lower chamber of a standard transwell chemotaxis chamber with derivative T cells in the upper chamber for 24 hours. After incubation, derivative T cell migration to the lower chamber is quantified by flow cytometry to determine whether activated iNK column cells enhance derivative T cell migration.

It was previously shown that upon activation, the derivative NK cells exhibit direct antitumor capacity evidenced by the cells' production of copious inflammatory cytokines and chemokines, including interferon gammas (IFNγ), CCL3, CCL4, CXCL10, and CCL22. IFNγ plays a critical role in regulating anti-tumor T cell activity. In an in vivo assay, NSG mice are injected with 1E7 iNK cells I.P. (intraperitoneal), or 5E6 activated derivative T cells R.O. (retro-orbital), or both. Four days later, the peripheral blood and peritoneal cavity are assessed for the presence of derivative T cells by flow cytometry. Compared with mice receiving derivative T cells but no derivative NK cells, mice that received iPSC-derived NK cells I.P. were expected to have reduced derivative T cell frequency in peripheral blood and increased derivative T cells in the peritoneal cavity due to the derivative NK cells' ability to enhance derivative T cell migration by recruiting activated derivative T cells out of the circulation and into the peritoneum.

Utilizing an in vitro three-dimensional tumor spheroid model, enhanced infiltration of derivative T cells into tumor spheroids in the presence of the derivative NK cells is observed. 30,000 derivative T cells that are green fluorescently labelled are either incubated alone with SKOV-3 microspheres (red nuclei) or in combination with 15,000 iNK cells and imaged for more than 15 hours. It is expected that derivative T cells alone fail to penetrate the center of the spheroid, but addition of iNK cells promotes derivative T cell infiltration to tumor spheroid and tumor spheroid destruction.

The enhanced derivative T cell infiltration of tumor spheroids and enhanced cytotoxicity when co-cultured with derived NK cells are also shown quantitatively by measuring total integrated green fluorescence intensity within the largest red object mask. Infiltration of derivative T cells into SKOV-3 spheroids is measured for 24 hours of co-culture with derived NK cells (1:1 ratio), CD3$^+$ T cells (2:1 ratio), or iNK (1:1 ratio)+iT cells (2:1 ratio), to show that derived NK cells enhance derivative T cell infiltration of the tumor spheroids.

Co-culture of derivative T cells and derivative NK cells in a 3D tumor spheroid model leads to tumor cell killing and enhanced production of IFNγ and TNFα. After 7 days of derived NK cell incubation with SKOV-3 spheroids in 1:1 ET ratio, CD3$^+$ T cells (2:1 ratio), or iNK (1:1 ratio)+iT cells (2:1 ratio)), supernatants are collected and assessed for TNFα and IFNγ production. iPSC-derived NK cells synergize with derivative T cells in enhancing production of IFNγ and TNFα for solid tumor killing in a spheroid model when co-culture of iT cells with iPSC-NK and led to increased cytokine production for both CD4$^+$ and CD8$^+$ iT cells.

As such, by promoting recruitment of derivative T cells to the tumor site and by enhancing derivative T cell activation and infiltration, these functionally potent derivative NK cells are evidenced to be capable of synergizing with derivative T cell targeted immunotherapies, including the checkpoint inhibitors, to relieve local immunosuppression and to reduce tumor burden in a solid tumor setting. Together, these data provide evidence supporting an allogenic combination therapy comprising derivative NK cells and derivative T cells, optionally further in combination with a checkpoint inhibitor or other T cell targeted therapeutic agents.

Suitable checkpoint inhibitors for a combinational therapy with the derivative NK and derivative T cell combo are disclosed herein.

The combination therapies comprising the derivative NK and derivative T cell and optionally one or more checkpoint inhibitors are applicable to treatment of liquid and solid cancers. When evaluating responsiveness to the combination therapy comprising the provided derivative NK and derivative T cell combo and anti-immune checkpoint inhibitor(s), the response can be measured by criteria comprising at least one of: clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST (Response Evaluation Criteria In Solid Tumors) criteria.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composition comprising two or more synthetic cell populations, wherein the composition comprises:
   (i) a first synthetic cell population comprising iPSC-derived NK cells, wherein the iPSC-derived NK cells comprise:
      (a) an exogenous CD16; and
      (b) a first chimeric antigen receptor (CAR); and
   (ii) a second synthetic cell population comprising iPSC-derived T cells, wherein the iPSC-derived T cells comprise: at least a second chimeric antigen receptor (CAR), and wherein the second CAR is expressed under control of an endogenous promoter of a TCR locus.

2. The composition of claim 1, wherein the exogenous CD16 is a high affinity non-cleavable exogenous CD16 (hnCD16); or wherein the exogenous CD16 comprises at least one of:
   (a) F176V and S197P in ectodomain domain of CD16;
   (b) a full or partial ectodomain originated from CD64;
   (c) a non-native (or non-CD16) transmembrane domain;
   (d) a non-native (or non-CD16) intracellular domain;
   (e) a non-native (or non-CD16) signaling domain;
   (f) a non-native stimulatory domain; and
   (g) transmembrane, signaling, and stimulatory domains that are not originated from CD16, and are originated from a same or different polypeptide.

3. The composition of claim 2, wherein:
   (a) the non-native transmembrane domain comprises a transmembrane domain of CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide;
   (b) the non-native stimulatory domain comprises a stimulatory domain of CD27, CD28, 4-1BB, OX40, ICOS, PD-1, LAG-3, 2B4, BTLA, DAP10, DAP12, CTLA-4, or NKG2D polypeptide;
   (c) the non-native signaling domain comprises a signaling domain of CD3ζ, 2B4, DAP10, DAP12, DNAM1, CD137 (4-1BB), IL21, IL7, IL12, IL15, NKp30, NKp44, NKp46, NKG2C, or NKG2D polypeptide; or
   (d) the non-native transmembrane domain comprises a transmembrane domain of NKG2D, the non-native stimulatory domain comprises a stimulatory domain of 2B4, and the non-native signaling domain comprises a signaling domain of CD3ζ.

4. The composition of claim 1, wherein the first CAR and the second CAR are the same or are different in targeting specificity, and wherein the first CAR or the second CAR is:
   (i) T cell specific or NK cell specific;
   (ii) a bi-specific antigen binding CAR;
   (iii) a switchable CAR;
   (iv) a dimerized CAR;
   (v) a split CAR;
   (vi) a multi-chain CAR;
   (vii) an inducible CAR;
   (viii) co-expressed with another CAR;
   (ix) co-expressed with a cell surface expressed exogenous cytokine and/or a receptor thereof;
   (x) co-expressed with a checkpoint inhibitor;
   (xi) specific to CD19 or BCMA; and/or
   (xii) specific to any one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein2 (EGP-2), epithelial glycoprotein-40 (EGP-40), epithelial cell adhesion molecule (EpCAM), EGFRVIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen.

5. The composition of claim 1, wherein the IPSC-derived NK cells comprise a cell surface receptor thereof, and further wherein the cell surface expressed exogenous cytokine and/or the receptor thereof:

(a) comprises at least one of IL2, IL4, IL6, IL7, IL9, IL10, IL11, IL12, IL15, IL18, IL21, and/or respective receptors thereof, or (b) comprises at least one of:
  (i) co-expression of IL15 and IL15Rα by using a self-cleaving peptide;
  (ii) a fusion protein of IL15 and IL15Rα;
  (iii) an IL15/IL15Rα fusion protein with intracellular domain of IL15Rα truncated;
  (iv) a fusion protein of IL15 and membrane bound Sushi domain of IL15Rα;
  (v) a fusion protein of IL15 and IL15Rβ;
  (vi) a fusion protein of IL15 and common receptor γC, wherein the common receptor γC is native or modified; and
  (vii) a homodimer of IL15Rβ.

6. The composition of claim 1, wherein the iPSC-derived NK cells and/or the iPSC-derived T cells further comprise one or more of:
  (i) HLA-I deficiency;
  (ii) HLA-II deficiency;
  (iii) introduced expression of HLA-G or non-cleavable HLA-G;
  (iv) at least one of lig$^-$, inR$^+$, cs-CD3$^+$, En$^+$, and Ab$^+$; wherein
    (1) lig$^-$ is negative in an expressed alloantigen,
    (2) inR$^+$ is positive in an expressed inactivation-CAR corresponding to the negative alloantigen;
    (3) cs-CD3$^+$ is positive in cell surface expressed CD3;
    (4) En$^+$ is positive in at least one expressed engager, wherein the engager comprises a bi-specific T cell engager (BiTE), or a tri-specific killer cell engager (TriKE); and
    (5) Ab$^+$ is positive in at least one expressed antibody or checkpoint inhibitor;
  (v) deletion or reduced expression in at least one of B2M, CIITA, TAP1, TAP2, Tapasin, NLRC5, PD1, LAG3, TIM3, RFXANK, RFX5, RAG1, RFXAP, and any gene in the chromosome 6p21 region; and
  (vi) introduced or increased expression in at least one of HLA-E, HLA-G, 41BBL, CD4, CD8, CD16, CD47, CD113, CD131, CD137, CD80, PDL1, $A_{2A}R$, TCR, Fc receptor, and surface triggering receptor for coupling with bi- or multi-specific or universal engagers.

7. The composition of claim 6, wherein:
  (i) the alloantigen comprises CD40L, OX40, or 4-1BB;
  (ii) the inactivation-CAR comprises CD40L-CAR, OX40-CAR, or 4-1BB-CAR;
  (iii) the BiTE or the TriKE recognizes (a) an immune cell surface molecule comprising CD3, CD28, CD5, CD16, NKG2D, CD64, CD32, CD89, NKG2C, or a chimeric Fc receptor thereof; and (b) a tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRVIII, EPCAM, FLT-3, FOLR1, FOLR3, GD2, gpA33, HER2, HM1.24, LGR5, MSLN, MCSP, MICA/B, PSMA, PAMA, P-cadherin, or ROR1;
  (iv) the BiTE comprises CD3-CD19, CD16-CD30, CD64-CD30, CD16-BCMA, CD64-BCMA, or CD3-CD33;
  (v) the TriKE comprises CD16-IL15-EPCAM, CD64-IL15-EPCAM, CD16-IL15-CD33, CD64-IL15-CD33, or NKG2C-IL15-CD33;
  (vi) the antibody comprises an anti-CD20, anti-HER2, anti-CD52, anti-EGFR, anti-CD123, anti-GD2, anti-PDL1, or anti-CD38 antibody; or
  (vii) the checkpoint inhibitor comprises (a) an antagonist to a checkpoint molecule comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one of atezolizumab, avelumab, durvalumab, ipilimumab, IPH4102, IPH43, IPH33, lirimumab, monalizumab, nivolumab, and pembrolizumab; or (c) one of atezolizumab, nivolumab, and pembrolizumab.

8. The composition of claim 1, wherein the iPSC-derived NK cells or the iPSC-derived T cells comprise:
  (i) one or more exogenous polynucleotides integrated in one desired integration site; or
  (ii) more than two exogenous polynucleotides integrated in different desired integration sites.

9. The composition of claim 8, wherein the desired integration site comprises at least one of AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD40L, CD44, CD54, CD56, CD58, CD69, CD71, OX40, 4-1BB, CIS, CBL-B, SOCS2, PD1, CTLA4, LAG3, TIM3, and TIGIT.

10. The composition of claim 8, wherein the desired integration site comprises TCR α or β constant region, CD25, CD38, CD40L, CD44, CD54, CD58, CD69, CD71, OX40 or 4-1BB; and optionally, wherein the TCRα or TCRβ, CD25, CD38, CD40L, CD44, CD54, 58, CD69, CD71, OX40 or 4-1BB is knocked out as a result of integrating said one or more exogenous polynucleotides at the respective integration site.

11. The composition of claim 1, wherein the iPSC-derived NK cells or the iPSC-derived T cells have at least one of the following characteristics comprising:
  (i) improved persistency and/or survival,
  (ii) increased resistance to native immune cells,
  (iii) increased cytotoxicity,
  (iv) improved tumor penetration,
  (v) enhanced or acquired ADCC,
  (vi) enhanced ability in migrating, and/or activating or recruiting bystander immune cells to tumor sites;
  (vii) enhanced ability to reduce tumor immunosuppression, and
  (viii) improved ability in rescuing tumor antigen escape, in comparison to its native counterpart cell obtained from peripheral blood, umbilical cord blood, or any other donor tissues.

12. The composition of claim 1, wherein the iPSC-derived NK cells or the iPSC-derived T cells comprise longer telomeres in comparison to their respective native counterpart cell obtained from peripheral blood, umbilical cord blood, or any other donor tissues.

13. The composition of claim 1, wherein the first synthetic cell population or the second synthetic cell population is modulated ex vivo.

14. The composition of claim 13, wherein the modulated first synthetic cell population comprising iPSC-derived NK cells comprises an increased number or ratio of type I NKT cells, and/or adaptive NK cells, as compared to the first synthetic cell population without being modulated; or wherein the second modulated synthetic cell population comprising iPSC-derived T cells comprises an increased number or ratio of naïve T cells, stem cell memory T cells, and/or central memory T cells, as compared to the second synthetic cell population without being modulated.

15. The composition of claim 1, wherein
   (i) the iPSC-derived NK cells and the iPSC-derived T cells are in a ratio ranging from 100:1 to 1:100;
   (ii) the composition further comprises one or more additional cell populations; or
   (iii) the composition further comprises one or more therapeutic agents.

16. The composition of claim 15, wherein the additional cell population comprises regulatory cells.

17. The composition of claim 16, wherein the regulatory cells are iPSC-derived immune regulatory cells or myeloid derived suppressor cells (MDSCs).

18. The composition of claim 15, wherein the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

19. The composition of claim 18, wherein the checkpoint inhibitor comprises:
   (a) one or more antagonist checkpoint molecules comprising PD-1, PDL-1, TIM-3, TIGIT, LAG-3, CTLA-4, 2B4, 4-1BB, 4-1BBL, A2AR, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR;
   (b) one or more of atezolizumab, avelumab, durvalumab, ipilimumab, IPH4102, IPH43, IPH33, lirimumab, monalizumab, nivolumab, and pembrolizumab; or
   (c) at least one of atezolizumab, nivolumab, and pembrolizumab.

20. The composition of claim 18, wherein the antibody comprises:
   (a) anti-CD20, anti-HER2, anti-CD52, anti-EGFR, anti-CD123, anti-GD2, anti-PDL1, and/or anti-CD38 antibody;
   (b) one or more of retuximab, veltuzumab, ofatumumab, ublituximab, ocaratuzumab, obinutuzumab, trastuzumab, pertuzumab, alemtuzumab, certuximab, dinutuximab, avelumab, daratumumab, isatuximab, MOR202, 7G3, CSL362, and elotuzumab; or
   (c) daratumumab.

21. A method of manufacturing the composition of claim 1, comprising:
   (I) differentiating a first genetically engineered iPSC to obtain a first synthetic cell population comprising iPSC-derived NK cells, wherein the first iPSC comprises a polynucleotide encoding (a) an exogenous CD16; and (b) a first chimeric antigen receptor (CAR); wherein the iPSC-derived NK cells comprise the exogenous CD16 and the first CAR; and
   (II) differentiating a second genetically engineered iPSC to obtain a second synthetic cell population comprising iPSC-derived T cells, wherein the second iPSC comprises a polynucleotide encoding at least a second chimeric antigen receptor (CAR), wherein the second CAR is expressed under the control of an endogenous promoter of a TCR locus, and wherein the iPSC-derived T cells comprise the second CAR,
   thereby manufacturing the composition of claim 1.

22. The method of claim 21, wherein the exogenous CD16 is a high affinity non-cleavable exogenous CD16 (hnCD16); or wherein the exogenous CD16 comprises at least one of:
   (a) F176V and S197P in ectodomain domain of CD16;
   (b) a full or partial ectodomain originated from CD64;
   (c) a non-native (or non-CD16) transmembrane domain;
   (d) a non-native (or non-CD16) intracellular domain;
   (e) a non-native (or non-CD16) signaling domain;
   (f) a non-native stimulatory domain; and
   (g) transmembrane, signaling, and stimulatory domains that are not originated from CD16, and are originated from a same or different polypeptide.

23. The method of claim 22, wherein:
   (a) the non-native transmembrane domain comprises a transmembrane domain of CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide;
   (b) the non-native stimulatory domain comprises a stimulatory domain of CD27, CD28, 4-1BB, OX40, ICOS, PD-1, LAG-3, 2B4, BTLA, DAP10, DAP12, CTLA-4, or NKG2D polypeptide;
   (c) the non-native signaling domain comprises a signaling domain of CD3C, 2B4, DAP10, DAP12, DNAM1, CD137 (4-1BB), IL21, IL7, IL12, IL15, NKp30, NKp44, NKp46, NKG2C, or NKG2D polypeptide; or
   (d) the non-native transmembrane domain comprises a transmembrane domain of NKG2D, the non-native stimulatory domain comprises a stimulatory domain of 2B4, and the non-native signaling domain comprises a signaling domain of CD3ζ.

24. The method of claim 21, wherein the first CAR and the second CAR are the same or are different in targeting specificity, and the first CAR or the second CAR is:
   (i) T cell specific or NK cell specific;
   (ii) a bi-specific antigen binding CAR;
   (iii) a switchable CAR;
   (iv) a dimerized CAR;
   (v) a split CAR;
   (vi) a multi-chain CAR;
   (vii) an inducible CAR;
   (viii) co-expressed with another CAR;
   (ix) co-expressed with a cell surface expressed exogenous cytokine and/or a receptor thereof;
   (x) co-expressed with a checkpoint inhibitor;
   (xi) specific to CD19 or BCMA; and/or
   (xii) specific to any one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen.

25. The method of claim 21, wherein the iPSC-derived NK cells comprise a cell surface expressed exogenous cytokine and/or a receptor thereof, and further wherein the cell surface expressed exogenous cytokine and/or the receptor thereof:
   (a) comprises at least one of IL2, IL4, IL6, IL7, IL9, IL10, IL11, IL12, IL15, IL18, IL21, and/or respective receptors thereof, or
   (b) comprises at least one of:
      (i) co-expression of IL15 and IL15Rα by using a self-cleaving peptide;
      (ii) a fusion protein of IL15 and IL15Rα;
      (iii) an IL15/IL15Rα fusion protein with intracellular domain of IL15Rα truncated;
      (iv) a fusion protein of IL15 and membrane bound Sushi domain of IL15Rα;
      (v) a fusion protein of IL15 and IL15Rβ;
      (vi) a fusion protein of IL15 and common receptor γC, wherein the common receptor γC is native or modified; and
      (vii) a homodimer of IL15Rβ.

26. The method of claim 21, wherein the first genetically engineered iPSC or the second genetically engineered iPSC further comprises one or more of:
   (i) HLA-I deficiency;
   (ii) HLA-II deficiency;
   (iii) introduced expression of HLA-G or non-cleavable HLA-G;
   (iv) at least one of lig$^-$, inR$^+$, cs-CD3$^+$, En$^+$, and Ab$^+$; wherein
      (1) lig$^-$ is negative in an expressed alloantigen;
      (2) inR$^+$ is positive in an expressed inactivation-CAR corresponding to the negative alloantigen;
      (3) cs-CD3$^+$ is positive in cell surface expressed CD3;
      (4) En$^+$ is positive in at least one expressed engager, wherein the engager comprises a bi-specific T cell engager (BiTE), or a tri-specific killer cell engager (TriKE); and
      (5) Ab$^+$ is positive in at least one expressed antibody or checkpoint inhibitor;
   (v) deletion or reduced expression in at least one of B2M, CIITA, TAP1, TAP2, Tapasin, NLRC5, PD1, LAG3, TIM3, RFXANK, RFX5, RAG1, RFXAP, and any gene in the chromosome 6p21 region; and
   (vi) introduced or increased expression in at least one of HLA-E, HLA-G, 41BBL, CD4, CD8, CD16, CD47, CD113, CD131, CD137, CD80, PDL1, $A_{2A}R$, TCR, Fc receptor, and surface triggering receptor for coupling with bi- or multi-specific or universal engagers.

27. The method of claim 26, wherein:
   (i) the alloantigen comprises CD40L, OX40, or 4-1BB;
   (ii) the inactivation-CAR comprises CD40L-CAR, OX40-CAR, or 4-1BB-CAR;
   (iii) the BiTE or the TriKE is specific to (a) an immune cell surface molecule comprising CD3, CD28, CD5, CD16, NKG2D, CD64, CD32, CD89, NKG2C, or a chimeric Fc receptor thereof; and (b) a tumor surface molecule comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRVIII, EPCAM, FLT-3, FOLR1, FOLR3, GD2, gpA33, HER2, HM1.24, LGR5, MSLN, MCSP, MICA/B, PSMA, PAMA, P-cadherin, or ROR1;
   (iv) the BiTE comprises CD3-CD19, CD16-CD30, CD64-CD30, CD16-BCMA, CD64-BCMA, or CD3-CD33;
   (v) the TriKE comprises CD16-IL15-EPCAM, CD64-IL15-EPCAM, CD16-IL15-CD33, CD64-IL15-CD33, or NKG2C-IL15-CD33;
   (vi) the antibody comprises an anti-CD20, anti-HER2, anti-CD52, anti-EGFR, anti-CD123, anti-GD2, anti-PDL1, or anti-CD38 antibody; or
   (vii) the checkpoint inhibitor comprises (a) an antagonist to a checkpoint molecule comprising PD-1, PDL-1, TIM-3, TIGIT, LAG-3, CTLA-4, 2B4, 4-1BB, 4-1BBL, A2AR, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (b) one of atezolizumab, avelumab, durvalumab, ipilimumab, IPH4102, IPH43, IPH33, lirimumab, monalizumab, nivolumab, and pembrolizumab; or (c) one of atezolizumab, nivolumab, and pembrolizumab.

28. The method of claim 21, wherein the first genetically engineered iPSC or the second genetically engineered iPSC comprise:
   (i) one or more exogenous polynucleotides integrated in one desired integration site; or
   (ii) more than two exogenous polynucleotides integrated in different desired integration sites.

29. The method of claim 28, wherein the desired integration site comprises at least one of AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region, NKG2A, NKG2D, CD25, CD38, CD40L, CD44, CD54, CD56, CD58, CD69, CD71, OX40, 4-1BB, CIS, CBL-B, SOCS2, PD1, CTLA4, LAG3, TIM3, and TIGIT.

30. The method of claim 28, wherein the desired integration site comprises TCR α or β constant region, CD25, CD38, CD40L, CD44, CD54, CD58, CD69, CD71, OX40 or 4-1BB; and optionally, wherein the TCRα or TCRβ, CD25, CD38, CD40L, CD44, CD54, CD58, CD69, CD71, OX40 or 4-1BB is knocked out as a result of integrating said one or more exogenous polynucleotides at the respective integration site.

31. The method of claim 21, wherein the iPSC-derived NK cells or the iPSC-derived T cells have at least one of the following characteristics comprising:
   (i) improved persistency and/or survival,
   (ii) increased resistance to native immune cells,
   (iii) increased cytotoxicity,
   (iv) improved tumor penetration,
   (v) enhanced or acquired ADCC,
   (vi) enhanced ability in migrating, and/or activating or recruiting bystander immune cells to tumor sites;

(vii) enhanced ability to reduce tumor immunosuppression, and (viii) improved ability in rescuing tumor antigen escape, in comparison to its native counterpart cell obtained from peripheral blood, umbilical cord blood, or any other donor tissues.

32. The method of claim 21, wherein the first synthetic cell population or the second synthetic cell population is modulated ex vivo.

33. The method of claim 32, wherein the modulated first synthetic cell population comprising iPSC-derived NK cells comprises an increased number or ratio of type I NKT cells, and/or adaptive NK cells, as compared to the first synthetic cell population without being modulated; or wherein the second modulated synthetic cell population comprising iPSC-derived T cells comprises an increased number or ratio of naïve T cells, stem cell memory T cells, and/or central memory T cells, as compared to the second synthetic cell population without being modulated.

34. The method of claim 21, wherein:
    (i) the iPSC-derived NK cells and the iPSC-derived T cells are in a ratio ranging from 100:1 to 1:100;
    (ii) the method further comprises adding one or more additional cell populations to the first and second synthetic cell populations; or
    (iii) the method further comprises adding one or more therapeutic agents to the first and second synthetic cell populations.

35. The method of claim 34, wherein the one or more additional cell populations comprise regulatory cells.

36. The method of claim 35, wherein the regulatory cells are iPSC-derived immune regulatory cells or myeloid derived suppressor cells (MDSCs).

37. The method of claim 34, wherein the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMID).

38. The method of claim 37, wherein the checkpoint inhibitor comprises:
    (a) one or more antagonist checkpoint molecules comprising PD-1, PDL-1, TIM-3, TIGIT, LAG-3, CTLA-4, 2B4, 4-1BB, 4-1BBL, A2AR, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR;
    (b) one or more of atezolizumab, avelumab, durvalumab, ipilimumab, IPH4102, IPH43, IPH33, lirimumab, monalizumab, nivolumab, and pembrolizumab; or
    (c) at least one of atezolizumab, nivolumab, and pembrolizumab.

39. The method of claim 37, wherein the antibody comprises:
    (a) anti-CD20, anti-HER2, anti-CD52, anti-EGFR, anti-CD123, anti-GD2, anti-PDL1, and/or anti-CD38 antibody;
    (b) one or more of retuximab, veltuzumab, ofatumumab, ublituximab, ocaratuzumab, obinutuzumab, trastuzumab, pertuzumab, alemtuzumab, certuximab, dinutuximab, avelumab, daratumumab, isatuximab, MOR202, 7G3, CSL362, and elotuzumab; or
    (c) daratumumab.

40. The method of claim 21, further comprising combining the first synthetic cell population and the second synthetic cell population into a mixed population.

\* \* \* \* \*